(12) United States Patent  
Yun et al.

(10) Patent No.: US 8,067,567 B2  
(45) Date of Patent: Nov. 29, 2011

(54) MODIFIED TERT PROMOTER WITH ENHANCED TUMOR-SPECIFICITY AND STRENGTH AND RECOMBINANT VECTOR COMPRISING THE SAME

(75) Inventors: Chae-Ok Yun, Seoul (KR); Joo-Hang Kim, Seoul (KR); Jai-Myung Yang, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 1202 days.

(21) Appl. No.: 10/547,233

(22) PCT Filed: Feb. 27, 2004

(86) PCT No.: PCT/KR2004/000427  
§ 371 (c)(1),  
(2), (4) Date: Jun. 27, 2006

(87) PCT Pub. No.: WO2004/076668  
PCT Pub. Date: Sep. 10, 2004

(65) Prior Publication Data  
US 2007/0059287 A1    Mar. 15, 2007

(30) Foreign Application Priority Data  
Feb. 27, 2003  (KR) ................. 10-2003-0012364

(51) Int. Cl.  
*C07H 21/04* (2006.01)  
*C12N 15/63* (2006.01)  
*A01N 63/00* (2006.01)  
*A61K 48/00* (2006.01)

(52) U.S. Cl. .............. 536/24.1; 435/320.1; 424/93.1; 514/44 R

(58) Field of Classification Search .................. None  
See application file for complete search history.

(56) References Cited

U.S. PATENT DOCUMENTS  
7,491,525 B2 * 2/2009 Qian et al. ................ 435/235.1

FOREIGN PATENT DOCUMENTS  
WO          00/03104       8/2000  
WO     WO 03/006640 A1 *  1/2003  
WO     WO 03/013555       2/2003

OTHER PUBLICATIONS pXC1 vector map, 1 page, printed from Microbix Biosystems website, Nov. 20, 2010.*  
pXC1 vector DNA sequence, 4 pages, printed from Microbix Biosystems website, Nov. 20, 2010.*  
Supplementary European Search Report, dated Jun. 29, 2006, for EPO Application No. EP04715577.  
Kirch et al., "Tumor-specific activation of hTERT-derived promoters by tumor suppressive E1A-mutants involves recruitment of p300/CBP/HAT and suppression of HDAC-1 and defines a combined tumor targeting and suppression system" Oncogene, vol. 21, No. 52, Nov. 14, 2002, pp. 7991-8000.  
Wick et al., "Genomic organization and promoter characterization of the gene encoding the human telomerase reverse transcriptase (hTERT)", Gene: An International Journal on Genes and Genomes, Elsevier, Amsterdam, NL, vol. 232, May 17, 1999, pp. 97-106.  
Greenberg et al., "Telemerase reverse transcriptase gene is a a direct target of c-Myc but is not functionally equivalent in cellular transformation" Oncogene, Basingstoke, Hants, GB, vol. 18, 1999, pp. 1219-1226.  
Kim, E. et al., "Ad-mTERT-Δ19, a Conditional Replication-Competent Adenovirus Driven by the Human Telomerase Promoter, Selectively Replicates in and Elicits Cytopathic Effect in a Cancer Cell-Specific Manner" Human Gene Therapy, vol. 14, pp. 1415-1428, Oct. 10, 2003.  
Kyo, S. et al., "Sp1 cooperates with c-Myc to activate transcription of the human telomerase reverse transcriptase gene (hTERT)" Nucleic Acids Research, vol. 28, No. 3, pp. 669-677, 2000.  
Takakura, M. et al., "Cloning of Human Telomerase Catalytic Subunit (hTERT) Gene Promoter and Identification of Proximal Core Promoter Sequences Essential for Transcriptional Activation in Immortalized and Cancer Cells" Cancer Research, vol. 59, pp. 551-557, Feb. 1999.  
Horikawa, I. et al., "Cloning and Characterization of the Promoter Region of *Human Telomerase Reverse Transcriptase* Gene" Cancer Research, vol. 59, pp. 826-830, Feb. 1999.  
Kim, J. et al., "Evaluation of E1B gene-attenuated replicating adenoviruses for cancer gene therapy"Cancer Gene Therapy, vol. 9, pp. 725-736, 2002.  
Fisher, K.J. et al., "Recombinant Adenovirus Deleted of All Viral Genes for Gene Therapy of Cystic Fibrosis" Virology, vol. 217, pp. 11-22, 1996.  
Kumar-Singh, R. et al., "Encapsidated adenovirus minichromosomes allow delivery and expression of a 14 kb dystrophin cDNA to muscle cells" Human Molecular Genetics, vol. 5, No. 7, pp. 913-921, 1996.  
Abdallah, B. et al., "Non-viral gene transfer: Applications in developmental biology and gene therapy" Biology of the Cell, vol. 85, pp. 1-7, 1995.  
Mizuguchi, H. et al., "Approaches for generating recombinant adenovirus vectors" Advanced Drug Reviews, vol. 52, pp. 165-176, 2001.

* cited by examiner

*Primary Examiner* — Michael Burkhart  
(74) *Attorney, Agent, or Firm* — Holme Roberts & Owen LLP

(57) ABSTRACT

The present invention relates to a transcriptional regulatory sequence with enhanced tumor-specificity and strength and a recombinant vector comprising the transcriptional regulatory sequence. More particularly, the present invention relates to a transcriptional regulatory sequence comprising a human telomere reverse transcriptase (hTERT) promoter linked to a nucleotide sequence that comprises one or more c-Myc binding sites and/or one or more Sp1 binding sites, and a recombinant vector comprising a certain gene that is operably linked to the above transcriptional regulatory sequence.

27 Claims, 55 Drawing Sheets

FIG. 1

```
agatct[ctcc gctggggccc tcgctggcgt ccctgcaccc tgggagcgcg agcggcgcgc    -840
Bgl II
gggcggggaa gcgcggccca gacccccggg tccgcccgga gcagctgcgc tgtcggggcc    -780 aggccgggct cccagtggat tcgcgggcac agacgcccag gaccgcgctt cccacgtggc    -720
                                                        E-box
ggagggactg gggacccggg cacccgtcct gccccttcac cttccagctc cgcctcctcc    -660
                                                        Sp1
gcgcggacct cgcccgtcc cgaccctcc cgggtcccg gcccagcccc ctccgggccc       -600
          Sp1                                Sp1
tcccagcccc tcccttcct ttcgcggcc ccgcctctc ctcgcggcgc gagtttcagg       -540
Sp1                         Sp1
cagcgctgcg tcctgctgcg cacgtggaa gccctggccc cggccacccc cgcg]tga agc   -480
                      E-box                                HindIII
ttgcatgcct gcaggtcgac tctagaggat ctactagtca tatggatgag ctcgagctgc    -420 accctgggag cgcgagcggc gcgcgggcgg ggaagcgcgg cccagacccc cgggtccgcc    -360 cggagcagct gcgctgtcgg ggccaggccg ggctcccagt ggattcgcgg gcacagacgc    -300 ccaggaccgc gcttccacg tggcggaggg actggggacc cgggcacccg tcctgcccct    -240
                E-box
tcaccttcca gctccgcctc ctccgcgcgg acccgccct gtcccgaccc ctcccgggtc    -180
             Sp1                  Sp1
cccggcccag ccccctccgg gccctcccag ccctccccct tcctttccgc ggcccgccc    -120
       Sp1                   Sp1                            Sp1
tctcctcgag ctcgagatcg gatccccggg taccgaggcg aattcggctt ctcgagccac    -60 tcttgagtgc cagcgagtag agttttctcc tccgagccgc tccgacaccg ggactgaaaatg
                                                                  ↳
```

BJ

SEQUENCE LISTING

<160> NUMBER OF SEQ ID NOS: 13

<210> SEQ ID NO 1
<211> LENGTH: 408
<212> TYPE: DNA
<213> ORGANISM: Homo sapiens
<220> FEATURE:
<221> NAME/KEY: promoter
<222> LOCATION: (1)..(408)

<400> SEQUENCE: 1

```
ctccgctggg gccctcgctg gcgtccctgc accctgggag cgcgagcggc gcgcgggcgg      60
ggaagcgcgg cccagacccc cgggtccgcc cggagcagct gcgctgtcgg ggccaggccg     120
ggctcccagt ggattcgcgg gcacagacgc ccaggaccgc gcttccacg  tggcggaggg     180 actggggacc cgggcacccg tcctgccct  tcaccttcca gctccgcctc ctccgcgcgg     240
accccgcccc gtcccgaccc ctcccgggtc ccggccag  cccctccgg gccctcccag      300 ccctccct  tcctttccgc ggccccgccc tctcctcgcg gcgcgagttt caggcagcgc     360
tgcgtcctgc tgcgcacgtg ggaagccctg gccccggcca ccccgcg                   408
```

```
<210> SEQ ID NO 2
<211> LENGTH: 6
<212> TYPE: DNA
<213> ORGANISM: Homo sapiens
<220> FEATURE:
<221> NAME/KEY: protein_bind
<222> LOCATION: (1)..(6)

<400> SEQUENCE: 2 cacgtg                                                                    6

<210> SEQ ID NO 3
<211> LENGTH: 6
<212> TYPE: DNA
<213> ORGANISM: Homo sapiens
<220> FEATURE:
<221> NAME/KEY: protein_bind
<222> LOCATION: (1)..(6)

<400> SEQUENCE: 3 cacgcg                                                                    6

<210> SEQ ID NO 4
<211> LENGTH: 6
<212> TYPE: DNA
<213> ORGANISM: Homo sapiens
<220> FEATURE:
<221> NAME/KEY: protein_bind
<222> LOCATION: (1)..(6)

<400> SEQUENCE: 4 catgcg                                                                    6

<210> SEQ ID NO 5
<211> LENGTH: 6
<212> TYPE: DNA
<213> ORGANISM: Homo sapiens
<220> FEATURE:
<221> NAME/KEY: protein_bind
<222> LOCATION: (1)..(6)

<400> SEQUENCE: 5 gggcgg                                                                    6

<210> SEQ ID NO 6
<211> LENGTH: 6
<212> TYPE: DNA
<213> ORGANISM: Homo sapiens
<220> FEATURE:
<221> NAME/KEY: protein_bind
<222> LOCATION: (1)..(6)

<400> SEQUENCE: 6 ccgccc                                                                    6

<210> SEQ ID NO 7
<211> LENGTH: 9
<212> TYPE: DNA
<213> ORGANISM: Homo sapiens
<220> FEATURE:
<221> NAME/KEY: protein_bind
<222> LOCATION: (1)..(9)

<400> SEQUENCE: 7 ctccgcctc                                                                 9

<210> SEQ ID NO 8
```

```
<211> LENGTH: 9
<212> TYPE: DNA
<213> ORGANISM: Homo sapiens
<220> FEATURE:
<221> NAME/KEY: protein_bind
<222> LOCATION: (1)..(9)

<400> SEQUENCE: 8 cccagcccc                                                              9

<210> SEQ ID NO 9
<211> LENGTH: 7
<212> TYPE: DNA
<213> ORGANISM: Homo sapiens
<220> FEATURE:
<221> NAME/KEY: protein_bind
<222> LOCATION: (1)..(7)

<400> SEQUENCE: 9 ggggcgg                                                                7

<210> SEQ ID NO 10
<211> LENGTH: 10
<212> TYPE: DNA
<213> ORGANISM: Homo sapiens
<220> FEATURE:
<221> NAME/KEY: protein_bind
<222> LOCATION: (1)..(10)

<400> SEQUENCE: 10
cccccgcccc                                                            10

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
cccaaagctt aggccgattc gagatctctc c                                    31

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
gaattcaagc ttcgcggggt ggccggggcc                                      30

<210> SEQ ID NO 13
<211> LENGTH: 902
<212> TYPE: DNA
<213> ORGANISM: Artificial Sequence
<220> FEATURE:
<223> OTHER INFORMATION: promoter

<400> SEQUENCE: 13
agatctctcc gctggggccc tcgctggcgt ccctgcaccc tgggagcgcg agcggcgcgc      60
gggcggggaa gcgcggccca gaccccgggt tcgcccgga gcagctgcgc tgtcgggcc       120 aggccgggct cccagtggat tcgcgggcac agacgcccag gaccgcgctt cccacgtggc     180
ggagggactg gggaccccggg cacccgtcct gcccctcac cttccagctc cgcctcctcc     240
gcgcggaccc cgccccgtcc cgacccctcc cgggtcccg gcccagcccc ctccgggccc      300
```

```
tcccagcccc tccccttcct ttccgcggcc ccgccctctc ctcgcggcgc gagtttcagg    360
cagcgctgcg tcctgctgcg cacgtgggaa gccctggccc cggccacccc cgcgtgaagc    420
ttgcatgcct gcaggtcgac tctagaggat ctactagtca tatggatgag ctcgagctgc    480
accctgggag cgcgagcggc gcgcgggcgg ggaagcgcgg cccagacccc cgggtccgcc    540
cggagcagct gcgctgtcgg ggccaggccg ggctcccagt ggattcgcgg gcacagacgc    600
ccaggaccgc gcttcccacg tggcggaggg actggggacc cgggcacccg tcctgcccct    660
tcaccttcca gctccgcctc ctccgcgcgg accccgcccc gtcccgaccc ctcccgggtc    720
cccggcccag cccctccgg gccctcccag cccctcccct tcctttccgc ggccccgccc    780
tctcctcgag ctcgagatcg gatccccggg taccgaggcg aattcggctt ctcgagccac    840
tcttgagtgc cagcgagtag agttttctcc tccgagccgc tccgacaccg ggactgaaaa    900
tg                                                                   902
```

MODIFIED TERT PROMOTER WITH ENHANCED TUMOR-SPECIFICITY AND STRENGTH AND RECOMBINANT VECTOR COMPRISING THE SAME

TECHNICAL FIELD

The present invention relates to a transcriptional regulatory sequence with enhanced tumor-specificity and strength and a recombinant vector comprising the transcriptional regulatory sequence. More particularly, the present invention relates to a transcriptional regulatory sequence comprising a human telomere reverse transcriptase (hTERT) promoter linked to a nucleotide sequence that comprises one or more c-Myc binding sites and/or one or more Sp1 binding sites, and a recombinant vector comprising a certain gene that is operably linked to the transcriptional regulatory sequence.

BACKGROUND ART

Adenovirus was known to have several advantages of mediating gene transfer with high efficiency in vivo and in vitro, transferring exogenous genes into a variety of cell types and allow for expression of the genes, regardless of cell division state of target cells, producing high-titer virus and not causing cancer in humans. Due to these advantages, adenovirus has greatly increased in use in clinical cancer gene therapy (Graham, F. L. 'Adenovirus vectors for high-efficiency gene transfer into mammalian cells.' Immunol. Today, 2000, 21, 426-8; Castell, J. V. et al. 'Adenovirus-mediated gene transfer into human hepatocytes: analysis of the biochemical functionality of transduce cells.' Gene Ther., 1997, 4, 455-64). When cancer is treated using gene therapy mediated by adenovirus, long term expression of therapeutic genes is not required, and host immune response induced by virus or viral proteins is not highly significant or even can be beneficial in some cases. Thus, adenovirus becomes attractive as a gene transfer vehicle for cancer therapy.

However, the most conventional recombinant adenoviruses for cancer therapy, which are known as replication-incompetent first-generation viruses, display antitumor activity in only primary infected cells or a very small number of surrounding cells (Vile, R. G. et al. 'Cancer gene therapy: hard lesion and new courses.' Gene Ther., 2000, 7, 2-8; Paillard, F. Cancer gene therapy annual conference. 1997: trends and news, Hum. Gene Ther., 1998, 4, 283-6; Lattime, E. C. et al. 'Selectively replicating viruses as therapeutic agents against cancer.' in: D. Kirn (Ed), Gene therapy of cancer, Academic Press, New York, 1999, 235-50).

To overcome such problems, the McCormick research group reported first a recombinant adenovirus that replicates selectively in tumor cells and eventually kills the tumor cells. After that, a variety of efforts were made to develop modified adenoviruses causing tumor-specific cytolysis (Bischoff, J. R. et al. 'An adenovirus mutant that replicates selectively in P53-deficient human tumor cells.' Science, 1996, 18, 274 (5286), 373-6; Heise, C. et al. 'ONYX-015, an E1B gene-attenuated adenovirus, causes tumor-specific cytolysis and antitumoral efficacy that can be augmented by standard chemotherapeutic agents.' Nat. Med., 1997, 3(6), 639-45). The oncolytic adenoviral vectors have a domino effect on cancer therapy by displaying antitumor activity not only in primary infected cells, but also in secondarily infecting surrounding tumor cells by replication thereby remarkably increasing therapeutic efficacy against cancer. Also, the oncolytic adenoviral vectors further include the advantage of being inhibited replication in surrounding normal cells, and thus, having low cytotoxicity to the normal cells.

Tumor-specific replication-competent adenoviruses have been developed mainly by two methods, as follows. First, tumor-specific replication-competent adenoviruses can be developed by regulating cancer tissues expression of E1A protein which is essential for replication of adenovirus using tumor- or tissue-specific promoters. Rodriguez, R. et al. reported in 1997 that, when the upstream promoter of E1A gene is replaced by the promoter/enhancer region of prostate-specific antigen (PSA) selectively expressed in prostate cancer cells, adenovirus replicates selectively in PSA-positive prostate cancer cells (Rodriguez, R. et al. 'Prostate attenuated replication competent adenovirus (ARCA) CN706: a selective cytotoxic for prostate-specific antigen-positive prostate cancer cells.' Cancer Res., 1997, 1, 57(13), 2559-63). The prostate attenuated replication competent adenovirus (ARCA) CN706 (Calydon Pharmaceuticals, Calif., USA) is under a phase I clinical trial in patients suffering from recurred prostate cancer. In addition, some attempts have been made to develop more potent prostate cancer-specific replicative adenoviruses. For example, the expression of the two early genes, E1A and E1B, of adenovirus can be regulated according to expression levels of PSA by additionally inserting a prostate-specific enhancer region into the upstream of E1B gene that is one of early genes of adenovirus (Yu, D. C. et al. 'Identification of the transcriptional regulatory sequences of human kallikrein 2 and their use in the construction of cyldon virus 764, an attenuated replication competent adenovirus for prostate cancer therapy.' Cancer Res., 1999, 1, 59(7), 1498-504). Further, employing promoters of genes activated only in specific tumor cells, such as alpha-fetoprotein (AFP), carcinoembryonic antigen (CEA) and MUC-1, tumor-specific replication-competent adenoviruses have been developed (Kanai, F. et al. 'Gene therapy for alpha-fetoprotein-producing human hepatoma cells by adenovirus-mediated transfer of the herpes simplex virus thymidine kinase gene.' Hepatology, 1996, 53, 963-7; Marshall, J. F. et al. 'Tissue specific promoters in targeting systemically delivered gene therapy.' Semin. Oncol., 1996, 23, 154-8; Osaki, T. et al. 'Gene therapy for carcinoembryonic antigen-producing human lung cancer cells by cell type specific expression of herpes simplex virus thymidine kinase gene.' Cancer Res., 1994, 54, 5258-61; Kurihara, T. et al. 'Selectivity of a replication-competent adenovirus for human breast carcinoma cells expressing the MUC1 antigen.' J. Clin. Invest., 2000, 106, 763-71).

In the second strategy for the development of tumor-specific replication-competent adenoviruses, some attempts have been tried to develop tumor-specific replication-competent adenoviruses by selectively knocking out adenoviral genes that are essential for active viral replication in normal cells but not essential in tumor cells (Whyte, P. et al. 'Cellular targets for transformation by the adenovirus E1A proteins.' Cell, 1989, 56, 67-75; Fueyo, J. et al. 'A mutant oncolytic adenovirus targeting the Rb pathway produces anti-glioma effect in vivo.' Oncogen., 2000, 19, 2-12). Bischoff J. R. et al. reported first in 1996 that an adenovirus mutant deficient in the adenoviral early protein E1B-55kD that functions to bind to and then inactivate the tumor suppressor protein p53 is capable of replicating selectively in p53 deficient tumor cells. When a wild-type adenovirus infects normal cells, the infected cells inhibit viral proliferation by activating the tumor suppressor protein p53. The E1B-55kD protein is responsible for the p53 activation, which binds to p53 and inhibits its function. As a result the wild-type adenovirus actively proliferates in the normal cells and eventually destroys the cells (Yew, P. R. et al. 'Adenovirus E1B oncoprotein tethers a transcriptional repression domain to p53.' Genes, 1994, 8, 190-202; Dobner, T. et al. 'Blockage by adenovirus E4 or F6 of transcriptional activation by the p53 tumor suppressor.' Science, 1996, 7, 272(5267), 1470-3.). However, when the E1B-55kD gene-deleted recombinant adenovirus infects normal cells, viral proliferation is inhibited because p53 inactivation is not induced, whereas the virus actively proliferates in several tumor cells in which the function of p53 is inhibited and eventually induces cell death of the infected cells. Based on these fact, the present inventors developed an E1B-55kD gene-deleted, tumor-specific cytolytic adenovirus, YKL-1, which was demonstrated to be superior to the conventional first-generation adenoviruses that is replication-deficient in transfection efficacy. YKL-1 also has the oncolytic effect against several human tumor cells (Lee, H. et al. 'Oncolytic potential of E1B55kDa-deleted YKL-1 recombinant adenovirus: Correlation with p53 functional status.' Int. J. Cancer, 2000, 88, 454-63).

In addition to inactivating p53, the E1B55kD protein stimulates to transport the adenovirus mRNA to the cytosol and synthesize the composed proteins of adenoviruses, and thus is essential for replication of adenoviruses. Therefore, the E1B55kD gene-deleted replication-competent adenovirus is proliferation-restricted in tumor cells and thus has reduced cytotoxic activity, resulting in a decrease in vivo antitumor efficacy. To solve this problem, the present inventors construct an Ad-ΔE1B19 adenovirus deleted for the adenovirus E1B19kD gene of which translational product functions to inhibit apoptosis, and revealed that the Ad-ΔE1B19 adenovirus has greatly enhanced cytolytic effect and in vivo antitumor effect (Kim, J. et al. 'Evaluation of E1B gene attenuated replicating adenoviruses for cancer gene therapy.' Cancer Gene Therapy, 2002, 9, 725-736). However, in this case that the E1B55kD gene is not deleted to achieve effective replication of adenovirus. Cell death is increased by elevated adenovirus replication, but the tumor-specific replication activity is lost. Thus, the Ad-ΔE1B19 adenovirus is required to have tumor specificity for use in cancer treatment by gene therapy.

Human telomere reverse transcriptase (hTERT) is one subunit of the telomerase holoenzyme that is involved in uniformly maintaining telomere length during chromosome replication, and known to be related to cell aging, tumorogenesis and cell immortalization (Counter, C. M. et al. 'Telomere shortening associated with chromosome instability is arrested in immortal cell which express telomerase activity.' EMBO J. 1992, 11, 1921-29; Kim, N. W. et al. 'Specific association of human telomerase activity with immortal cells and cancer.' Science, 1994, 21, 66, 2011-5; Harley, C. B. et al. 'Telomeres shorten during aging of human fibroblasts.' Nature, 1990, 345, 458-60). Telomerase activity is detected in germline cells and lymphocytes in human ovaries and testes, but not found in normal somatic cells (Wright, W. E. et al. 'Telomerase activity in human germline and embryonic tissues and cells.' Dev. Genet. 1996, 18, 173-9). Therefore, normal somatic cells have below a threshold length of telomere after a limited number of cell divisions, and eventually senesce (Yasumoto, S. et al. 'Telomerase activity in normal human epithelial cells.' Oncogene. 1996, 13, 433-9). In contrast, telomerase activity is elevated in benign tumor cells before tumor progression and cancer cells (Broccoli, D. et al. 'Telomerase activity in normal and malignant hematopoietic cells.' Proc. Nat'l. Acad. Sci. USA. 1995, 92, 9082-6.). After the first report in that telomerase activity is increased in ovarian cancer, elevated telomerase activity is detected in almost all human cancers, including blood cancer, stomach cancer, lung cancer, liver cancer, large intestine cancer, brain cancer, prostate cancer, head and neck cancer and breast cancer (Counter, C. M. et al. 'Telomerase activity in human ovarian carcinoma.' Proc. Nat'l. Acad. Sci. USA. 1994, 91, 2900-4; Counter, C. M. et al. 'Stabilization of short telomeres and telomerase activity accompany immortalization of Epstein-Barr virus-transformed human B lympho-cytes.' J. Virol., 1994, 68, 3410-4; Shay, J. W. et al. 'A survey of telomerase activity in human cancer.' Eur. J. Cancer, 1997, 33, 787-91; Harle-Bachor, C. et al. 'Telomerase activity in the regenerative basal layer of the epidermis in human skin and in immortal and carcinoma-derived skin keratinocytes.' Proc. Nat'l. Acad. Sci. USA. 1996, 93, 6476-81).

Expression of hTERT that plays a critical role in the function of telomerase is associated with telomerase activity. Recent data suggest that telomerase expression is regulated according to the activity of hTERT promoter, that is, mRNA levels of hTERT. The minimum hTERT promoter region to regulate hTERT activity is 181 bp in length. The wild-type hTERT promoter contains two c-Myc binding sites and five Sp1 binding sites. According to some reports the c-Myc oncoprotein which is highly expressed in tumor cells compared to normal cells is binding to the transcription factor Sp1. This binding activates hTERT promoter. Takakura M. et al. reported in 1999 that the activity of hTERT promoter is elevated by overexpression of c-Myc (Cerni, C. 'Telomeres, telomerase, and myc.' An update. Mutat. Res., 2000, 462, 31-47; Greenberg, R. A. et al. 'elomerase reverse transcriptase gene is a direct target of c-Myc but is not functionally equivalent in cellular transformation.' Oncogene, 1999, 18, 1219-26; Takakura, M. et al., 'Cloning of human telomerase reverse transcriptase gene promoter and identification of proximal core promoter essential for transcriptional activation of hTERT in immortalized and cancer cells.' Cancer Res., 1999, 59, 551-9).

As described by Shoji K. et al., apoptosis-inducing toxic genes such as caspase-8 can be expressed in only tumor cells by inducing expression of cancer cell-specific genes using the hTERT promoter (Shoji, K. et al. 'A novel telomerase-specific gene therapy: gene transfer of caspase-8 utilizing the human telomerase catalytic subunit gene promoter.' Human Gene Therapy, 2000, 11, 1397-406.). However, the use of the hTERT promoter alone has a limitation in attaining sufficient tumor specificity.

DISCLOSURE OF THE INVENTION

To solve the aforementioned problems, the present inventors provide a transcriptional regulatory sequence comprising a human telomere reverse transcriptase (hTERT) promoter linked to a nucleotide sequence that comprises a c-Myc binding site and/or a Sp1 binding site, and then constructed a recombinant vector, in particular, a recombinant adenoviral vector that carries the transcriptional regulatory sequence.

In one aspect, the present invention involves a transcriptional regulatory sequence comprising an hTERT promoter linked to a nucleotide sequence that comprises one or more c-Myc binding sites and/or one or more Sp1 binding sites.

In another aspect, the present invention provides a recombinant vector comprising a certain gene that is operably linked to the transcriptional regulatory sequence.

In a further aspect, the present invention provides a host cell transformed or transected with the recombinant vector.

In still another aspect, the present invention provides a pharmaceutical composition comprising (a) a therapeutically effective amount of the recombinant vector; and (b) a pharmaceutically acceptable carrier.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows the nucleotide sequence of SEQ ID NO: 13, an m-hTERT promoter according to an embodiment of a transcriptional regulatory sequence of the present invention;

BEST MODE FOR CARRYING OUT THE INVENTION

Figure 2A:
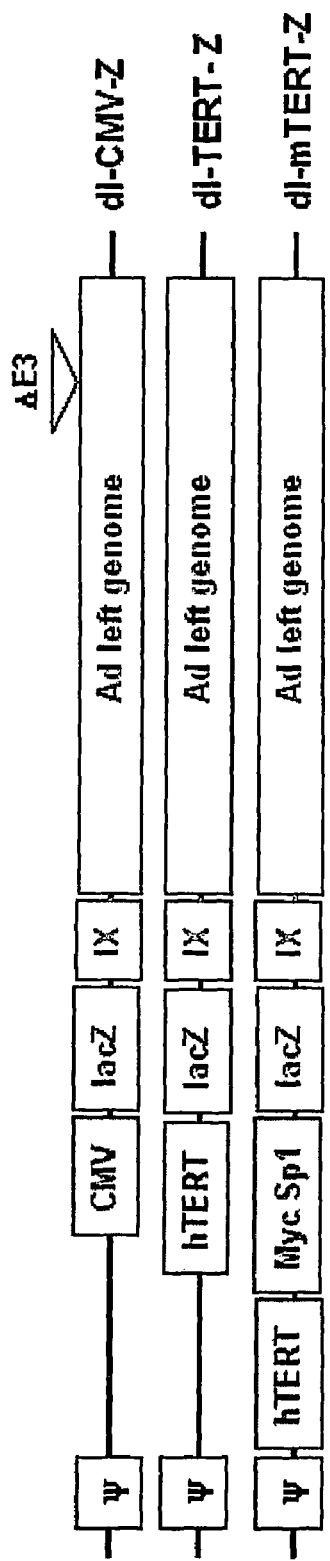
FIG. 2A shows schematic chart of the replication-deficient recombinant adenoviral vectors dl-CMV-Z, dl-TERT-Z and dl-mTERT-Z according to the present invention.

The present invention provides a transcriptional regulatory sequence comprising a human telomere reverse transcriptase (hTERT) promoter linked to a nucleotide sequence that comprises one or more c-Myc binding sites and/or one or more Sp1 binding sites. In one aspect, the present invention provides a transcriptional regulatory sequence comprising an hTERT promoter linked to a nucleotide sequence that comprises a single c-Myc binding site and/or five Sp1 binding sites.

Typically, transcriptional regulatory sequences indicate all sequences regulating transcription of genes operably linked thereto such as promoters and enhancers. However, in the present specification, the transcriptional regulatory sequences are preferably used as promoters, and thus, should be adjacent to each other to regulate transcription of a certain gene. An m-hTERT promoter is provided as an aspect of the transcriptional regulatory sequence according to the present invention.

In the present invention, most preferably, the hTERT promoter is a wild-type hTERT promoter (SEQ ID NO: 1) derived from human genome. Also, as the hTERT promoter, a mammalian-derived TERT (telomere reverse transcriptase) promoter, or a TERT promoter mutated, artificially synthesized within the range maintaining its biological functions may be used. The term "biological functions maintaining functions range" refers to a state at which c-Myc oncogenic protein and Sp1 protein as well as RNA polymerase can bind to any TERT promoter and which is capable of inducing expression of a certain gene operably linked to the TERT promoter. For example, the endogeneous c-Myc binding site or the Sp1 binding site in the hTERT promoter may be replaced by other c-Myc or Sp1 binding sites, which are known in the art.

On the other hand, the hTERT promoter may be easily prepared by a method known in the art, for example, by carrying out PCR using human genome as a template with proper primers, or by using an automatic DNA synthesizer (commercially available from the companies BioSearch, Applied Biosystems, etc.).

The "c-Myc binding site" is an oligonucleotide to which c-Myc oncogenic protein binds, and includes a consensus sequence of cacgtg (SEQ ID NO: 2). All known sequences to which c-Myc oncogenic protein binds may be introduced into the transcriptional regulatory sequence according to the present invention. A plurality of c-Myc binding sites is identified, which includes, for example, cacgcg (SEQ ID NO: 3) and catgcg (SEQ ID NO: 4).

In addition, the "Sp1 binding site" is an oligonucleotide to which Sp1 oncogenic protein binds, and includes a consensus sequence of gggcgg (SEQ ID NO: 5). All known sequences to which Sp1 oncogenic protein binds may be introduced into the transcriptional regulatory sequence according to the present invention. A plurality of Sp1 binding sites are identified, which includes, for example, ccgccc (SEQ ID NO: 6), ctccgcctc (SEQ ID NO: 7), cccagcccc (SEQ ID NO: 8), gggcgg (SEQ ID NO: 5), ggggcgg (SEQ ID NO: 9) and cccccgcccc (SEQ ID NO: 10).

As used herein, the term "consensus sequence" is a nucleotide sequence used to define a family of sequences that are not identical but related to each other. Each position in the consensus sequence shows the nucleotide most frequently found at that position within the family.

In the transcriptional regulatory sequence according to the present invention, the nucleotide sequence comprising one or more c-Myc binding sites and/or one or more Sp1 binding sites may be linked to a 5'-end or a 3'-end of the hTERT promoter, or introduced into the hTERT promoter within the biological functions maintaining range. However, in the present invention, the nucleotide sequence comprising a c-Myc binding site and/or an Sp1 binding site is preferably linked to a 3'-end of the hTERT promoter. On the other hand, linkage of the hTERT promoter with the nucleotide sequence comprising a c-Myc binding site and/or an Sp1 binding site is achieved by ligation at convenient restriction enzyme sites. In case that the restriction enzyme sites are not present, a synthetic oligonucleotide adaptor or linker is used according to a method known in the art.

Since the transcriptional regulatory sequence according to the present invention allows a certain gene operably linked thereto to be expressed with high efficiency in a tumor cell-specific manner, it may be applied to a vector commonly used as a gene vehicle for cancer therapy. Herein, the vector includes viral vectors and non-viral vectors.

Therefore, in an aspect, the present invention provides a recombinant viral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a gene required for viral replication. The viral vector is introduced into tumor cells or normal cells, replicates itself in a cancer cell-specific manner, and eventually kills tumor cells with high efficiency. In addition, in another aspect, the present invention provides a recombinant viral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene. The viral vector includes replication-deficient and replication-competent both. After being introduced into tumor cells or normal cells, the replication-deficient recombinant viral vector may treat cancer by expressing the therapeutic transgene specifically in the tumor cells. In contrast, the replication-competent recombinant viral vector may have an additive antitumor effect by displaying cytolytic effects by both viral replication and expression of the therapeutic transgene. In a further aspect, the present invention provides a recombinant non-viral vector comprising a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene. After being introduced into tumor cells or normal cells, the non-viral vector may treat cancer by expressing the therapeutic transgene specifically in the tumor cells.

As used herein, the term "virus" is used interchangeably with "viral vector", and refers to any of the obligate intracellular parasites having no protein-synthesizing or energy-generating mechanism. The viral genome is RNA or DNA surrounded by a lipid-bilayered coating structure composed of proteins. Examples of the virus useful in the practice of the present invention include baculoviridiae, parvoviridiae, picornoviridiae, herpesviridiae, poxviridae, adenoviridiae and picotinaviridiae. The term "recombinant virus" includes chimeric viruses (or multimer viruses) that are constructed by employing corresponding coding sequences derived from one or more virus subtypes (Feng et al., Nature Biotechnology 15, 866-870).

The term "non-viral vector", as used herein, refers to all vectors commonly used in gene therapy except for the aforementioned viral vectors. Such non-viral vector is exemplified by a variety of plasmids capable of being expressed in eukaryotic cells and liposome.

The term "operably linked", as used herein, refers to a linkage of polynucleotide sequences in a functional relationship. A nucleotide sequence is "operably linked" when it is placed into a functional relationship with another nucleotide sequence. In the present invention, a transcriptional regulatory sequence is operably linked to a coding sequence if it affects the transcription of the coding sequence.

The term "genes required for viral replication", as used herein, refers to all genes comprising viral genome, which are classified into "early genes" and "late genes". The early genes are viral genes that start to be expressed at the early phase of the viral proliferation up to replication of the viral genome taking place, and are involved in the replication of the viral genome. Among the early genes, some are transcribed to RNA molecules by using the host system, whereas others are not transcribed if some early gene products have not been produced in advance. As described above, gradual information expression occurs in the early genes, and, in particular, genes transcribed by host enzymes immediately after the infection are also called "very early genes". The late genes are viral genes that are expressed after replication of viral genome is initiated when a virus infects a host cell. The late genes determine the structure of outer envelope proteins.

The term "therapeutic transgene", as used herein, refers to a nucleotide sequence expression of which in tumor cells produces therapeutic effects. The term therapeutic transgene includes, but is not limited to, tumor suppressor genes, chemokine gene, cytokine gene, antigenic genes, cytotoxic genes, cytostatic genes, apoptotic genes and anti-angiogenic genes.

The term "tumor suppressor gene", as used herein, refers to a nucleotide sequence, the expression of which in a target cell is capable of suppressing the neoplastic phenotype or inducing apoptosis. Examples of the tumor suppressor genes useful in the practice of the present invention include p53 gene, Rb gene, APC gene, DPC-4/Smad4 gene, BRCA-1 gene, BRCA-2 gene, WT-1 gene, retinoblastoma gene (Lee et al., Nature, 1987, 329, 642), MMAC-1 gene, adenomatous polyposis coli protein (Albertsen et al., U.S. Pat. No. 5,783,666), deleted in colon carcinoma (DCC) gene, MMSC-2 gene, NF-1 gene, nasopharyngeal carcinoma tumor suppressor gene that maps at chromosome 3p21.3 (Cheng et al., Proc. Nat'l. Acad. Sci., 1998, USA 95, 3042-3047), MTS1 gene, CDK4 gene, NF-1 gene, NF-2 gene and VHL gene.

The term "antigenic genes", as used herein, refers to a nucleotide sequence, the expression of which in a target cell results in the production of a cell surface antigenic protein capable of recognition by the immune system. Examples of the antigenic genes include carcinoembryonic antigen (CEA), prostate specific antigen (PSA), α-feto protein (AFP), p53 (Levine, A. International Pat. Publication No. WO94/02167). In order to facilitate immune recognition, the antigenic gene may be fused to the MHC class I antigen.

The term "cytotoxic gene", as used herein, refers to a nucleotide sequence, the expression of which in a cell produces a toxic effect. Examples of the cytotoxic genes include nucleotide sequences encoding *Pseudomonas* exotoxin, ricin toxin, diphtheria toxin, and the like.

The term "cytostatic gene", as used herein, refers to a nucleotide sequence, the expression of which in a cell produces an arrest in the cell cycle. Examples of the cytostatic genes include, but are not limited to, p21, retinoblastoma gene, E2F-Rb fusion protein gene, genes encoding cyclin-dependent kinase inhibitors such as p16, p15, p18 and p19, growth arrest specific homeobox (GAX) gene (International Pat. Publication Nos. WO97/16459 and WO96/30385).

The term "cytokine gene", as used herein, refers to a nucleotide sequence, the expression of which in a cell produces a cytokine. Examples of the cytokines include GM-CSF, interleukins (especially, IL-1, IL-2, IL-4, IL-12, IL-10, IL-19 and IL-20), interferon α, β and γ subtypes (especially, interferon α-2b), and fusions such as interferon α-2α-1.

The term "chemokine gene", as used herein, refers to a group of structurally related low-molecular weight cytokines secreted by cells having mitogenic, chemotactic or inflammatory activities. They are primarily cationic proteins of 70 to 100 amino acid residues that share four conserved cysteine residues. These proteins can be sorted into two groups based on the spacing of the two amino-terminal cysteine residues. In the first group, the two cysteine residues are separated by a single residue (Cys-x-Cys), while in the second group, they are adjacent (Cys-Cys). Examples of proteins belonging to the 'Cys-x-Cys' chemokine group include, but are not limited to, platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and I (AMCF-I and -II), pre-B cell growth stimulating factor (PBSF) and IP10. Examples of proteins belonging to the 'Cys-Cys' group include, but are not limited to, monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), eotaxin, I-309, human protein HCC-1/NCC-2, human protein HCC-3, and mouse protein C10.

The term "pro-apoptotic gene", as used herein, refers to a nucleotide sequence, the expression of which results in the programmed cell death of the cell. Examples of the pro-apoptotic genes include p53, adenovirus (Ad) E3-11.6K (derived from Ad2 and Ad5) or adenovirus E3-10.5K (derived from Ad), adenovirus E4 gene, Fas ligand, INF-α, TRAIL, p53 pathway genes, and genes encoding caspases.

The term "anti-angiogenic gene", as used herein, refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (Proc. Nat'l. Acad. Sci. USA, 1998, 95, 8795-8800), and endostatin.

As described above, the transcriptional regulatory sequence according to the present invention may be introduced into a viral vector or a non-viral vector, which are commonly used as a gene vehicle. However, an adenoviral vector is recognized as a suitable gene vehicle, and, practically, has been increasingly used. For this reason, the transcriptional regulatory sequence according to the present invention is suitable to be introduced into an adenoviral vector. Therefore, the present invention provides a recombinant adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene.

The term "replication-competent adenoviral vector", as used herein, refers to an adenoviral vector in which genes essentially required for replication are conserved, and may treat cancer by being replicated in tumor cells and eventually killing the tumor cells. Also, the term "replication-deficient adenoviral vector" refers to an adenoviral vector deleted of genes essentially required for replication, especially, required at the early phase of infection. The replication-deficient adenoviral vector mainly comprises a therapeutic transgene and may treat cancer by expressing the therapeutic transgene in tumor cells. However, as described above, the present invention includes a viral vector comprising a therapeutic transgene as well as being replication-competent. That is, in the present specification, the "replication-deficient adenoviral vector" refers to a replication-deficient adenoviral vector provided as an aspect of the adenoviral vector comprising a therapeutic transgene.

As used herein, the terms "adenovirus" and "adenoviral vector" are interchangeably used, and refer to viruses belonging to the genus Adenoviridae. The term "Adenoviridae" refers collectively to animal adenoviruses of the genus Mastadenovirus including, but not limited to, human, bovine, ovine, equine, canine, porcine, murine and simian adenovirus subgenera. In particular, human adenoviruses include the A-F subgenera as well as the individual serotypes thereof. The A-F subgenera include, but are not limited to, human adenovirus types 1, 2, 3, 4, 4a, 5, 6, 7, 8, 9, 10, 11 (Ad 11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48 and 91. In a desirable aspect of the present invention, the adenovirus is derived from a human adenovirus of serotype 2 or 5.

The adenoviral genome slightly differs according to adenoviral serotypes, but is typically composed of early genes of E1A, E1B, E2, E3 and E4 and late genes of L1, L2, L3, L4 and L5. In the early genes, the E1A gene is expressed prior to other viral genes immediately after viral infection (0-2 hrs). E1A protein serves as a transcriptional regulatory factor and is essentially required for expression of other early genes. The deletion of the E1A gene results in no production of gene products needed for viral DNA replication, and eventually leads to no further infection. E1B protein is essential for the transport of late gene mRNA transcripts to the cytosol from the nucleus. The defect in expression of E1B expression leads to the weak expression of viral late genes and incomplete blocking of protein synthesis of host cells. The E4 gene encodes several transcriptional products. The open reading frames (ORFs) 3 and 6 of the E4 transcriptional unit increase accumulation of major late transcriptional unit mRNAs by binding to the E1B-55kD protein and the E2F-1/DR-1 heterodimer. In case of bearing lesions in both proteins of the E4 ORFs 3 and 6, mutant viruses form plaques with an efficiency less than $10^{-6}$ that of wild-type virus. The late genes including L1, L2, L3, L4 and L5 encode structural proteins of adenovirus.

Both early and late genes are required for effective replication of adenovirus. Therefore, in an aspect, the present invention includes an adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to one or more genes of early genes and late genes of adenovirus. In particular, among the early and late genes, since the early genes are involved in replication of viral genome, in a preferred aspect, the present invention provides an adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to one or more genes of early genes of adenovirus. Among the early genes, in particular, the E1A gene serves as a transcriptional factor inducing expression of other viral genes and is thus the most important element in the viral replication. Therefore, the present invention provides a recombinant adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to an adenovirus E1A gene.

The recombinant adenoviral vector comprising the transcriptional regulatory sequence operably linked to a gene required for adenoviral replication according to the present invention is introduced into tumor cells harboring telomerase activated in the presence of the c-Myc oncoprotein or the Sp1 protein, proliferates itself with high efficiency and eventually kills the tumor cells. In contrast, in case of being introduced into normal cells, the adenoviral vector is rarely capable of proliferating and thus does not affect the normal cells.

In a more preferred aspect involved in a recombinant adenoviral vector having the effect of killing tumor cells by viral replication, a recombinant adenoviral vector having a deletion in E1B-19kD gene is used. E1B-19kDa protein, which is a potent apoptosis inhibitor, is known to inhibit apoptosis mediated by the adenovirus early gene product, E1A protein, as well as inhibiting apoptosis induced by p53 in tumor cells. Also, the functional similarity between E1B-19 kDa and Bcl-2 is found in that both suppress apoptosis induced by the removal of growth factor, radiotherapy or antitumor agents. Therefore, an E1B-19kD gene-deleted recombinant adenovirus has excellent tumor cell-killing effect and a spread oncolytic effect to surrounding tumor cells, by inducing cell lysis by viral proliferation as well as apoptosis in adenovirus-infected cells. Thus, due to its high-efficiency proliferation in a tumor cell-specific manner, the recombinant adenoviral vector may be more effective in killing selectively tumor cells.

In addition to having the tumor cell-killing effect by adenoviral proliferation, the adenoviral vector may treat cancer by carrying a therapeutic transgene by a gene cloning technique and being then expressed in tumor cells. Therefore, the present invention provides a recombinant adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene. The therapeutic transgene is expressed with high efficacy specifically in tumor cells whereas being incapable of being expressed in normal cells, and thus does not have cytotoxicity or side effects in normal cells.

The E1 or E3 gene of the adenovirus genome is typically deleted and replaced by a therapeutic transgene. Therefore, the present invention provides a replication-deficient recombinant adenoviral vector comprising the transcriptional regulatory sequence that is operably linked to a therapeutic transgene introduced in place of the adenovirus E1 gene. This recombinant adenoviral vector is replication-deficient due to the deletion of the E1 gene essential for viral replication, and may treat tumor by expressing the therapeutic transgene. In addition, in another aspect, the present invention provides a replication-competent recombinant adenoviral vector comprising the transcriptional regulatory sequence that is operably linked to a therapeutic transgene introduced in place of the adenovirus E3 gene. This recombinant adenoviral vector is capable of replicating and thus has an additive antitumor effect by displaying cytolytic effects by both viral replication and expression of the therapeutic transgene. However, since adenoviruses having deletions in both E1 and E3 genes has gene transfer efficiency greatly higher than other vectors and expresses transgenes in a broad spectrum of cell types, in a preferred aspect, an adenovirus is an E1/E3-deleted replication-incompetent adenovirus. Therefore, the present invention provides an E1/E3-deleted recombinant adenoviral vector comprising the transcriptional regulatory sequence that is operably linked to a therapeutic transgene introduced in place of the adenovirus E1A gene.

To prepare the aforementioned recombinant vectors on a large scale, each recombinant vector should be introduced into a suitable host cell. Therefore, the present invention provides a host cell transformed or transfected with the recombinant viral vector. The preferred methods for the introduction of the vector into a host cell include, for example, calcium phosphate transfection, DAEA-dextran mediated transfection, transfection, microinjection, cationic lipid-mediated transfection, electroporation, transduction, scrape loading, ballistic introduction and infection. On the other hand, the host cell may be selected depending on the recombinant vectors, and desirable host cells are known in the art.

In the present invention, a recombinant adenoviral vector is produced by constructing a shuttle vector carrying a transcriptional regulatory sequence comprising an hTERT promoter linked to a nucleotide sequence that comprises a c-Myc binding site or an Sp1 binding site, obtaining a recombinant adenovirus plasmid through homologous recombination between the shuttle vector and an adenoviral vector, and transforming or transfecting a suitable cell with the recombinant adenovirus plasmid.

A plasmid used for the construction of the shuttle vector, carrying a transcriptional regulatory sequence comprising an hTERT promoter linked to a nucleotide sequence that comprises a c-Myc binding site or an Sp1 binding site, may be prokaryotic or eukaryotic which is known in the art or commercially available. In addition, the host cell for a recombinant plasmid, used for the production of a recombinant adenovirus, is well known to those skilled in the art, and exemplified by human embryo kidney cell line 293 (E1A/B+) transformed with a nucleotide sequence nt 1-4344 encoding Ad5, and human embryo retinoblastoma cell 911 containing a nucleotide sequence nt 79-5789 of Ad5.

The recombinant viral vector or non-viral vector according to the present invention has high-efficacy killing effect specifically against various tumor cells, especially, tumor cells expressing high level telomerase, including liver cancer, lung cancer, cervical cancer and brain cancer. Therefore, the present invention is intended to provide a pharmaceutical composition comprising the recombinant viral or non-viral vector as an active component.

The present invention provides a pharmaceutical composition comprising (a) a therapeutically effective amount of a recombinant viral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a gene required for viral replication; and (b) a pharmaceutically acceptable carrier. Since the recombinant viral vector contained in the pharmaceutical composition of the present invention, as described above, has oncolytic effects against a variety of tumor cells, the pharmaceutical composition is useful in treating various diseases and tumor-related diseases, including stomach cancer, lung cancer, ovarian cancer, liver cancer, bronchogenic cancer, nasopharyngeal cancer, laryngeal cancer, pancreatic cancer, bladder cancer, colon cancer, and cervical cancer.

The present invention provides a pharmaceutical composition comprising (a) a therapeutically effective amount of a recombinant viral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene; and (b) a pharmaceutically acceptable carrier. Since the therapeutic transgene introduced into the recombinant viral vector is expressed in tumor cells, such a pharmaceutical composition is useful in treating diverse types of cancer, for example, melanoma, breast cancer, lung cancer, neuroblastoma, renal cell carcinoma, ovarian cancer, brain cancer, head and neck cancer and mesothelioma.

As an ideal aspect involved in the aforementioned pharmaceutical composition, a viral vector is an adenoviral vector. Therefore, the present invention provides a pharmaceutical composition comprising (a) a therapeutically effective amount of a recombinant adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a gene required for viral replication; and (b) a pharmaceutically acceptable carrier. In addition, the present invention provides a pharmaceutical composition comprising (a) a therapeutically effective amount of a recombinant adenoviral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene; and (b) a pharmaceutically acceptable carrier.

The present invention provides a pharmaceutical composition comprising (a) a therapeutically effective amount of a non-viral vector with a transcriptional regulatory sequence comprising an hTERT promoter linked to a nucleotide sequence that comprises one or more c-Myc binding sites and/or one or more Sp1 binding sites, wherein the transcriptional regulatory sequence is operably linked to a therapeutic transgene; and (b) a pharmaceutically acceptable carrier.

The term "treatment", as used herein, refers to a perfect cure, suppression or alleviation of diseases or disorders. Therefore, the term "therapeutically effective amount", as used herein, means an amount sufficient to achieve the above pharmaceutical effect.

The pharmaceutically acceptable carrier contained in the present composition, which is commonly used in pharmaceutical formulations, but is not limited to, includes lactose, dextrose, sucrose, sorbitol, mannitol, starch, rubber arabic, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils. The pharmaceutical composition of the present invention may further include a lubricant, a humectant, a sweetener, a flavoring agent, an emulsifier, a suspending agent and a preservative.

The pharmaceutical composition of the present invention may be administered using the conventional methods commonly used in gene therapy, and preferably, administered parenterally, i.e., by intravenous, intraperitoneal, intramuscular, subcutaneous, or local administration. For example, the pharmaceutical composition may be administered intraperitoneally to treat ovarian cancer and intravenously to treat liver cancer, directly injected into a visible tumor mass to treat breast cancer and head and neck cancer, directly injected to enema to treat colon cancer, and directly injected to a catheter to treat bladder cancer. In the present invention, intravenous administration, intraperitoneal administration or administration into tumor mass is particularly preferred.

A suitable dosage of the pharmaceutical composition of the present invention may vary depending on pharmaceutical formulation methods, administration methods, the patient's age, body weight, sex, pathogenic states and diet, administration time, administration route, and an excretion rate of and sensitivity for a used pharmaceutical composition, and doctors of ordinary skill in the art can determine an effective amount of the pharmaceutical composition for desired treatment. Generally, the pharmaceutical composition of the present invention comprises $1\times10^5$ to $1\times10^{15}$ PFU/ml of a recombinant adenovirus, and $1\times10^{10}$ PFU of a recombinant adenovirus is typically injected once every two days for two weeks.

The pharmaceutical composition comprising a recombinant vector according to the present invention may be formulated into a unit dose formulation using a pharmaceutically acceptable carrier and/or excipient, or a multidose formulation by being contained in a multidose container. The pharmaceutical composition may be formulated into extracts, powder, granules, tablets or capsules, and further include a dispersion agent or a stabilizer, and the pharmaceutical composition may be solutions of oil or aqueous medium, suspensions or emulsions.

The pharmaceutical composition comprising a recombinant vector according to the present invention may be utilized alone or in combination with typical chemotherapy or radiotherapy. Such combination therapy may be more effective in treating cancer. The chemotherapeutic agent useful for the combination therapy include cisplatin, carboplatin, procarbazine, mechlorethamine, cyclophosphamide, ifosfamide, melphalan, chlorambucil, busulfan, nitrosourea, dactinomycin, daunorubicin, doxorubicin, bleomycin, plicamycin, mitomycin, etoposide, tamoxifen, taxol, transplatinum, 5-fluorouracil, vincristine, vinblastin and methotrexate. Examples of the radiotherapy useful for the combination therapy include X-ray illumination and γ-ray illumination.

In order to increase stability at room temperature, reduce the need for high-cost storage at low temperature, and prolong shelf-life, the pharmaceutical composition comprising a recombinant vector according to the present invention may be lyophilized. A process for freeze-drying may comprise the steps of freezing, first drying and second drying. After freezing, the composition is heated under pressure to evaporate vapor. At the second drying step, residual water is removed from the dry product.

In an aspect, freeze-drying of the pharmaceutical composition according to the present invention may be achieved according to the following steps: (1) determining collapse temperature of the pharmaceutical composition through a free-drying microscopic analysis (Pikal, M. J., et al., hit. J. Pharm. 62, 165-186, 1990); (2) placing a vial on the shelf of a freeze-drier at room temperature and then equilibrating it for about 30 min at $-1°$ C.; (3) cooling the shelf to $-55°$ C. and then maintaining it at $-55°$ C. for 2 hrs; (4) performing a first drying at about $-32°$ C. of product temperature or $5°$ C. lower temperature than the collapse temperature; (5) performing a second drying at $35°$ C. under pressure of 55 to 120 mmHg; and (6) covering the vial with the lid under vacuum condition of the freeze-drier, and storing it at 2 to $8°$ C. after crimp-sealing.

The freeze-dried pharmaceutical composition may include an excipient and a lyoprotectant. Non-limiting examples of the excipient include a buffer solution containing 0.9% NaCl and 10 mM sodium phosphate (pH 7.0) or 10 mM sodium citrate (pH 7.0). The lyoprotectant functions to protect biological molecules contained the composition during the freeze-drying, and supply mechanical support to the final product, which is exemplified by PBS (pH 7.0), and PBS/4%, 12% or 15% trehalose.

The present invention will be explained in more detail with reference to the following examples in conjunction with the accompanying drawings. However, the following examples are provided only to illustrate the present invention, and the present invention is not limited to them.

EXAMPLE 1

Selection of Tumor Cell Lines and Normal Cell Lines and Cell Culturing

The following cell lines were used in the present invention: tumor cell lines: human hepatoma cell lines (SK-Hep1, Hep3B and HepG2), human glioma cell lines (U251N and U343), human lung carcinoma cell lines (A549 and H460), human cervical carcinoma cell lines (C33A and HeLa), and human breast cancer cell lines (MCF7); and human normal cells: 173We, CBHEL, MRC5, WI38, IMR90 and BJ. All cell lines were purchased from American Type Culture Collection (ATCC), and cultured in an incubator at $37°$ C. under 5% $CO_2$ in DMEM medium supplemented with 10% fetal bovine serum (GIBCO BRL, NY) and penicillin/streptomycin (GIBCO BRL, NY).

EXAMPLE 2

Assay for Endogenous Telomerase Activity in the Cell Lines

Endogenous telomerase activity was measured in each cell line using a TRAPEZE ELISA (enzyme linked immunosorbent assay) telomerase assay kit (Oncor, Gaithsberg, Md.) according to the direction by the manufacturer, as follows. First, $1\times10^6$ cells were lysed with 200 μl of a pre-cooled cell lysis solution and centrifuged at 10,000×g for 15 min. Immediately after the centrifugation, the cell extract was stored at $-80°$ C. Protein concentrations were determined using a protein assay kit (Bio-Rad, Hercules, Calif.). Then, the samples with an equal protein concentration were evaluated for telomerase activity by a telemetric repeat amplification protocol (TRAP) assay. A 50-μl reaction mixture was prepared by mixing 100 ng of each cell extract with 10 μl of 5×TRAP reaction mix and 2 units of Taq polymerase. After being preincubated at room temperature for 30 min for TRAP extension, the reaction mixture was subjected to PCR. PCR conditions included 33 cycles of 30 sec at $94°$ C. and 30 sec at $55°$ C. To analyze telomerase activity of each sample, absorbance was measured at 450 nm and 650 nm by ELISA. All tests were repeated more than three times, and the mean values were calculated.

Figure 3:
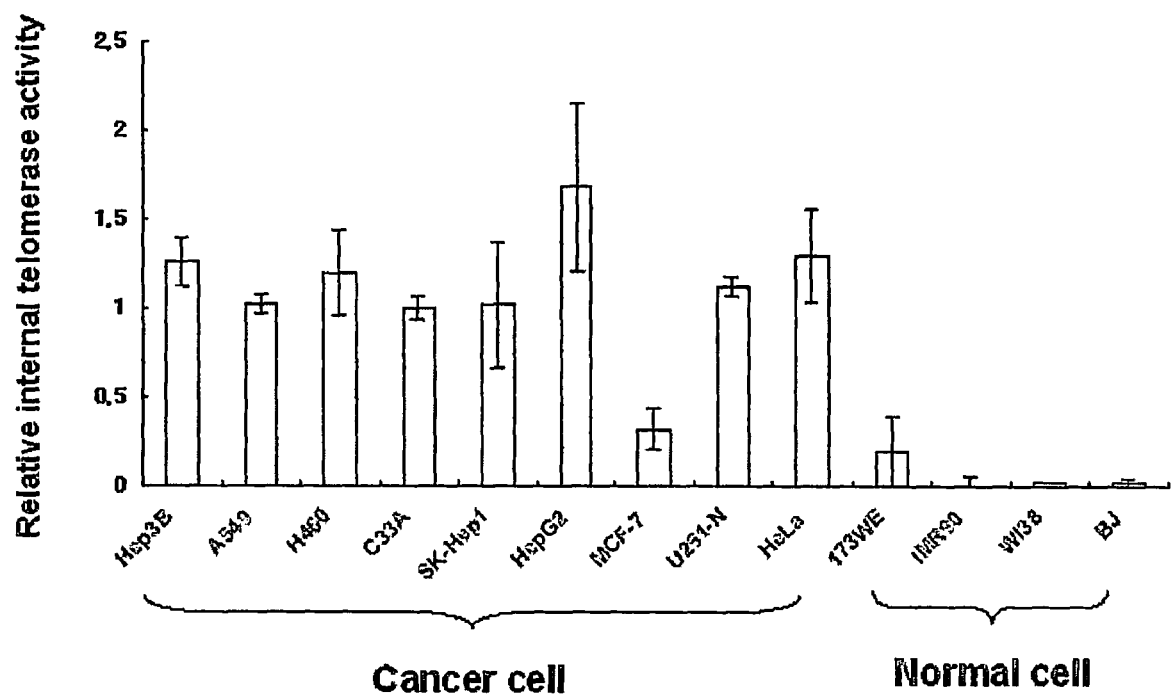
FIG. 3 is a graph showing relative activity of endogenous telomerase in various tumor cell lines and normal cell lines.

As shown in FIG. 3, all tumor cell lines except for the MCF-7 breast cancer cell line, that is, the human hepatoma cell lines (SK-Hep1, Hep3B and HepG2), the human lung carcinoma cell lines (A549 and H460), the human cervical carcinoma cell lines (C33A and HeLa) and the human glioma cell line (U251N), displayed high telomerase activity. In contrast, telomerase activity was rarely detected in the normal cell lines 173We, BJ, IMR90 and WI38.

EXAMPLE 3

Preparation of hTERT Promoter and m-hTERT Promoter

In order to obtain wild-type hTERT promoter (also referred to simply as 'hTERT promoter'), human genomic DNA was isolated from normal MRC 5 cells, derived from human lung tissue. For amplification of hTERT promoter containing two c-Myc binding sites and five Sp1 binding sites, PCR was carried out using the human genomic DNA as a template and a primer set: a sense primer 5'-cccaaagcttaggccgattc gagatctctcc-3' (SEQ ID NO: 11) containing a PvuII site (underlined) for convenience of cloning; and a an anti-sense primer 5'-gaattcaagcttcgeggggtggccggggcc-3' (SEQ ID NO: 12) containing an EcoRI site and a HindIII site (underlinded). The 447 bp PCR product was treated with BglII and HindIII, and inserted into a pSEAP-basic vector (Clontech, Palo Alto, Calif.) expressing alkaline phosphatase, thus giving a pSEAP-TERT plasmid.

In order to prepare m-hTERT promoter (SEQ ID NO: 13; and see, FIG. 1) comprising hTERT promoter further containing one c-Myc binding site and five Sp1 binding sites, the wild-type hTERT promoter containing two c-Myc binding sites and five Sp1 binding sites was linked to an hTERT promoter containing one c-Myc binding site and five Sp1 binding sites, as follows. A pGL2-hTERT vector containing one c-Myc binding site and five Sp1 binding sites was digested with EcoRI and HindIII. The excised hTERT promoter fragment was inserted into the pSEAP-TERT vector digested with the same restriction enzymes, thus giving a pSEAP-mTERT plasmid.

EXAMPLE 4

Preparation and Production of Recombinant Adenoviruses

A. Preparation and Production of Replication-Deficient Recombinant Adenoviruses dl-CMV-LacZ, dl-TERT-Z and dl-mTERT-Z In order to prepare an E1 adenovirus shuttle vector containing a LacZ gene expression of which was under CMV promoter control, pcDNA-hygro-LacZ expressing LacZ (expression of the LacZ gene was under CMV promoter control) was digested with HindIII and NaeI, and the fragment of CMV promoter-LacZ-polA site was inserted into an E1 adenovirus shuttle vector pΔE1 SP1A, thus yielding a pΔE1SP1A/CMV-lacZ shuttle vector.

To prepare vectors carrying a LacZ gene expression of which was under the hTERT promoter and the m-hTERT promoter control, first, the pSEAP-TERT and pSEAP-mTERT plasmids were digested with BglII and EcoRI. The excised hTERT promoter and m-hTERT promoter fragments were treated with BamHI and EcoRI, and individually inserted into a pΔE1SP1A/LacZ prepared by excising out the CMV promoter from the pΔE1SP1A/CMV-lacZ, thus yielding pΔE1SP1A/TERT-LacZ and pΔ1SP1A/mTERT-LacZ shuttle vectors, respectively.

The prepared shuttle vectors were digested with XmnI. Then, E. coli BJ5183 was co-transfected with each of the shuttle vectors along with an adenovirus dl324BstB1 (a gift from Ph. Verca in the university of Fribourgh, Swiss) linearized by BstBI digestion to induce homologous recombination between the two vectors. The homogeneously recombinant plasmid DNA was digested with PacI, and introduced into 293 cells to produce recombinant adenoviruses dl-CMV-Z, dl-TERT-Z and dl-mTERT-Z (FIG. 2A). The produced recombinant adenovirus dl-mTERT-Z was deposited in the Korean Culture Center of Microorganisms (KCCM) with accession No. KCCM-10471 in Feb. 20, 2003.

B. Preparation and Production of Replication-Competent Recombinant Adenoviruses Ad-TERT-Δ19 and Ad-mTERT-Δ19

In order to prepare adenoviruses replication of which was regulated by each of the hTERT promoter and m-hTERT promoter, an E1B-19kD-deleted replication-competent adenovirus Ad-ΔE1B19 was used as a template adenovirus plasmid. First, the pSEAP-TERT and pSEAP-mTERT plasmids were digested with BglII and EcoRI. The excised hTERT promoter and m-hTERT promoter fragments were treated with BamHI and EcoRI, and individually inserted into a BamHI/EcoRI-digested pΔE1SP1A/ΔE1B19, thus generating pΔE1SP1A/hTERT-ΔE1B19 and pΔE1SP1A/mTERT-ΔE1B19 shuttle vectors, respectively.

Figure 2B:
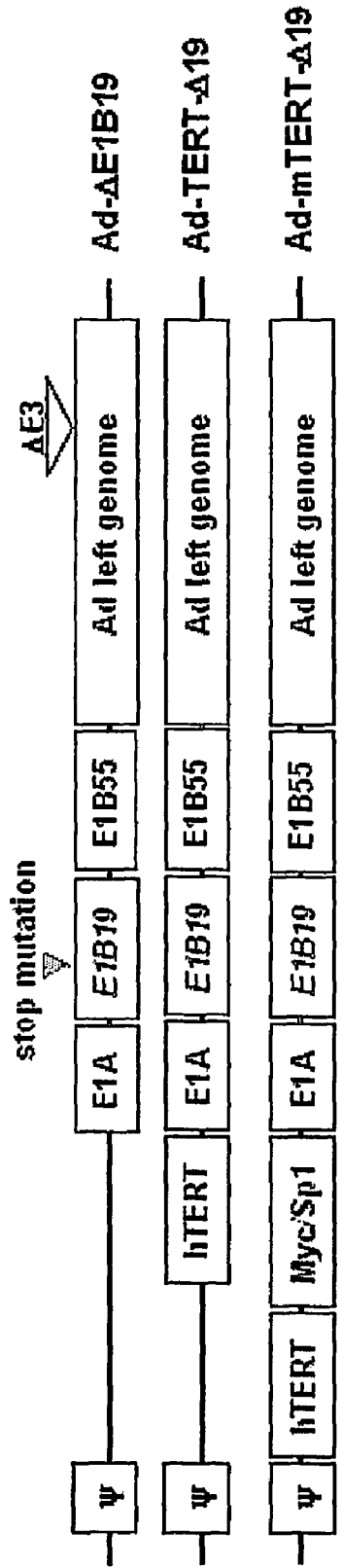
FIG. 2B shows schematic chart of the replication-competent recombinant adenoviral vectors Ad-ΔE1B19, Ad-TERT-Δ19 and Ad-mTERT-Δ19 according to the present invention.

The prepared shuttle vectors were digested with XmnI. Then, E. coli BJ5183 was co-transfected with each of the shuttle vectors along with an Ad-ΔE1B19 linearized by BstBI digestion to induce homologous recombination between the two vectors, thus generating Ad-TERT-Δ19 and Ad-mTERT-Δ19 replication-competent adenoviruses, respectively (FIG. 2B). Production, concentration and determination of viral titer of the recombinant adenoviruses were performed in the 293 cell line. The produced recombinant adenovirus Ad-mTERT-Δ19 was deposited in the Korean Culture Center of Microorganisms (KCCM) with accession No. KCCM-10470 in Feb. 20, 2003.

EXAMPLE 5

Examination of Gene Expression Patterns of Replication-Deficient Recombinant Adenoviruses In order to determine whether gene expression under the hTERT promoter or the m-hTERT promoter control was associated with the activity of intracellular telomerase, LacZ gene expression patterns were examined in tumor cell lines using the replication-deficient recombinant adenoviruses dl-CMV-Z, dl-TERT-Z and dl-mTERT-Z, which carried a LacZ marker gene. Tumor cell lines (C33A, U251N and MCF-7) and normal cell lines (WI38 and 173We) were individually aliquotted onto 24-well plates at a density of $2\times10^5$ cells per well, and infected with the β-galactosidase-expressing adenoviruses dl-CMV-Z, dl-TERT-Z or dl-mTERT-Z at a multiplicity of infection (MOI) of 50. After two days, the cells were stained with X-gal. β-galactosidase (β-gal) expression was examined by X-gal assay. In brief, the cells were fixed in a fixation solution (1% formaldehyde, 0.2% glutaraldehyde, in $H_2O$) for 5 min, and incubated in a staining solution (0.4 mg/ml X-gal, 4 mM potassium ferricyanide, 4 mM potassium ferrocyanide, 2 mM $MgCl_2$, in PBS) at 37° C. for 4-16 hrs.

Figure 4:
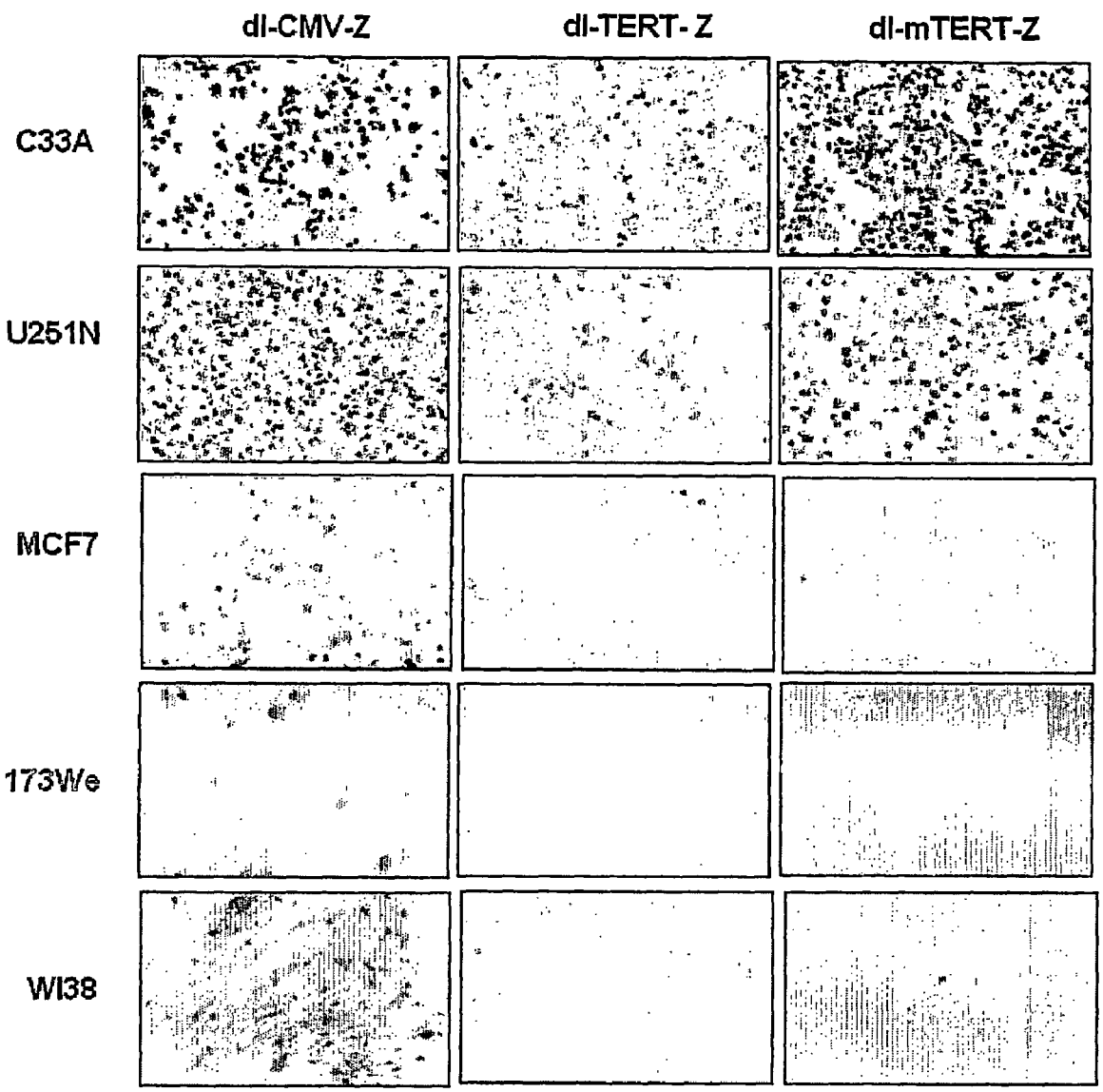
FIG. 4 is a photograph showing expression patterns of a LacZ gene of the replication-deficient recombinant adenoviral vectors dl-CMV-Z, dl-TERT-Z and dl-mTERT-Z according to the present invention in various tumor cell lines and normal cell lines.

As shown in FIG. 4, when all of the tested cell lines were infected with the dl-CMV-Z, they were highly positive for the expression of the LacZ gene product β-galactosidase, regardless of intracellular telomerase activity. These results indicate that the CMV promoter lacks tumor-specificity. However, when the tested cell lines were infected with the dl-TERT-Z or the dl-mTERT-Z, respectively carrying the hTERT promoter and the m-hTERT promoter, which were capable of regulating gene expression in a tumor cell-specific manner, β-galactosidase expression was detected in only cell lines with high telomerase activity. These results defined that the hTERT and m-hTERT promoters were tumor-specific promoters. In particular, in the cell lines with high telomerase activity (C33A and U251N), in comparison with the case in that the LacZ gene was under the hTERT promoter, β-galactosidase was expressed at higher levels when the LacZ gene was under the control of the m-hTERT promoter further containing one c-Myc binding site and five Sp1 binding sites, indicating that the m-hTERT promoter has higher promoter activity than the hTERT promoter. Also, in the cell lines with low telomerase activity (MCF-7, 173We and WI38), β-galactosidase expression was significantly reduced in the case of infection with the dl-mTERT-Z, indicating that the m-hTERT promoter has excellent tumor-specificity.

The hTERT and m-hTERT promoters according to the present invention were quantitatively evaluated for gene expression efficacy and tumor-specificity. After the dl-CMV-Z, dl-TERT-Z and dl-mTERT-Z adenoviruses infected several tumor cell lines and normal cell lines at various titers for two days, the cells were lysed and β-gal activity was measured. Tumor cell lines (H460, A549, C33A, SK-Hep1, HepG2, Hep3B, U343, U251N and MCF7) and normal cell lines (173WE, CBHEL, MRC5, IMR90, W138 and BJ) were individually aliquotted onto 24-well plates at a density of $2\times10^5$ cells per well, and infected with the dl-CMV-Z, dl-TERT-Z or dl-mTERT-Z adenoviruses at MOIs of 10, 50 and 100. β-gal activity was measured by the Cheng and Baltimore's method (Cheng, G. et al. 'A co-inducer with TRAF2 of TNF- and CD40L-NK-kappaB activation.' Genes & Develop., 1996, 10, 963-973.). In brief, after the culture medium was removed from each well, the cells were detached using Z buffer (60 mM $Na_2HPO_4$, 40 mM $NaH_2PO_4$, 10 mM KCl, 1 mM $MgSO_4$, 50 mM β-mercaptoethanol). $1\times10^6$ cells were lysed with 100 µl of cell lysis buffer (β-mercaptoethanol-free Z buffer+1% NP-40) supplemented with protease inhibitors (20 µM PMSF, 20 µM TLCK, 20 µM TPCK). After each of the cell lysates was centrifuged, 30 µl of the supernatant was aliquotted onto 96-well plates. 120 µl of an ONPG solution, prepared by dissolving 4 mg ONPG in 6 ml of the Z buffer, was added to each well, and the plates were incubated at 37° C. for 30 min. Absorbance was measured at 420 nm.

Figure 5A:
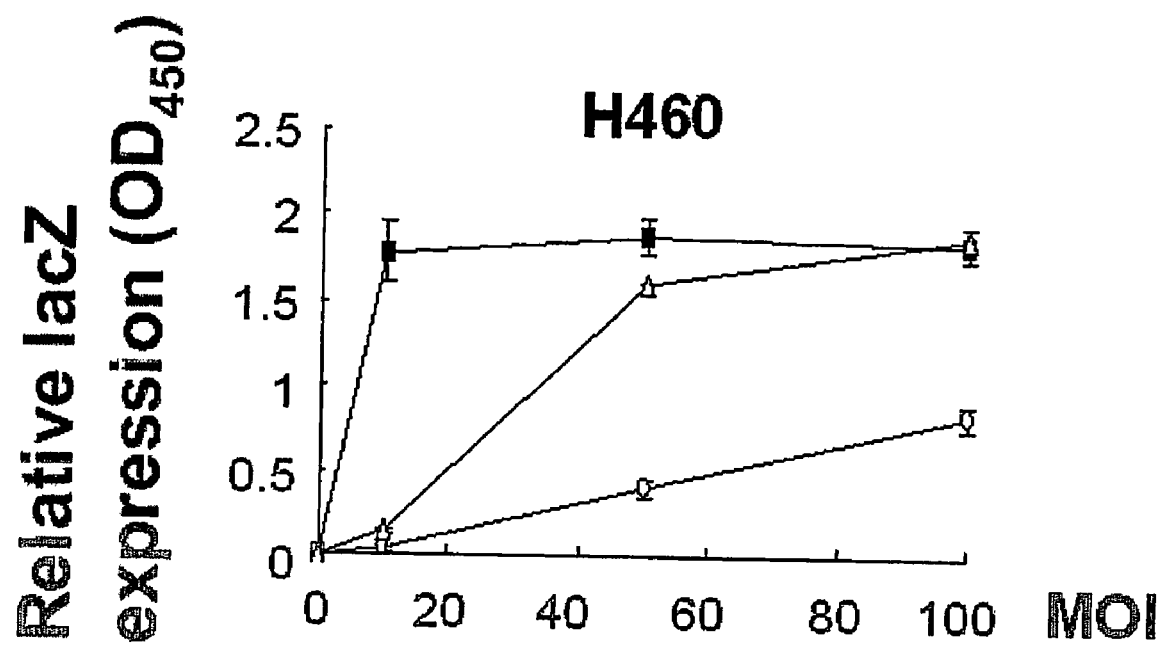
FIG. 5A is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (H460)
Figure 5B:
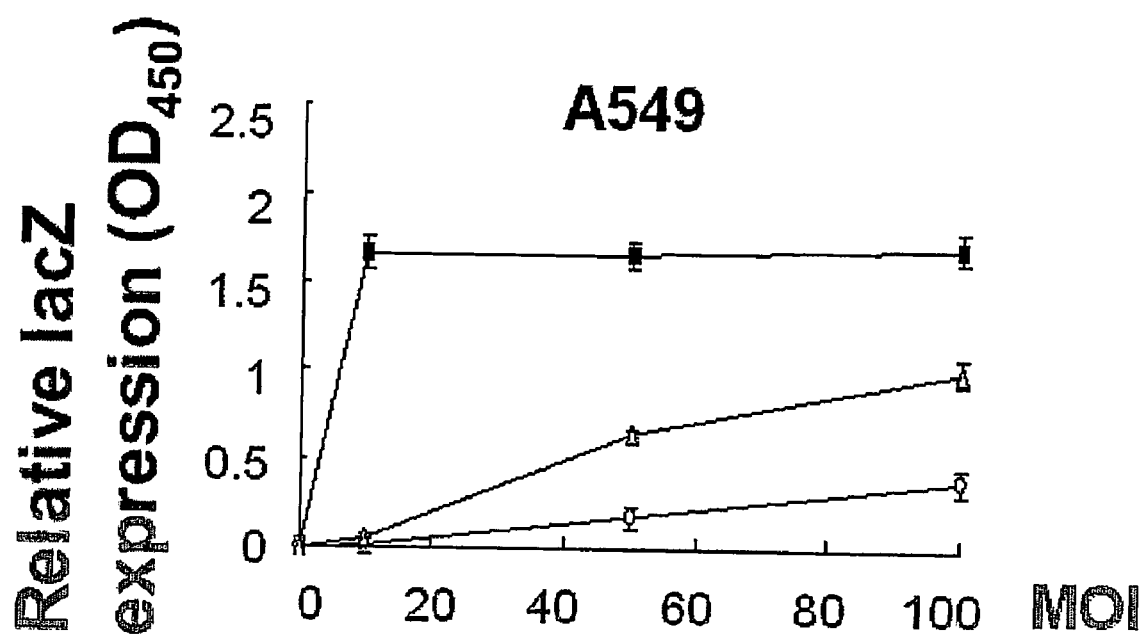
FIG. 5B is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (A549)
Figure 5C:
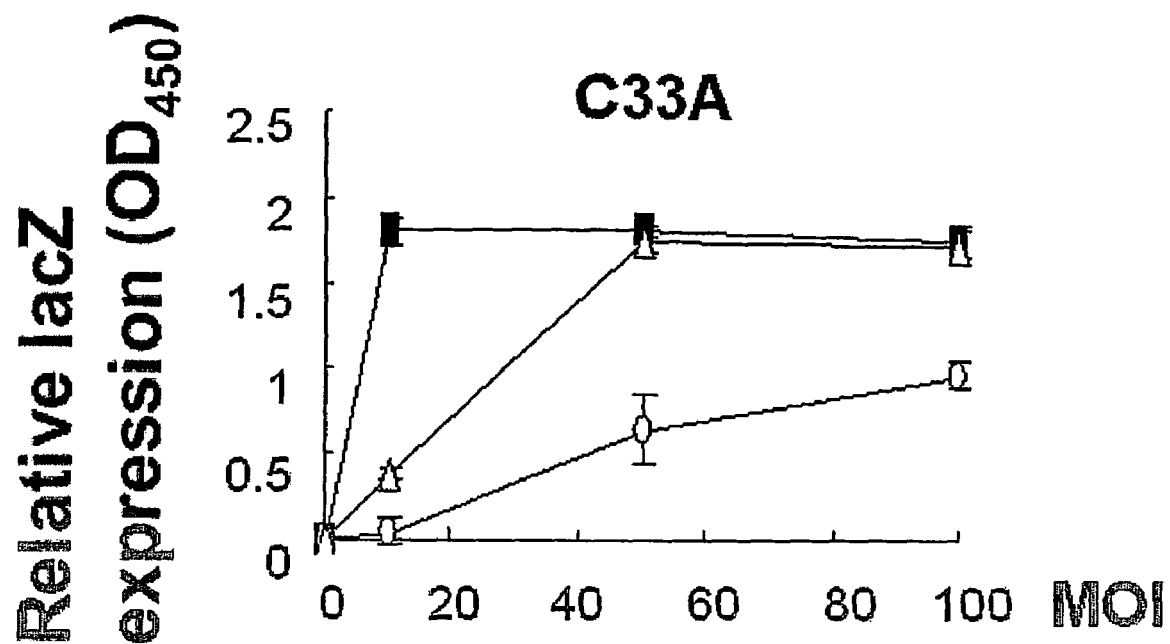
FIG. 5C is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (C33A)
Figure 5D:
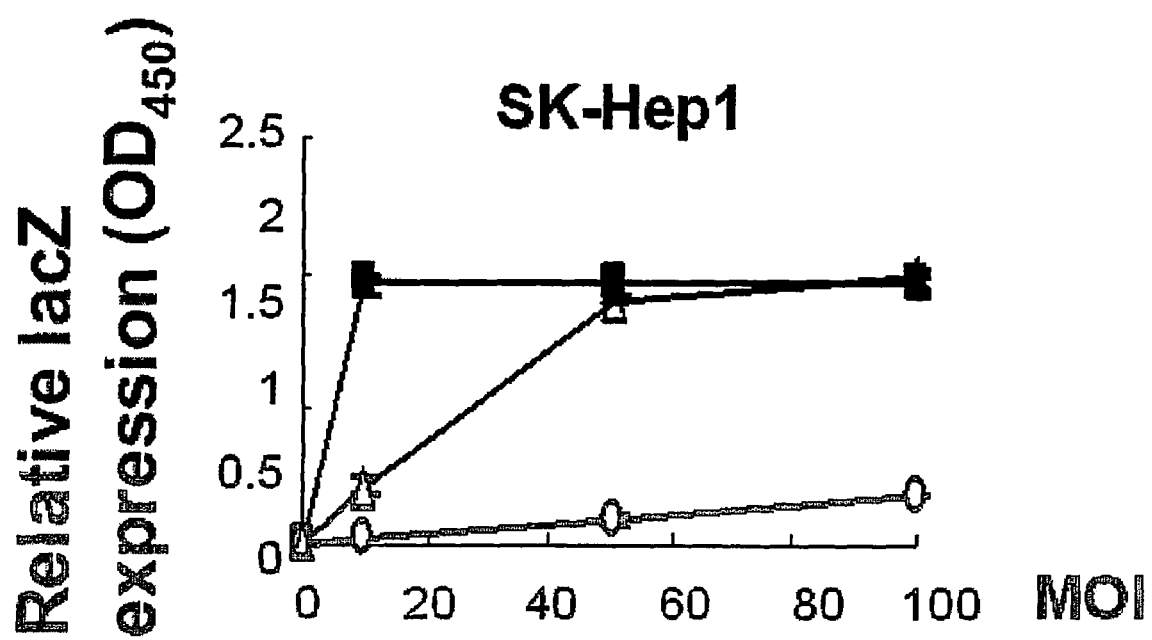
FIG. 5D is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (SK-Hep1)
Figure 5E:
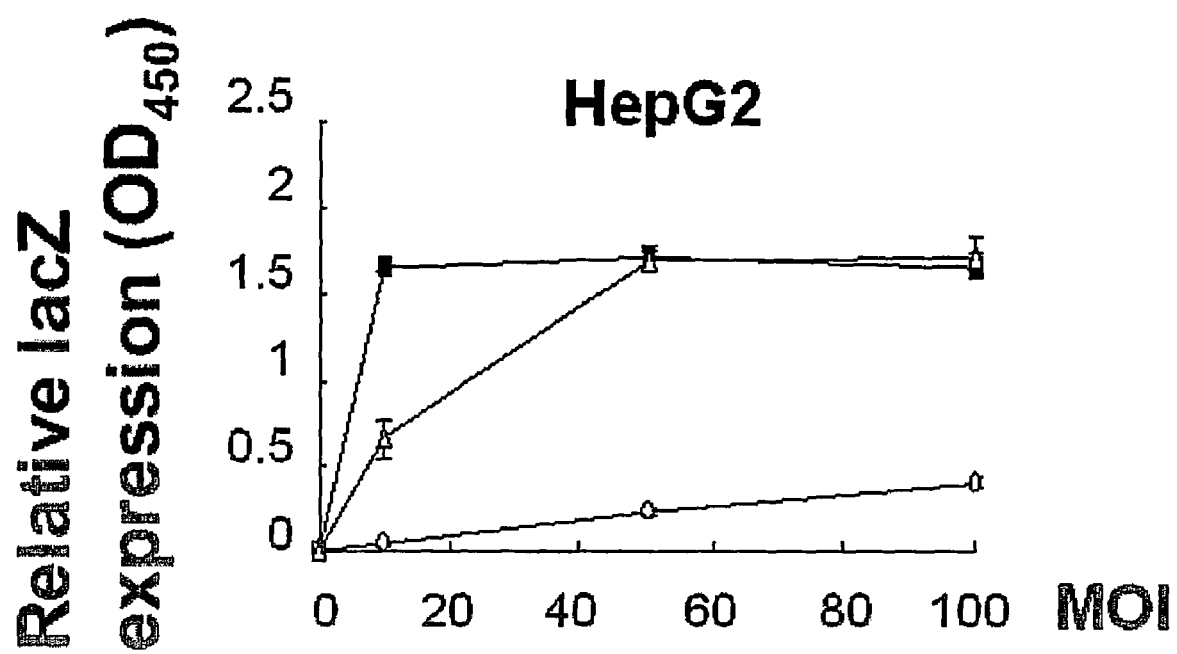
FIG. 5E is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (HepG2)
Figure 5F:
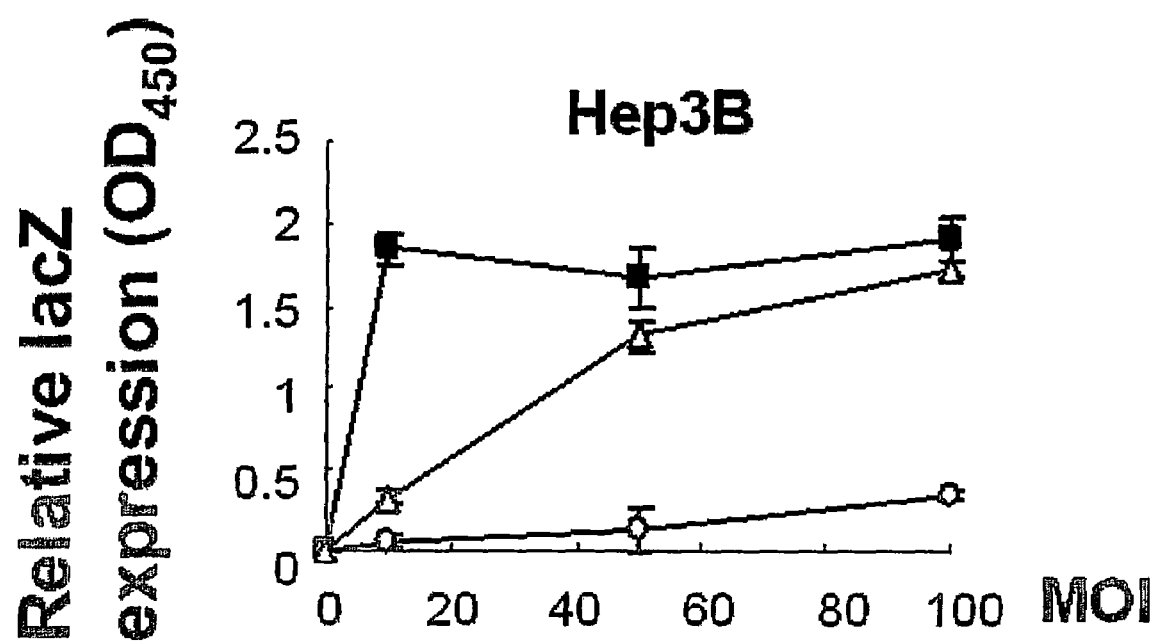
FIG. 5F is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (Hep3B)
Figure 5G:
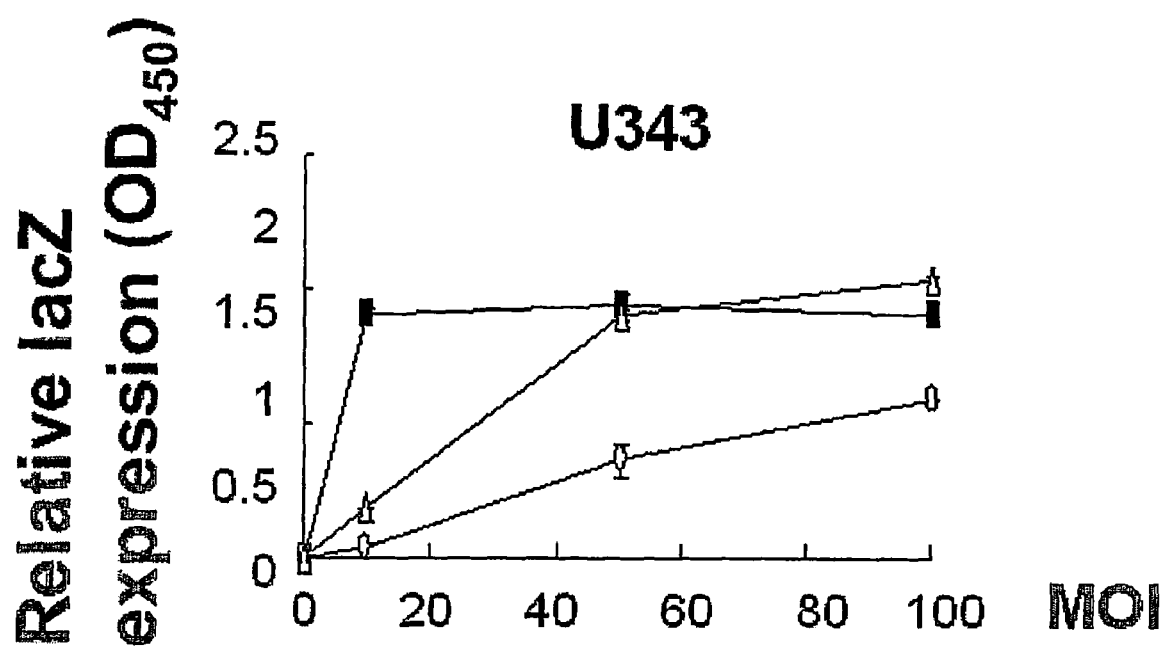
FIG. 5G is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (U343)
Figure 5H:
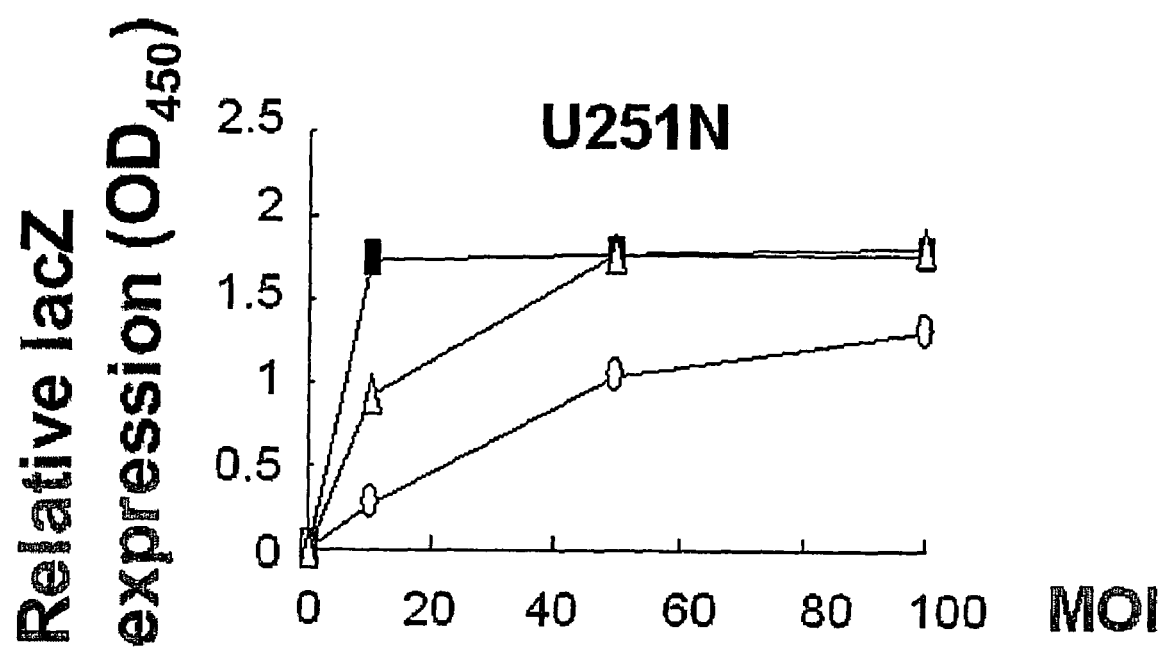
FIG. 5H is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (U251N)
Figure 5:
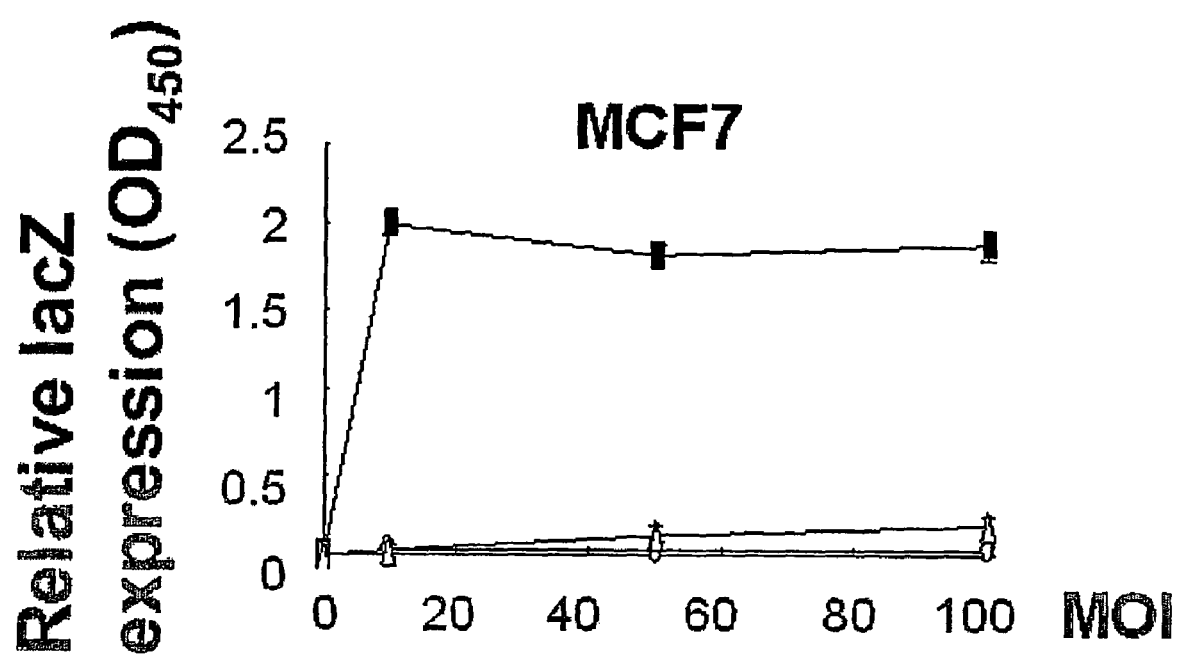
FIG. 5I is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in tumor cell line (MCF7)
FIG. 5J is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in normal cell line (173WE)
FIG. 5K is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in normal cell line (CBHEL)
FIG. 5L is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in normal cell line (MRC5)
FIG. 5M is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in normal cell line (IMR90)
FIG. 5N is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in normal cell line (WI38)
FIG. 5O is a graph showing results of quantitative analysis of the expression patterns of the LacZ gene of the replication-deficient recombinant adenoviral vectors dl-CMV-Z (■), dl-TERT-Z (o) and dl-mTERT-Z (Δ) according to the present invention in normal cell line (BJ)
Figure 5J:
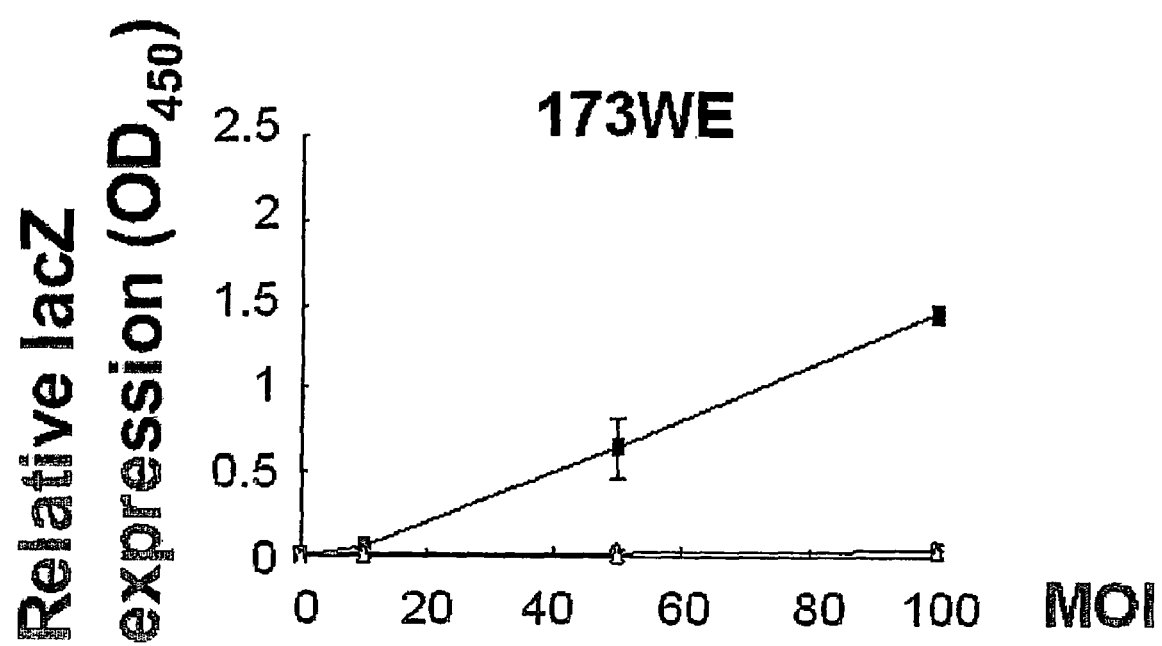
Figure 5K:
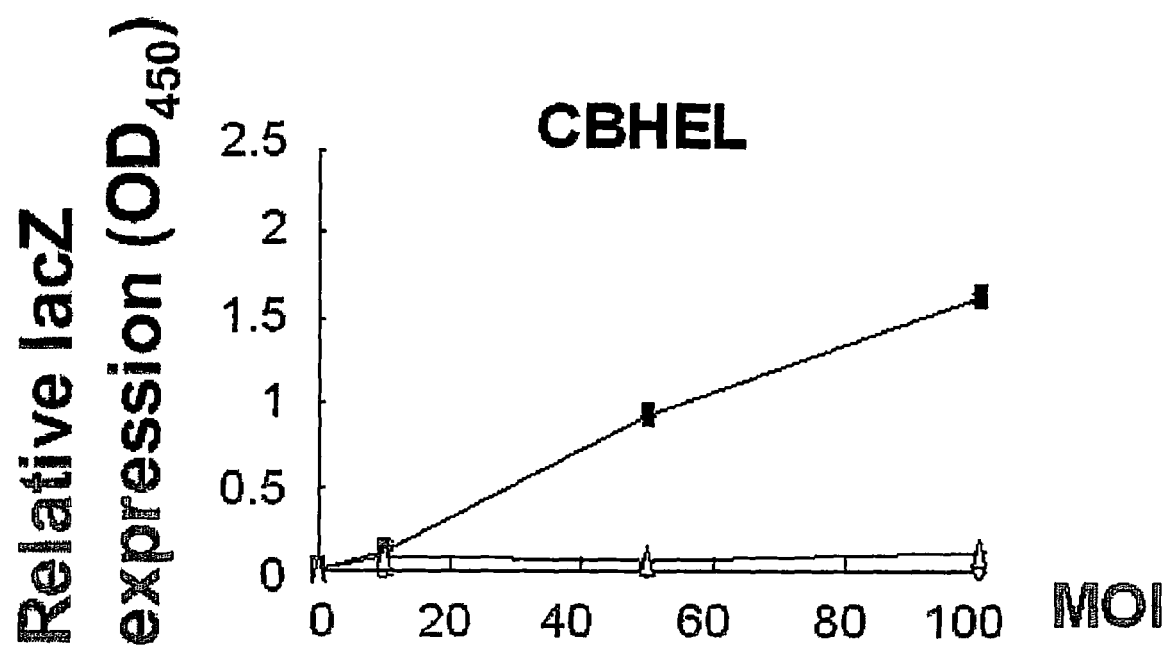
Figure 5L:
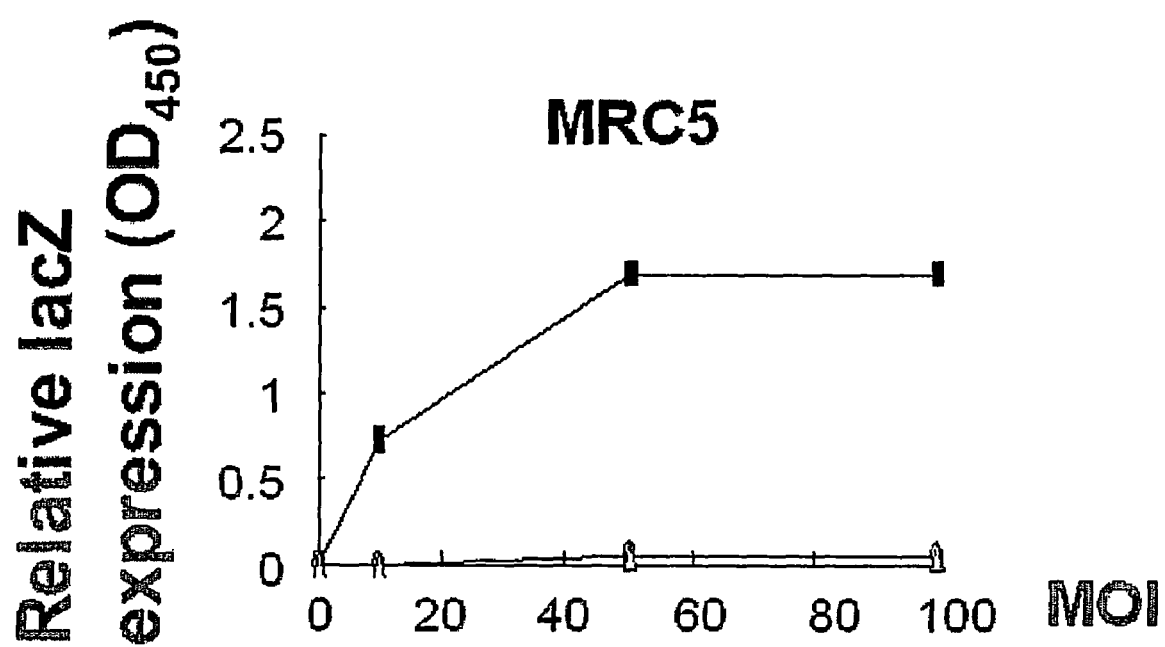
Figure 5M:
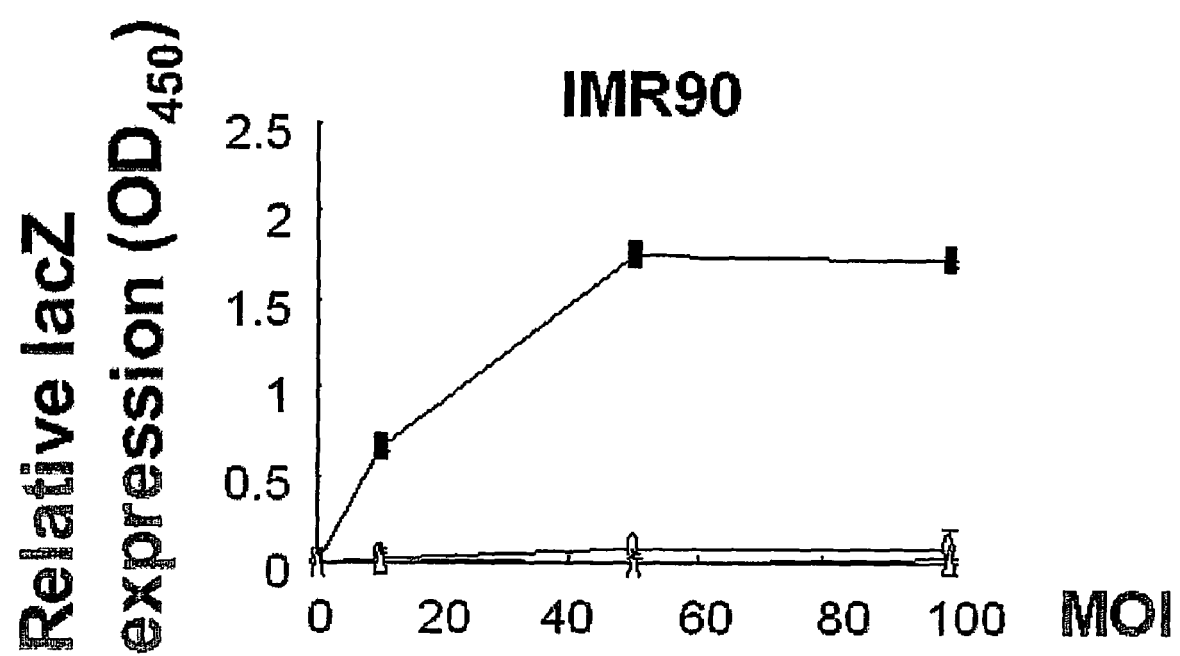
Figure 5N:
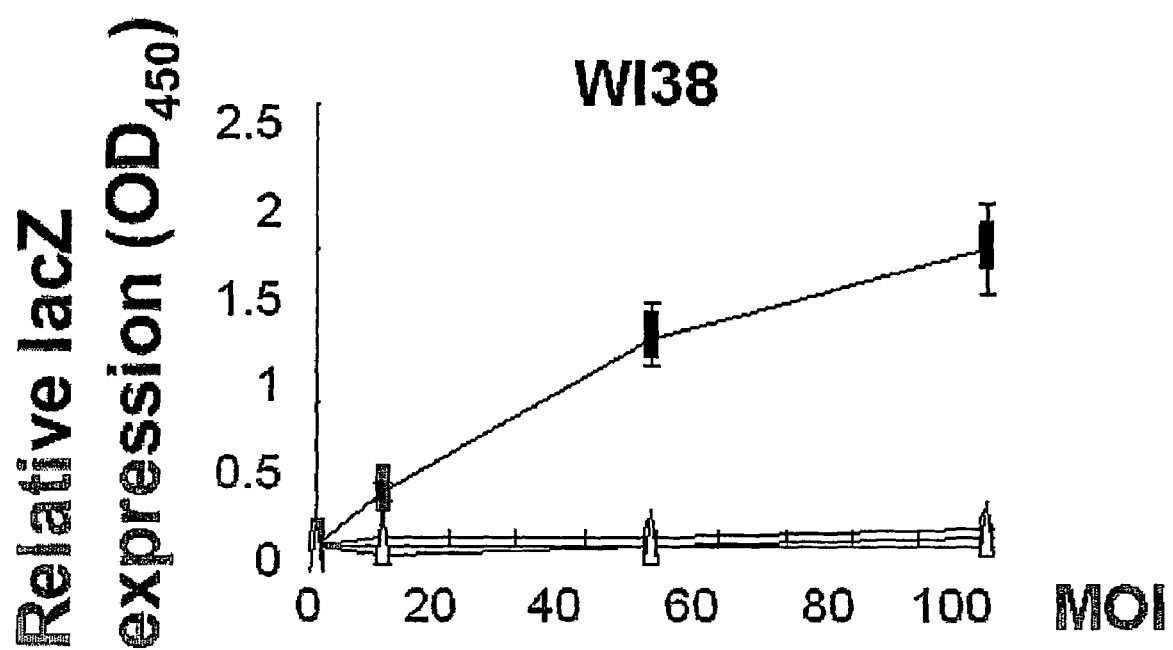
Figure 5O:
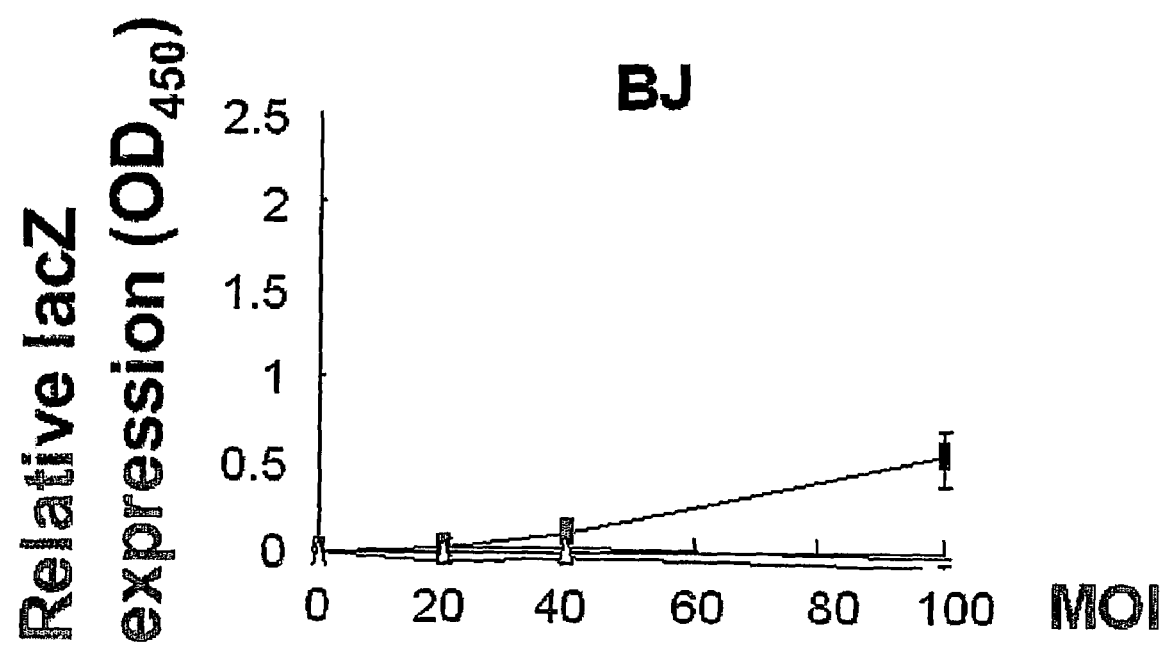

As shown in FIGS. 5A to 5O, when regulated under the CMV promoter, the LacZ gene expression increased with the viral titers. In particular, regardless of the intracellular telomerase activity, all of the tested cell lines including the normal cell lines exhibited high-level LacZ gene expression. In contrast, when being under the hTERT promoter or m-hTERT promoter control, the tumor cell lines with high telomerase activity, that is, all of the tumor cell lines except for the human breast cancer cell line MCF-7 expressed the LacZ gene product β-galactosidase increasingly with the viral titers, whereas, in the normal cell lines, β-gal activity was rarely detected even at the highest titer of MOI 100. These results indicate that the hTERT and m-hTERT promoters have excellent tumor-specificity. In detail, in case of the normal cell line IMR90 infected with each adenovirus at MOI 100, the $OD_{420}$ value, which reflected a relative amount of expressed β-galactosidase, when the LacZ gene was under the CMV promoter control, was 1.714, whereas, when the LacZ gene was regulated under the hTERT promoter or the m-hTERT promoter, the relative $OD_{420}$. values were 0.101 and 0.025, respectively. In this case, compared to the case of being under the CMV promoter control, under the control of the hTERT and m-hTERT promoters, the LacZ gene expression levels decreased by about 17 times and about 68 times, respectively. In case of the normal cell line BJ infected with each adenovirus at MOI 500, when the LacZ gene was regulated under the CMV, hTERT or m-hTERT promoter, the relative $OD_{420}$ values were 0.548, 0.001 and 0.001, respectively. These results indicated that the hTERT and m-hTERT promoters were rarely activated in the normal BJ cells. These large difference between the CMV promoter and the hTERT and m-hTERT promoters in the LacZ gene expression levels was observed in other normal cell lines 173We, CBHEL, WI38 and MRC5. On the other hand, in the tumor cell lines with high telomerase activity, the LacZ gene was expressed in much higher levels under the control of the m-hTERT promoter than under the control of the wild-type hTERT promoter. That is, when the SK-Hep1 cells were infected with the dl-TERT-Z at MOI 50, the relative $OD_{420}$ value for the LacZ expression level was 0.182. In contrast, when the SK-Hep1 cells were infected with an equal titer of the dl-mTERT-Z, the relative $OD_{420}$ value for the LacZ expression level was 1.82, and this level was about 10-fold higher than the case of being infected with the dl-TERT-Z. In addition, in Hep3B cells, in comparison with the case of being under the m-hTERT promoter control, the LacZ gene was expressed in about 10-fold higher levels when being under the m-hTERT promoter control (relative $OD_{420}$ values: dl-TERT-Z: 0.135; dl-mTERT-Z: 1.322) (Table 1). As described above, compared to the wild-type hTERT promoter, the m-hTERT promoter according to the present invention was a stronger promoter capable of much strongly inducing gene expression. In addition, since the m-hTERT promoter rarely had promoter activity in normal cell lines, it had excellent tumor cell-specificity.

TABLE 1

| | dl-CMV-Z | | | dl-TERT-Z | | | dl-mTERT-Z | | |
|---|---|---|---|---|---|---|---|---|---|
| MOI | 10 | 50 | 100 | 10 | 50 | 100 | 10 | 50 | 100 |
| H460 | 1.780 ± 0.18 | 1.879 ± 0.12 | 1.847 ± 0.10 | 0.033 ± 0.10 | 0.399 ± 0.05 | 0.829 ± 0.08 | 0.142 ± 0.01 | 1.594 ± 0.01 | 1.883 ± 0.06 |
| A549 | 1.658 ± 0.09 | 1.65 ± 0.08 | 1.706 ± 0.09 | 0.010 ± 0.04 | 0.178 ± 0.06 | 0.384 ± 0.07 | 0.062 ± 0.01 | 0.650 ± 0.02 | 1.011 ± 0.07 |
| U451N | 1.733 ± 0.05 | 1.765 ± 0.05 | 1.768 ± 0.04 | 0.267 ± 0.16 | 1.042 ± 0.12 | 1.291 ± 0.03 | 0.939 ± 0.13 | 1.785 ± 0.04 | 1.815 ± 0.08 |
| U343 | 1.831 ± 0.01 | 1.902 ± 0.07 | 1.807 ± 0.03 | 0.079 ± 0.01 | 0.732 ± 0.13 | 1.174 ± 0.01 | 0.379 ± 0.01 | 1.819 ± 0.03 | 2.057 ± 0.07 |
| MCF7 | 2.027 ± 0.07 | 1.844 ± 0.03 | 1.892 ± 0.08 | 0.022 ± 0.03 | 0.020 ± 0.03 | 0.036 ± 0.03 | 0.020 ± 0.02 | 0.136 ± 0.05 | 0.183 ± 0.05 |
| C33A | 1.798 ± 0.08 | 1.796 ± 0.05 | 1.731 ± 0.09 | 0.037 ± 0.08 | 0.640 ± 0.21 | 0.964 ± 0.07 | 0.385 ± 0.02 | 1.730 ± 0.4 | 1.712 ± 0.09 |
| Hep3B | 1.858 ± 0.10 | 1.680 ± 0.18 | 1.921 ± 0.14 | 0.060 ± 0.05 | 0.135 ± 0.13 | 0.337 ± 0.03 | 0.331 ± 0.04 | 1.322 ± 0.10 | 1.731 ± 0.05 |
| HepG2 | 1.647 ± 0.01 | 1.714 ± 0.06 | 1.662 ± 0.07 | 0.038 ± 0.01 | 0.231 ± 0.02 | 0.402 ± 0.04 | 0.652 ± 0.11 | 1.705 ± 0.05 | 1.716 ± 0.11 |
| SK-Hep1 | 1.916 ± 0.06 | 1.941 ± 0.01 | 1.933 ± 0.04 | 0.047 ± 0.01 | 0.182 ± 0.04 | 0.373 ± 0.01 | 0.435 ± 0.05 | 1.82 ± 0.04 | 1.994 ± 0.02 |
| 173WE | 0.059 ± 0.02 | 0.647 ± 0.12 | 1.453 ± 0.04 | 0.003 ± 0.02 | 0.025 ± 0.12 | 0.040 ± 0.01 | 0.021 ± 0.03 | 0.026 ± 0.01 | 0.035 ± 0.03 |
| CBHEL | 0.117 ± 0.01 | 0.928 ± 0.01 | 1.642 ± 0.03 | 0.006 ± 0.01 | 0.005 ± 0.01 | 0.007 ± 0.01 | 0.069 ± 0.10 | 0.061 ± 0.01 | 0.103 ± 0.01 |
| IMR90 | 0.658 ± 0.04 | 1.758 ± 0.01 | 1.714 ± 0.01 | 0.019 ± 0.02 | 0.075 ± 0.02 | 0.101 ± 0.11 | 0.040 ± 0.04 | 0.012 ± 0.01 | 0.025 ± 0.01 |

TABLE 1-continued

| | dl-CMV-Z | | | dl-TERT-Z | | | dl-mTERT-Z | | |
|---|---|---|---|---|---|---|---|---|---|
| MOI | 10 | 50 | 100 | 10 | 50 | 100 | 10 | 50 | 100 |
| WI38 | 0.376 ± 0.05 | 1.43 ± 0.22 | 2.012 ± 0.31 | 0.001 ± 0.01 | 0.001 ± 0.03 | 0.034 ± 0.05 | 0.045 ± 0.02 | 0.035 ± 0.05 | 0.093 ± 0.04 |
| BJ* | 0.032 ± 0.06 | 0.115 ± 0.02 | 0.548 ± 0.15 | 0.001 ± 0.02 | 0.001 ± 0.01 | 0.001 ± 0.01 | 0.001 ± 0.01 | 0.001 ± 0.01 | 0.001 ± 0.01 |
| MRC5 | 0.721 ± 0.12 | 1.696 ± 0.03 | 1.683 ± 0.05 | 0.011 ± 0.01 | 0.044 ± 0.02 | 0.059 ± 0.01 | 0.013 ± 0.06 | 0.060 ± 0.06 | 0.053 ± 0.03 |

EXAMPLE 6

Immunoblotting Analysis of the Replication-Competent Recombinant Adenoviruses In order to determine whether the viral replication happened in a tumor cell-specific manner, tumor cell lines and normal cell lines were infected with a control Ad-ΔE1B19 or each of the replication-competent recombinant adenoviruses, and were evaluated for expressed E1 protein levels. Tumor cell lines (C33A, A549, HeLa and SK-Hep1) and normal cell lines (IMR90, MRC5 and BJ) were individually aliquotted onto 6-well plates at a density of $3 \times 10^5$ to $1 \times 10^6$ cells per well, and, next day, infected with the Ad-ΔE1B19, Ad-TERT-Δ19 or Ad-mTERT-Δ19 at an MOI of 1 for the tumor cell lines or at an MOI of 10 for the normal cell lines. After two days of the viral infection, the infected cells were harvested, and lysed with a cell lysis buffer (50 mM HEPES, 0.15 M NaCl, 0.5% NP-40, protease inhibitors: PMSF, TLCK, TPCK). The cell lysates were subjected to SDS-PAGE (Sodium dodecyl sulfate polyacrylamide gel electrophoresis). Then, proteins separated on a SDS-PAGE gel were electro-transferred onto a PVDF membrane, and was hybridized with, as a primary antibody, an antibody specifically recognizing the adenovirus E1A protein (sc-430; Santa Cruz Biotech., Santa Cruz, Calif.) and then with a HRP (horse radish peroxidase)-conjugated secondary antibody. Each blot was developed using an ECL kit (Enhanced Chemi-Luminescence: sc-2048; Santa Cruz Biotech., Santa Cruz, Calif.) to analyze protein expression patterns.

Figure 6:
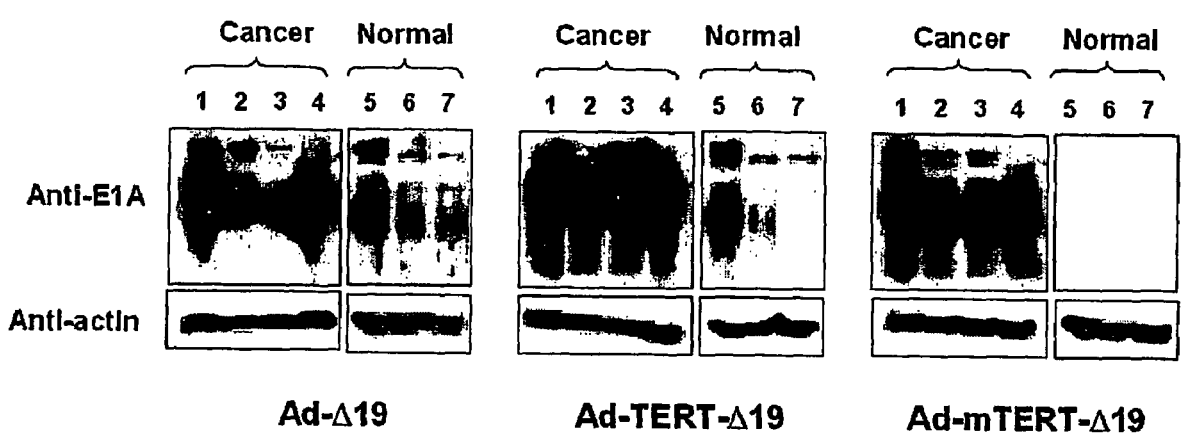
FIG. 6 shows expression patterns of an E1 gene of the replication-competent recombinant adenoviral vectors Ad-mTERT-Δ19, Ad-TERT-Δ19 and Ad-ΔE1B19 according to the present invention in various tumor cell lines and normal cell lines (1: C33A, 2: A549, 3: HeLa, 4: SK-Hep1, 5: WI38, 6: BJ and 7: IMR90)

As shown in FIG. 6, in case of the Ad-ΔE1B19, in all of the tumor cells and the normal cells, the adenovirus actively replicated, resulting in high expression levels of the E1 protein. In contrast, when the cells were infected with the Ad-mTERT-Δ19 adenovirus, the E1 protein was expressed in only the tumor cell lines with high telomerase activity, absolutely not in all of the normal cell lines (WI38, BJ and IMR90) with low telomerase activity. These results indicate that the replication of the Ad-mTERT-Δ19 adenovirus is regulated by the m-hTERT promoter in a tumor cell-specific manner. However, in the case of the Ad-TERT-Δ19 replication of which was regulated by the wild-type hTERT promoter, the adenovirus actively replicated in the tumor cells, resulting in high expression levels of the E1 protein, while the E1 protein expression was observed in the normal cell lines WI38 and BJ. These results indicate that the Ad-TERT-Δ19 adenovirus is less tumor-specific in replication than the Ad-mTERT-Δ19.

EXAMPLE 7

Evaluation of the Cytolytic Effect of the Replication-Competent Recombinant Adenoviruses In order to investigate the tumor cell-specific cytolytic effect of the Ad-TERT-Δ19 and Ad-mTERT-Δ19 adenoviruses, several tumor cell lines and normal cell lines were infected with the adenoviruses using an Ad-ΔE1B19 replication-competent adenovirus as a positive control and a dl-CMV-Z replication-deficient adenovirus as a negative control, with various titers, and cell viability was then assayed. Tumor cell lines (SK-Hep1, H460, C33A, U251N, A549 and HeLa) and normal cell lines (BJ, WI38 and IMR90) were individually aliquotted onto 24-well plates at a density of $2$-$5 \times 10^4$ per well, and, next day, infected with the dl-CMV-Z, the Ad-ΔE1B19, the Ad-TERT-Δ19 or the Ad-mTERT-Δ19 at various MOIs of 0.01, 0.1, 1, 10 and 100. When the Ad-ΔE1B19 adenovirus almost completely killed cells at an MOI of 0.01 or 0.1, all culture media were removed, and cells attached on the bottom of the plates were fixed and stained with 0.5% crystal violet in 50% methanol.

Figure 7A:
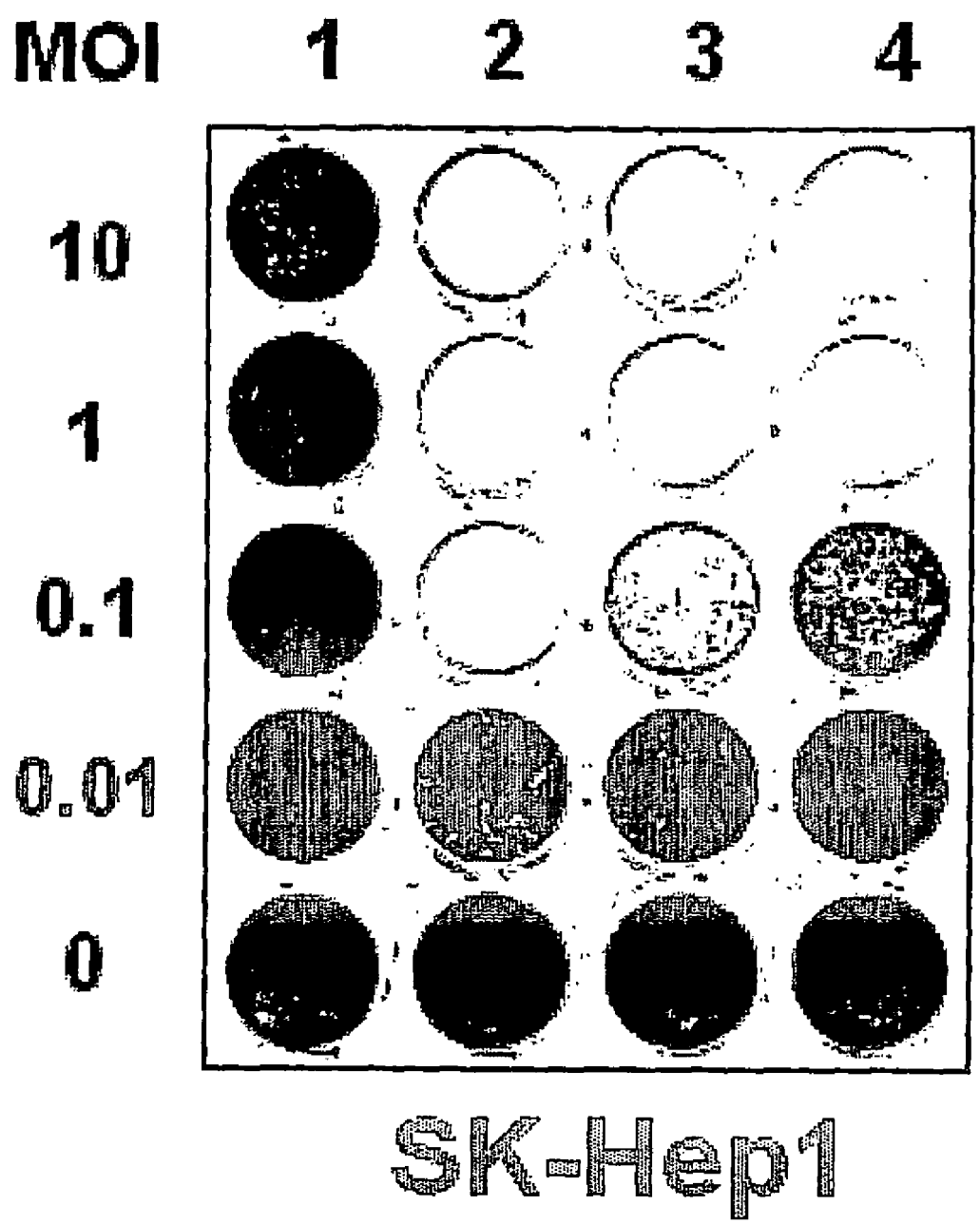
FIG. 7A shows oncolytic effect of the replication-competent recombinant adenoviral vectors according to the present invention on tumor cell line SK-Hep1 (1: dl-CMV-Z, 2: Ad-ΔE1B9, 3: Ad-TERT-Δ19 and 4: Ad-mTERT-Δ19)
Figure 7B:
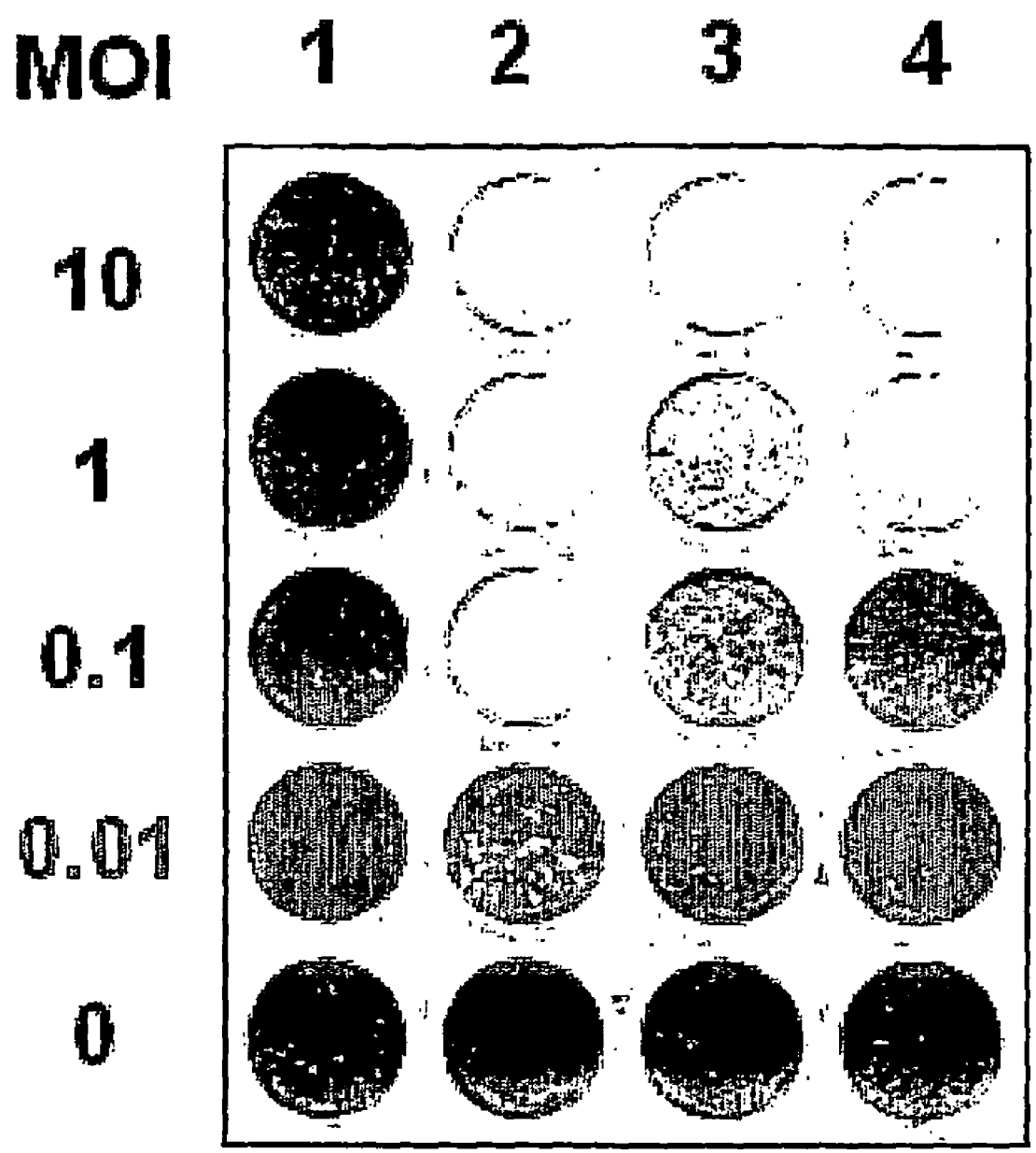
FIG. 7B shows oncolytic effect of the replication-competent recombinant adenoviral vectors according to the present invention on tumor cell line H460 (1: dl-CMV-Z, 2: Ad-ΔE1B19, 3: Ad-TERT-Δ19 and 4: Ad-mTERT-Δ19)
Figure 7C:
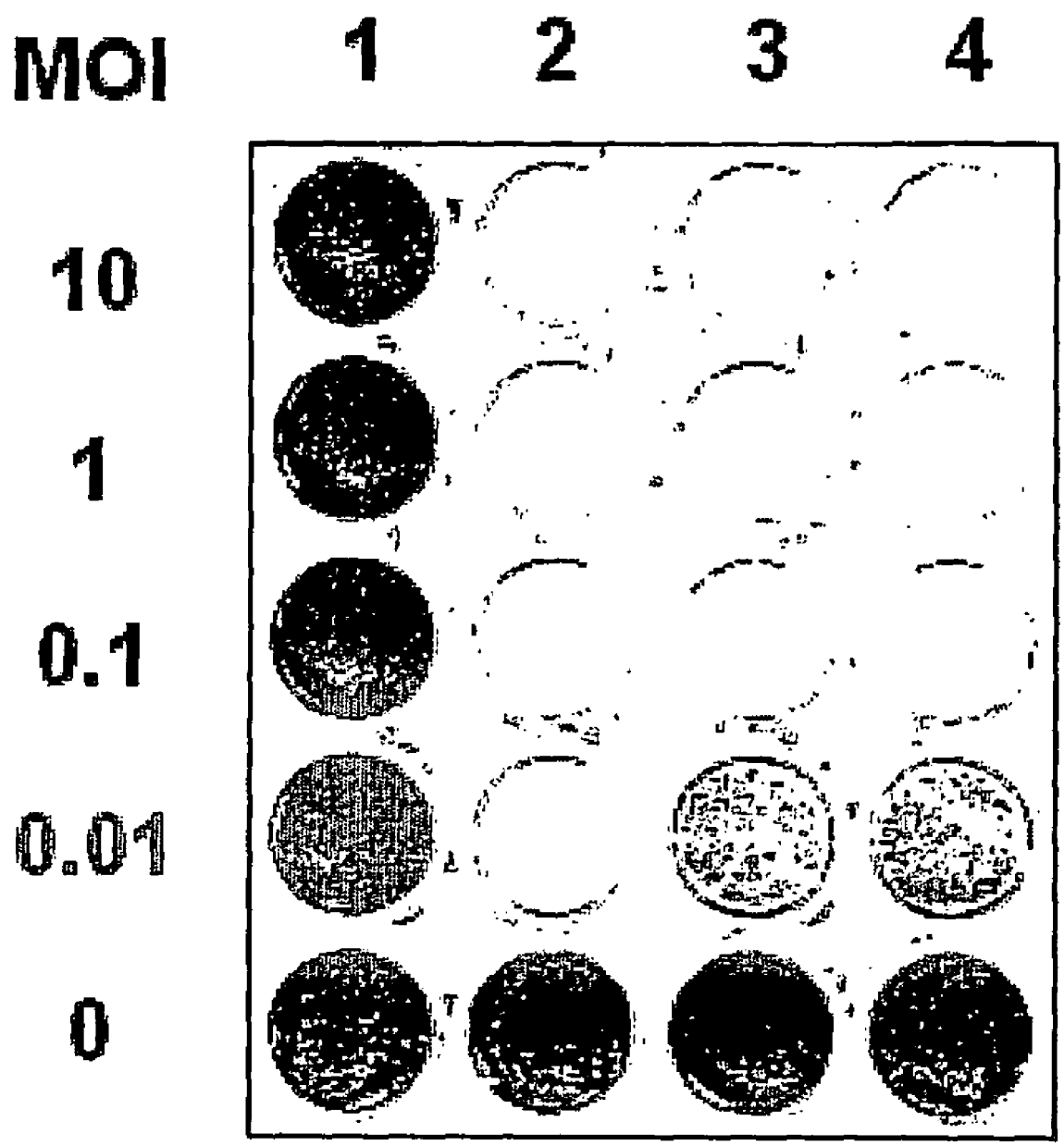
FIG. 7C shows oncolytic effect of the replication-competent recombinant adenoviral vectors according to the present invention on tumor cell line C33A (1: dl-CMV-Z, 2: Ad-ΔE1B19B 3: Ad-TERT-Δ19 and 4: Ad-mTERT-Δ19)
Figure 7D:
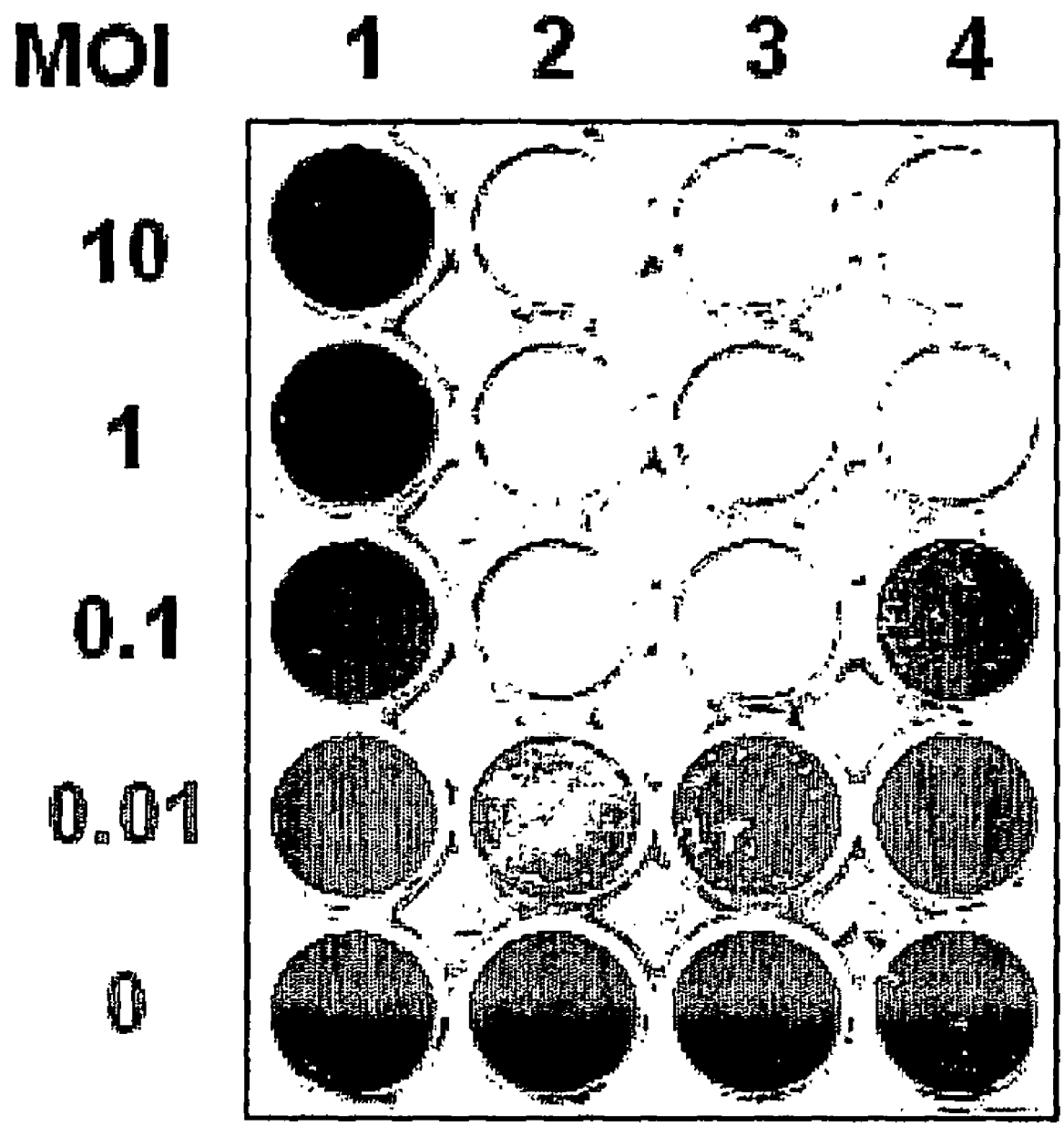
FIG. 7D shows oncolytic effect of the replication-competent recombinant adenoviral vectors according to the present invention on tumor cell line U251N (1: dl-CMV-Z, 2: Ad-ΔE1B19, 3: Ad-TERT-Δ19 and 4: Ad-mTERT-Δ19)
Figure 7E:
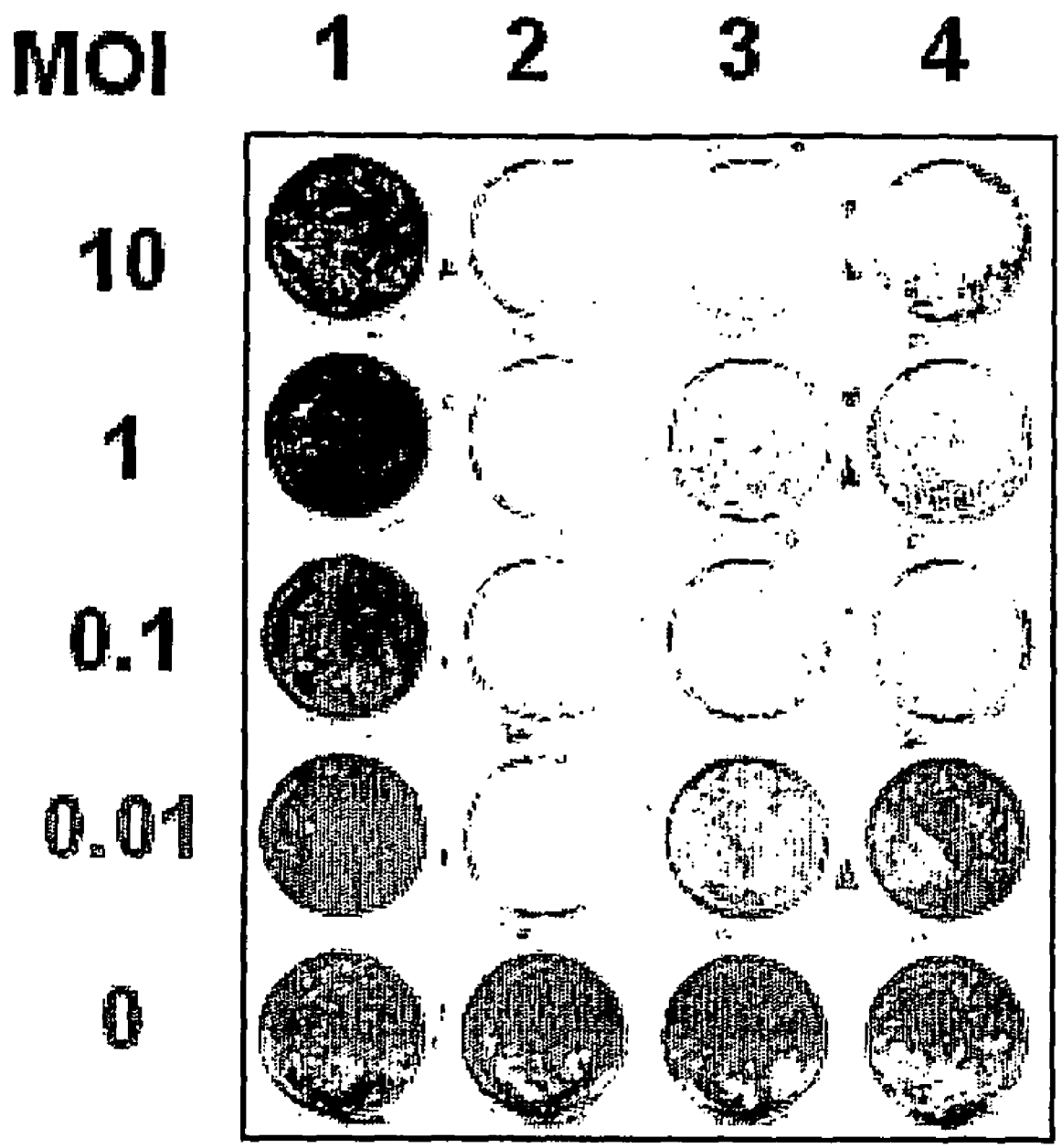
FIG. 7E shows oncolytic effect of the replication-competent recombinant adenoviral vectors according to the present invention on tumor cell line A549 (1: dl-CMV-Z, 2: Ad-ΔE1B19, 3: Ad-TERT-Δ19 and 4: Ad-mTERT-Δ19)
Figure 7F:
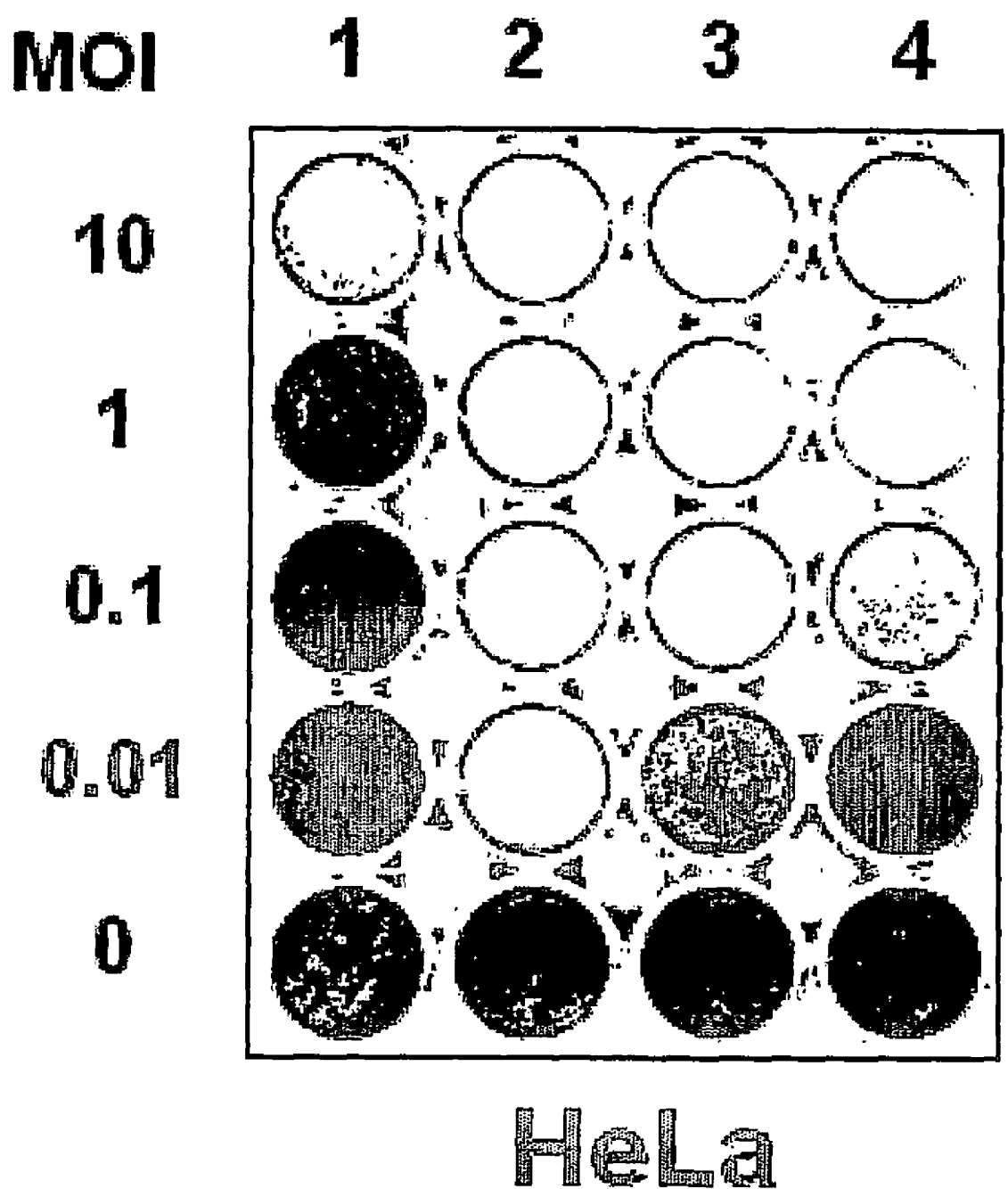
FIG. 7F shows oncolytic effect of the replication-competent recombinant adenoviral vectors according to the present invention on tumor cell line (HeLa) (1: dl-CMV-Z, 2: Ad-ΔE1B19, 3: Ad-TERT-Δ19 and 4: Ad-mTERT-Δ19)
Figure 7G:
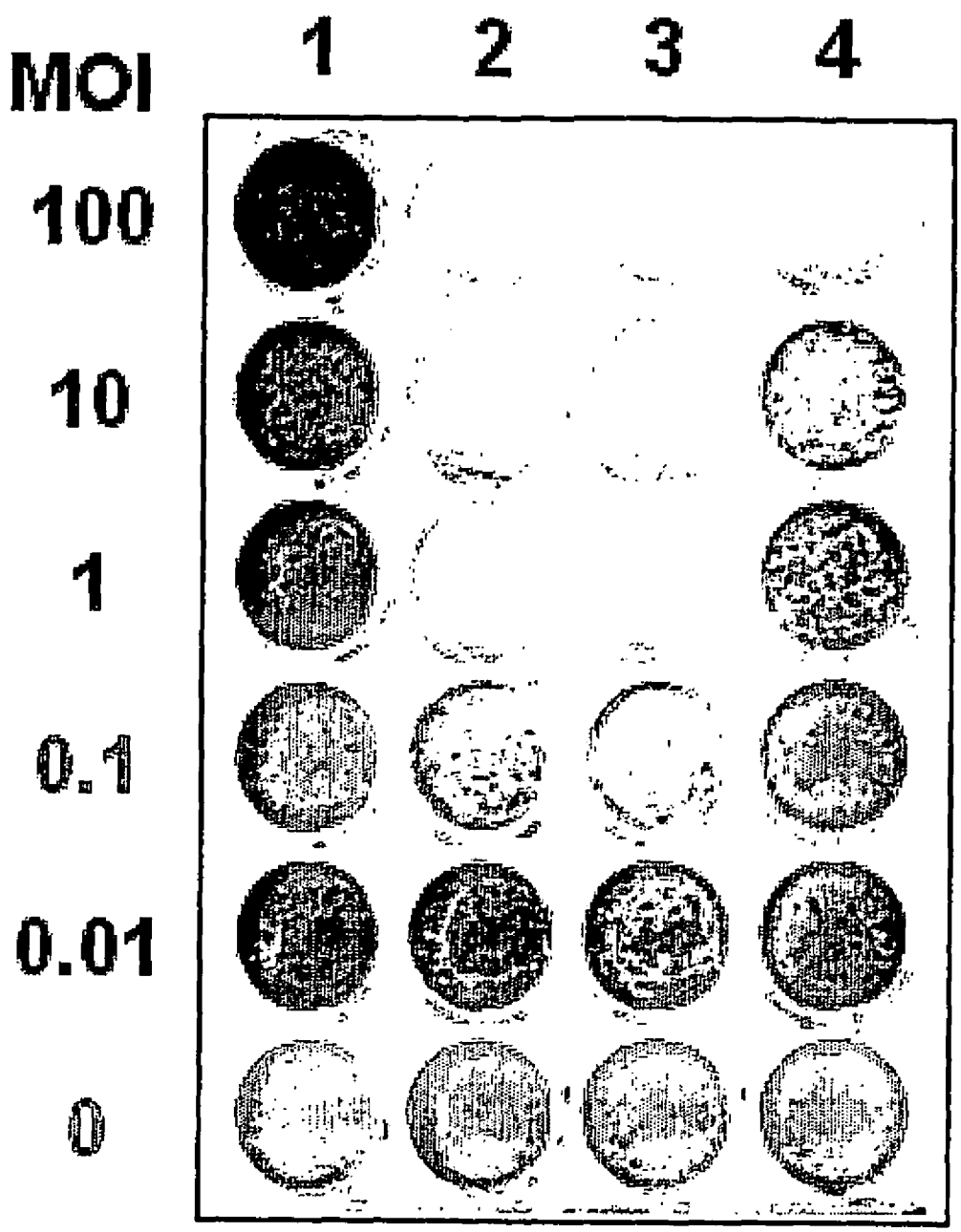
FIG. 7G shows oncolytic effect of the replication-competent recombinant adenoviral vectors according to the present invention on tumor cell line (BJ) (1: dl-CMV-Z, 2: Ad-ΔE1B19, 3: Ad-TERT-Δ19 and 4: Ad-mTERT-Δ19)
Figure 7H:
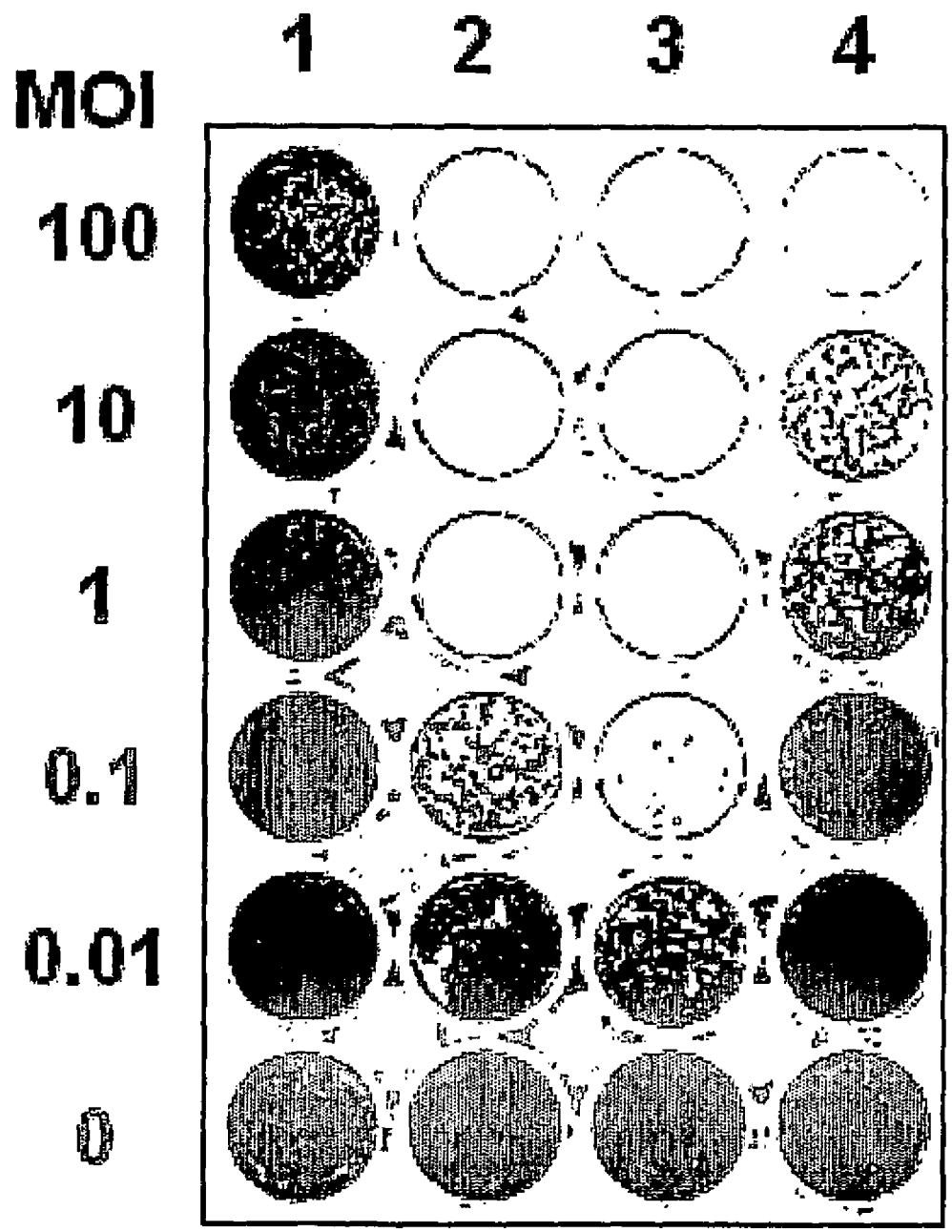
FIG. 7H shows oncolytic effect of the replication-competent recombinant adenoviral vectors according to the present invention on tumor cell line (WI38) (1: dl-CMV-Z, 2: Ad-ΔE1B19, 3: Ad-TERT-Δ19 and 4: Ad-mTERT-Δ19)
Figure 7:
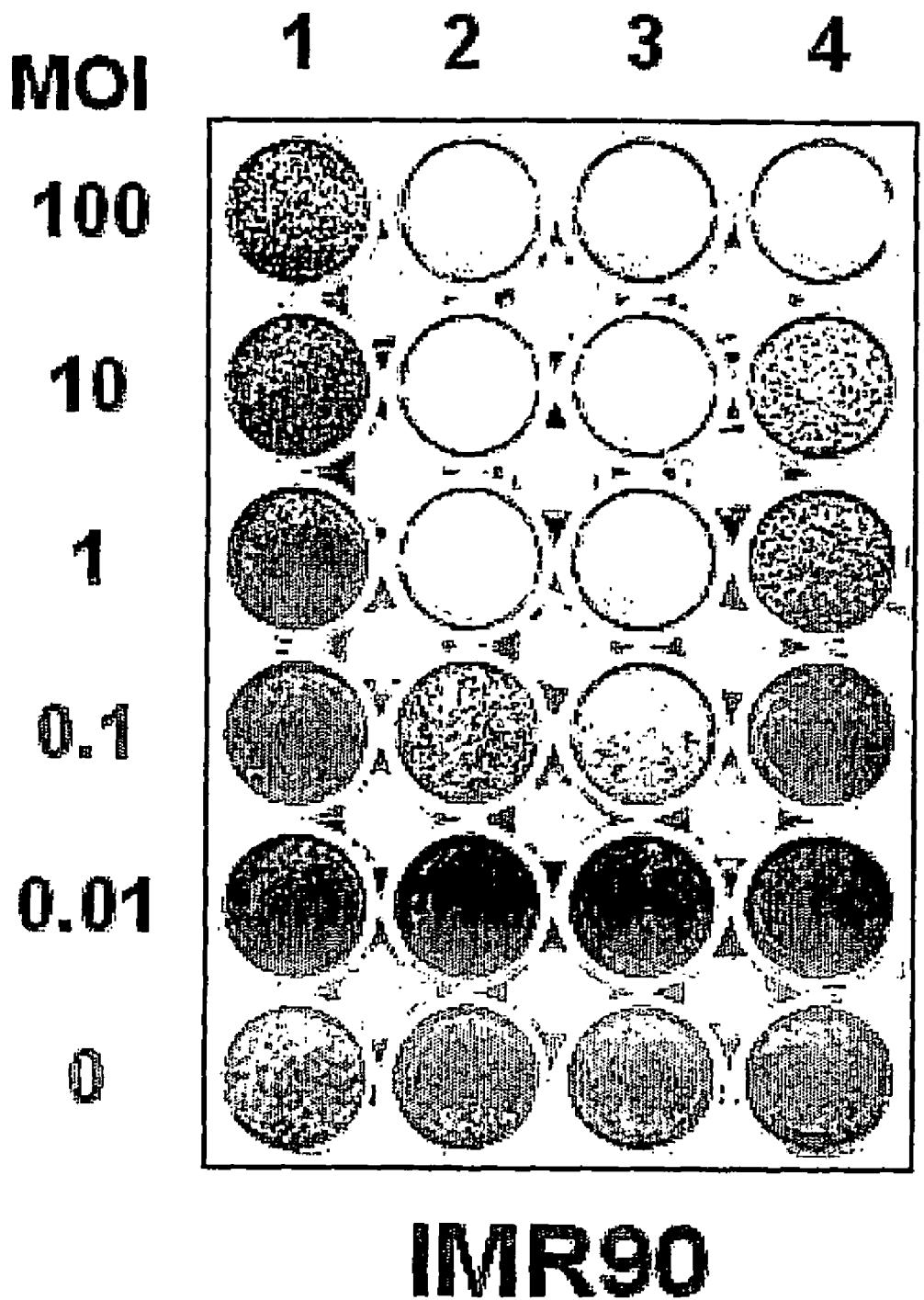
FIG. 7I shows oncolytic effect of the replication-competent recombinant adenoviral vectors according to the present invention on tumor cell line (IMR90) (1: dl-CMV-Z, 2: Ad-ΔE1B19, 3: Ad-TERT-Δ19 and 4: Ad-mTERT-Δ19)

As shown in FIGS. 7A to 7F, the negative control dl-CMV-Z replication-deficient adenovirus rarely replicated in the tumor cells and thus did not display oncolytic effect. In contrast, the Ad-TERT-Δ19 or the Ad-mTERT-Δ19 killed most of the tested tumor cells in the similar levels to the Ad-ΔE1B19, indicating that the two adenoviruses have highly potent oncolytic effect. However, as shown FIGS. 7G to 7I, in the normal cell lines BJ, WI38 and IMR90, the Ad-TERT-Δ19 killed the normal cells in the almost similar levels to the Ad-ΔE1B19 with no tumor-specificity, whereas the Ad-mTERT-Δ19 displayed the cytolytic effect about 100-fold lower than the Ad-ΔE1B19. These results demonstrate that the Ad-mTERT-Δ19 has tumor cell-specificity.

To analyze quantitatively the cytolytic effect of the Ad-TERT-Δ19 or the Ad-mTERT-Δ19 according to telomerase activity of cell lines, MTT assay was carried out, as follows. Tumor cell lines (SK-Hep1, H460, C33A, U251N, A549 and HeLa) and normal cell lines (BJ, WI38 and IMR90) were individually aliquotted onto 24-well plates with 70-90% confluency, and, next day, infected with the dl-CMV-Z, the Ad-ΔE1B19, the Ad-TERT-Δ19 or the Ad-mTERT-Δ19 adenoviruses at an MOI of 10 for the tumor cells and at an MOI of 50 for the normal cells. 200 μl of an MTT (3-(4,5-dimethylthiazol-2yl)-2,5-diphenyltetrazolium bromide, 2 mg/ml) solution was added to each well at regular time intervals. After incubation at 37° C. for 4 hrs, 1 ml of DMSO (dimethyl sulphoxide) was added to each well, followed by incubation at 37° C. for 10 min. Relative cell viability was analyzed by measuring absorbance at 540 nm.

Figure 8A:
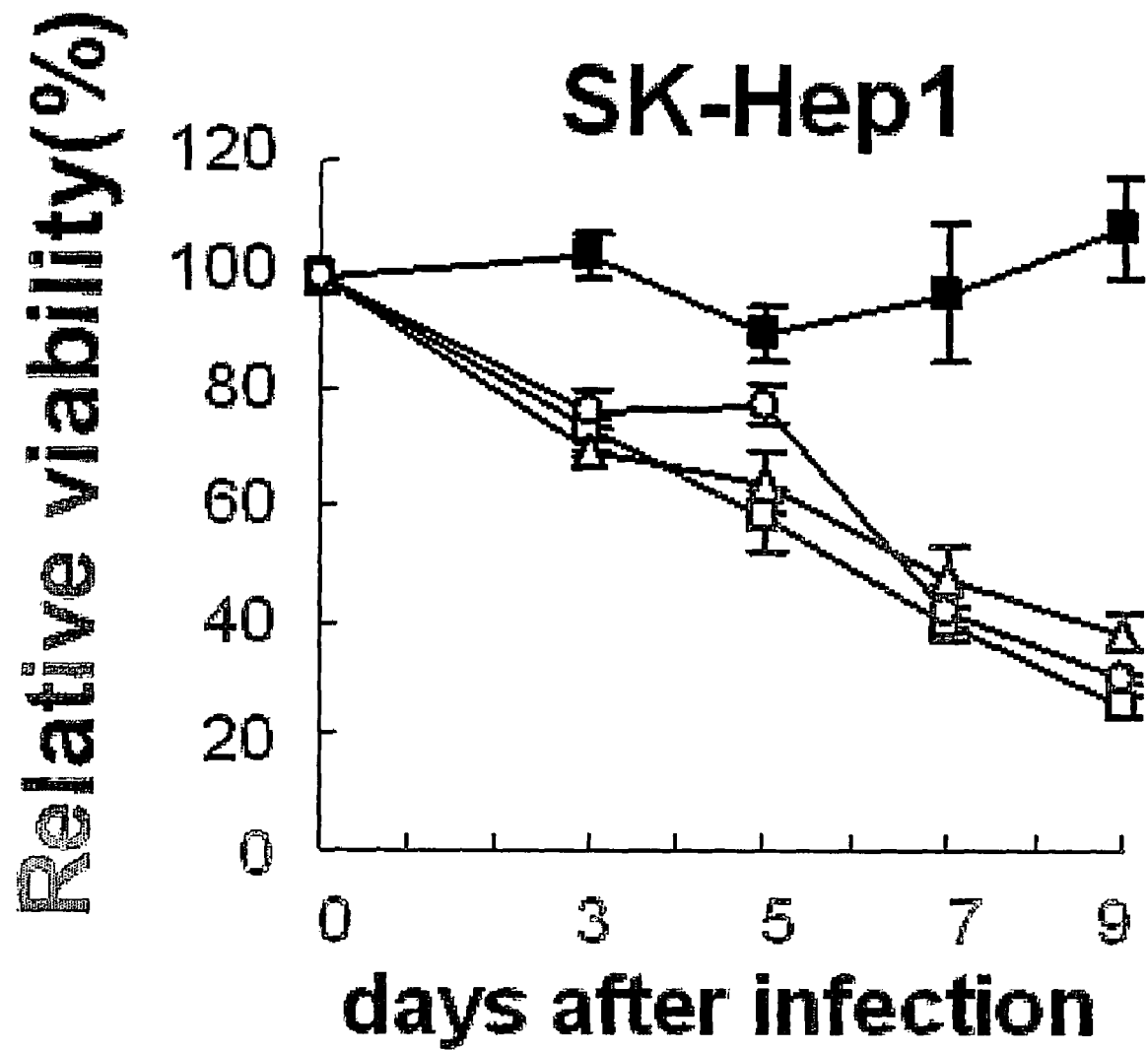
FIG. 8A is a graph showing results of quantitative analysis of the oncolytic effect on tumor cell line (SK-Hep1) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8B:
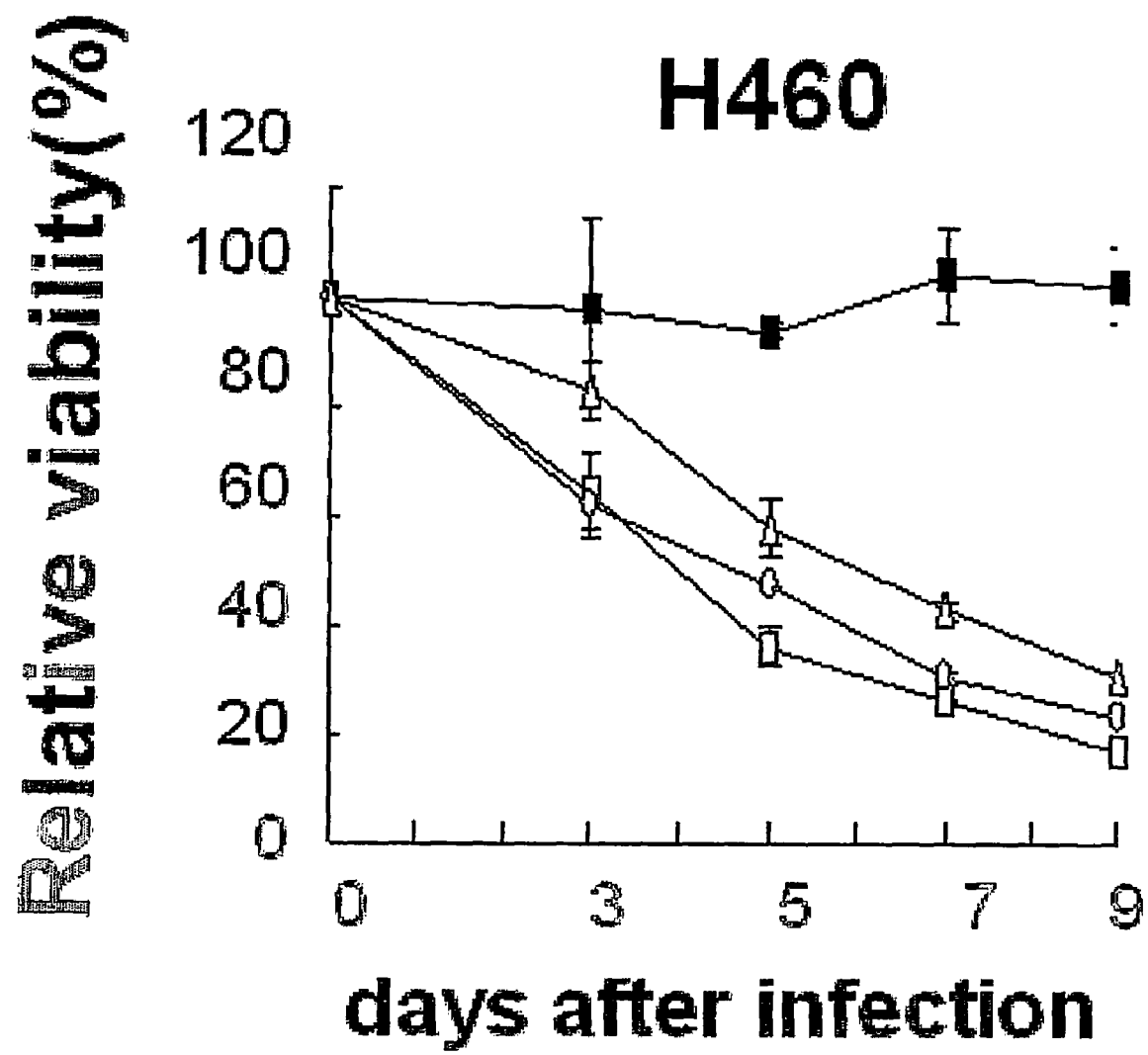
FIG. 8B is a graph showing results of quantitative analysis of the oncolytic effect on tumor cell line (H460) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8C:
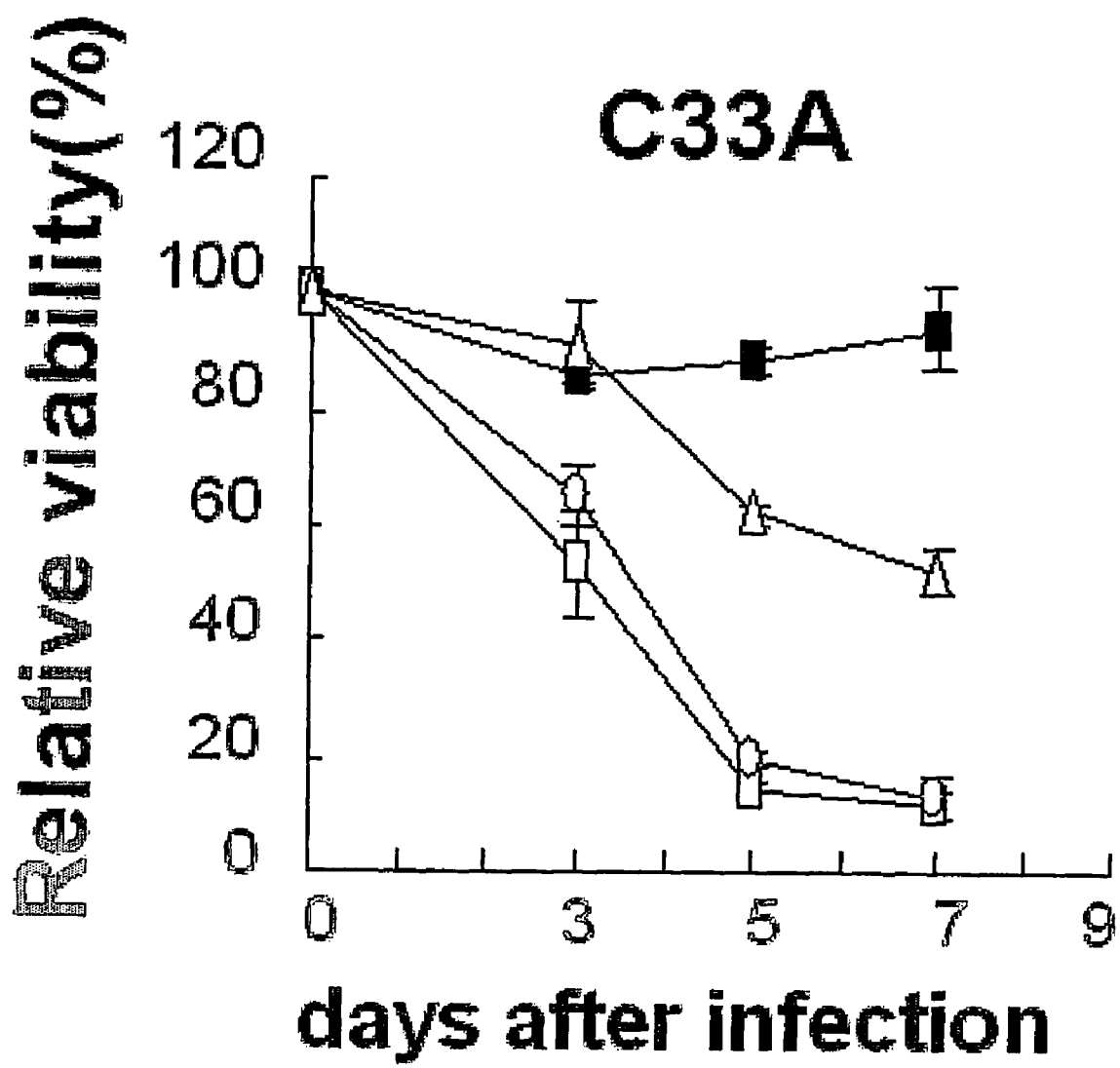
FIG. 8C is a graph showing results of quantitative analysis of the oncolytic effect on tumor cell line (C33A) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8D:
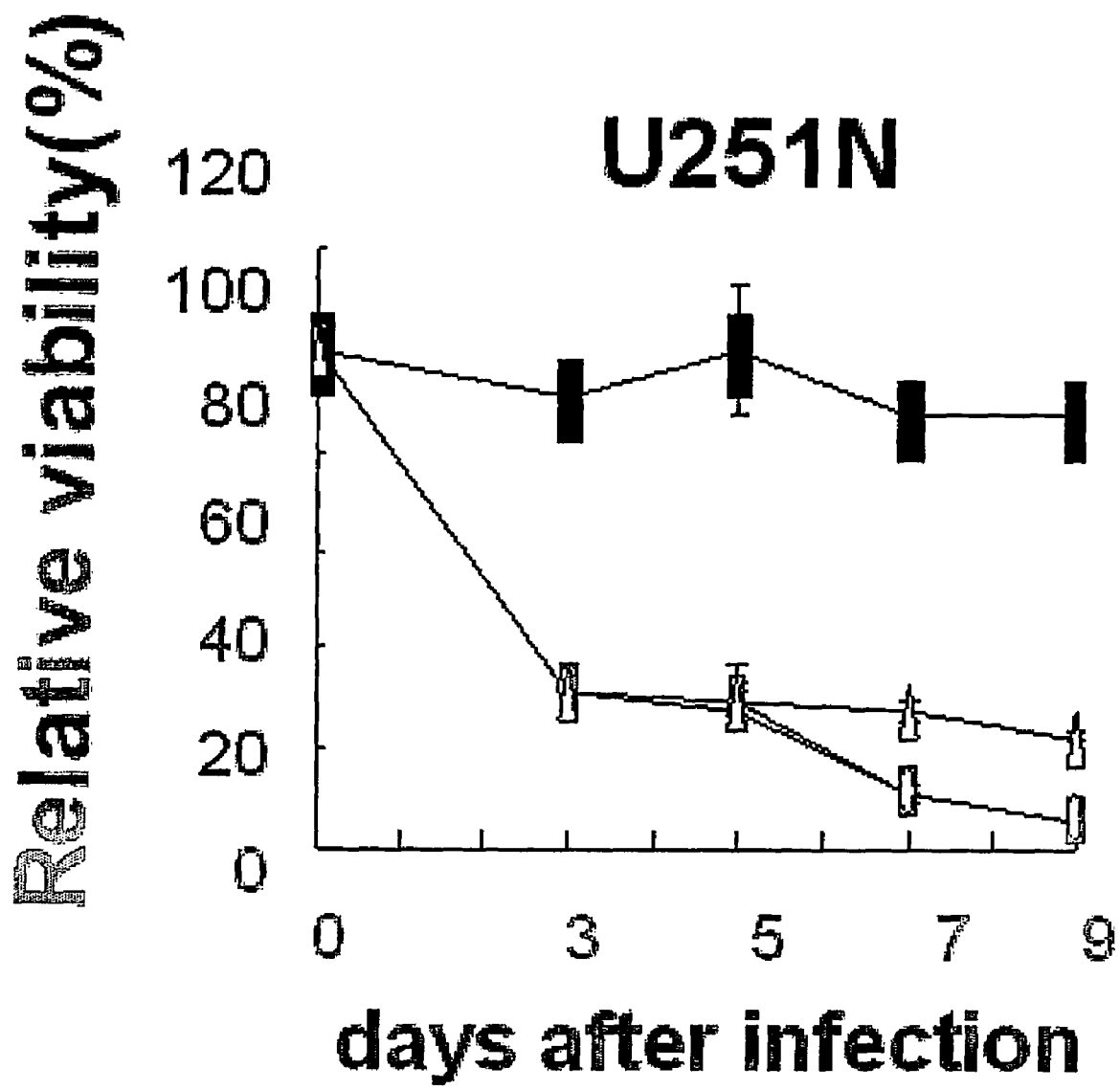
FIG. 8D is a graph showing results of quantitative analysis of the oncolytic effect on tumor cell line (U251N) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8E:
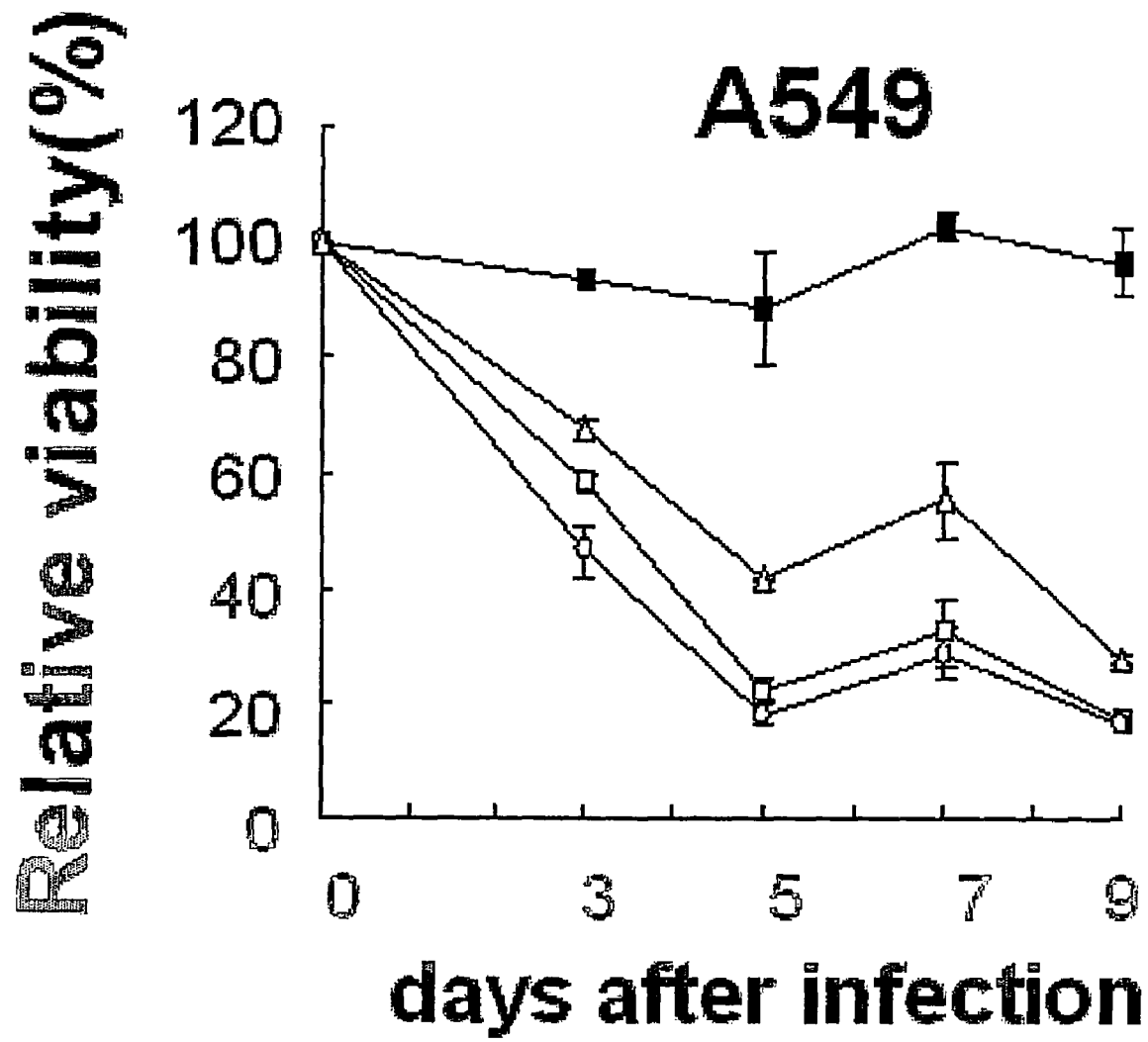
FIG. 8E is a graph showing results of quantitative analysis of the oncolytic effect on tumor cell line (A549) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8F:
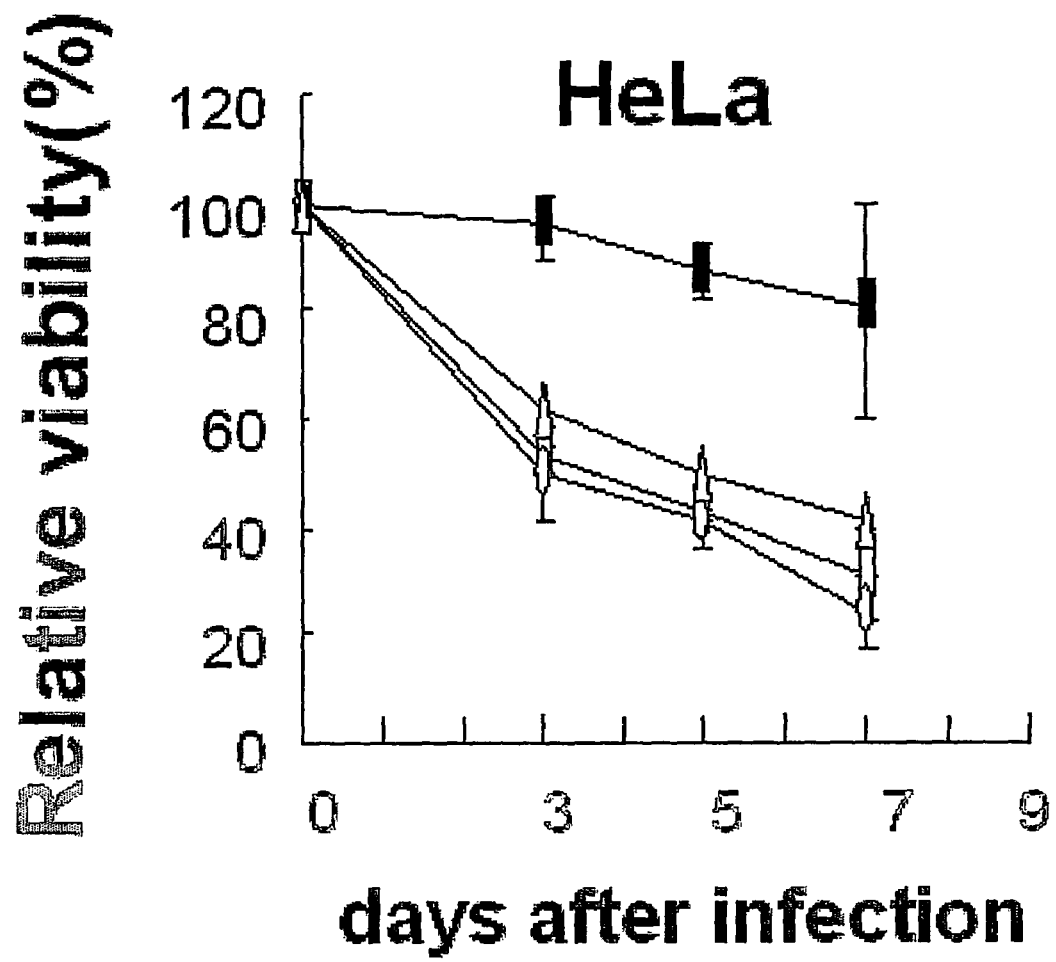
FIG. 8F is a graph showing results of quantitative analysis of the oncolytic effect on tumor cell line (HeLa) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8G:
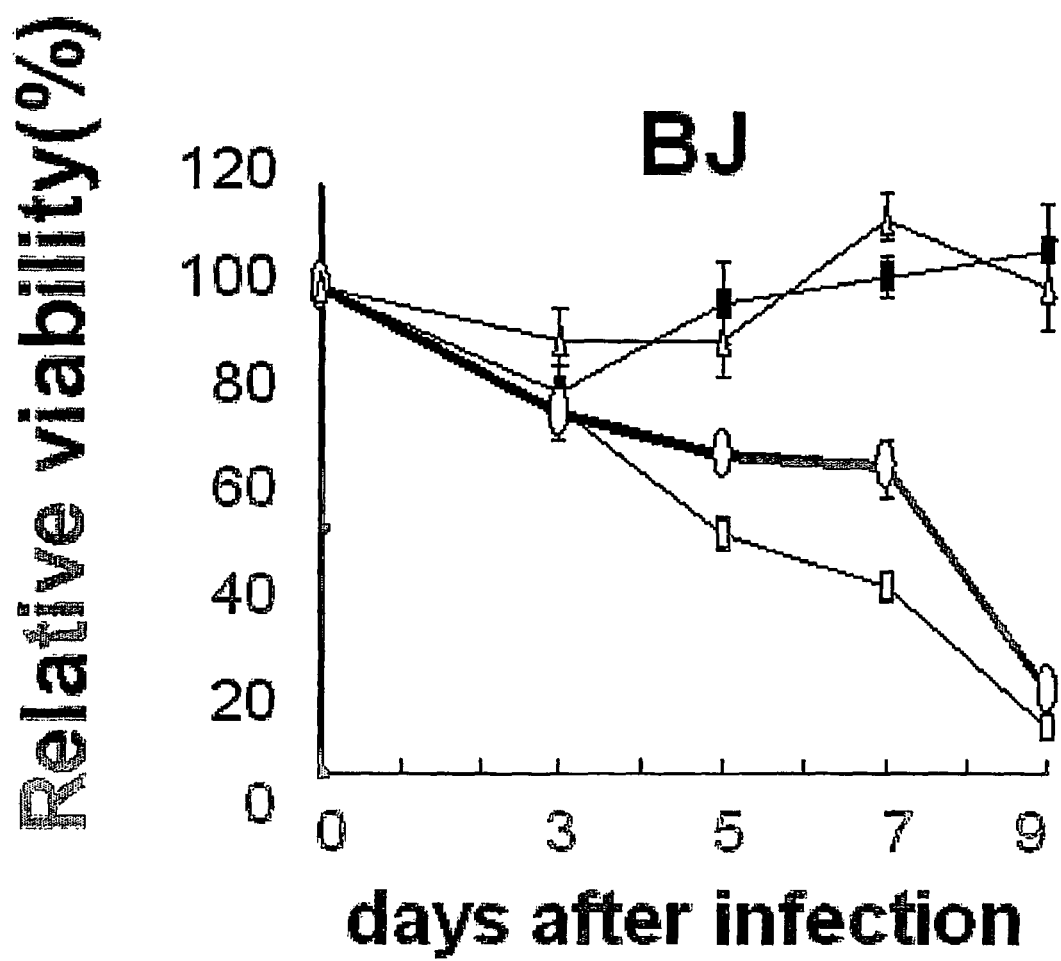
FIG. 8G is a graph showing results of quantitative analysis of the oncolytic effect on tumor cell line (BJ) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8H:
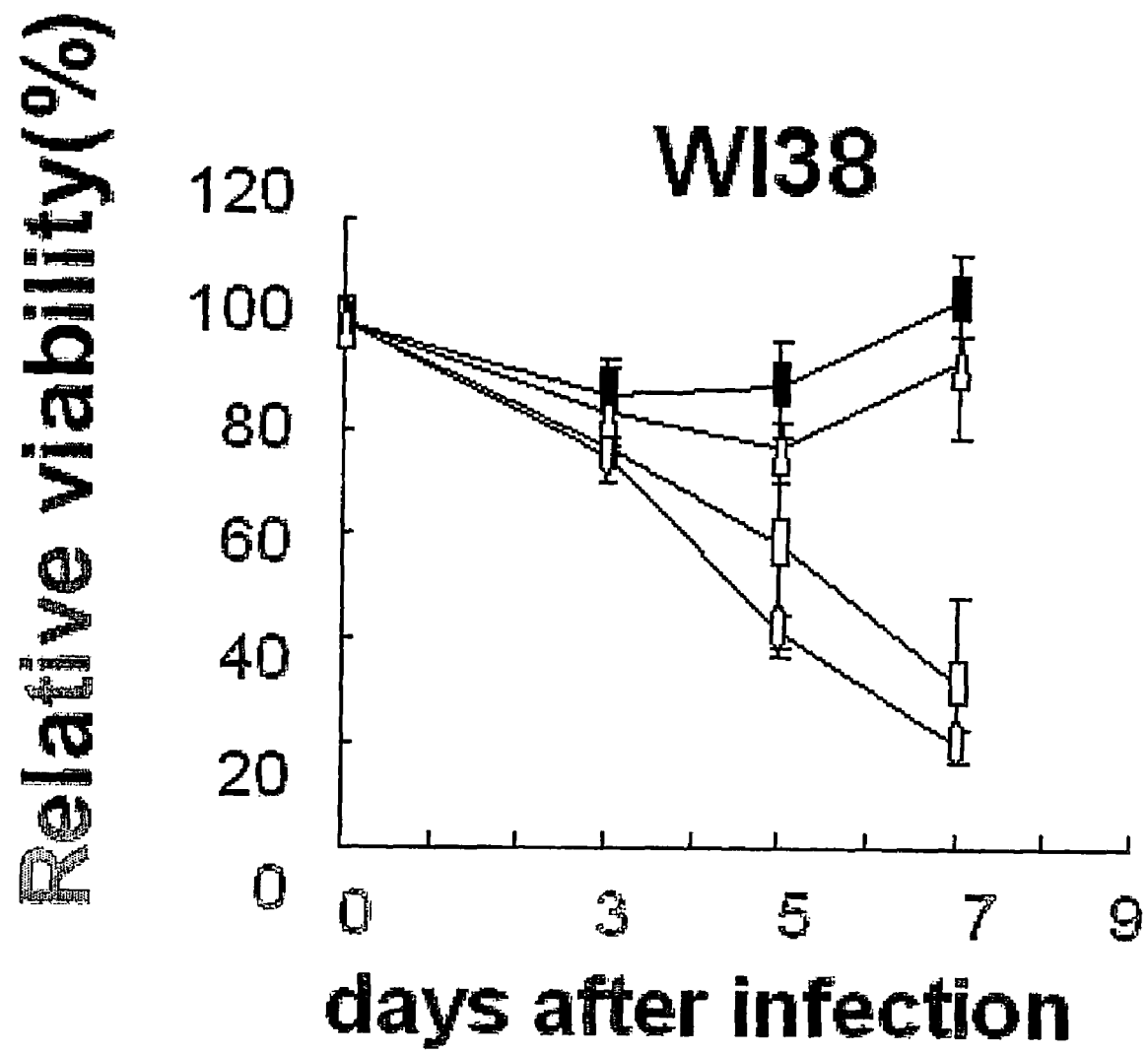
FIG. 8H is a graph showing results of quantitative analysis of the oncolytic effect on tumor cell line (WI38) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)
Figure 8:
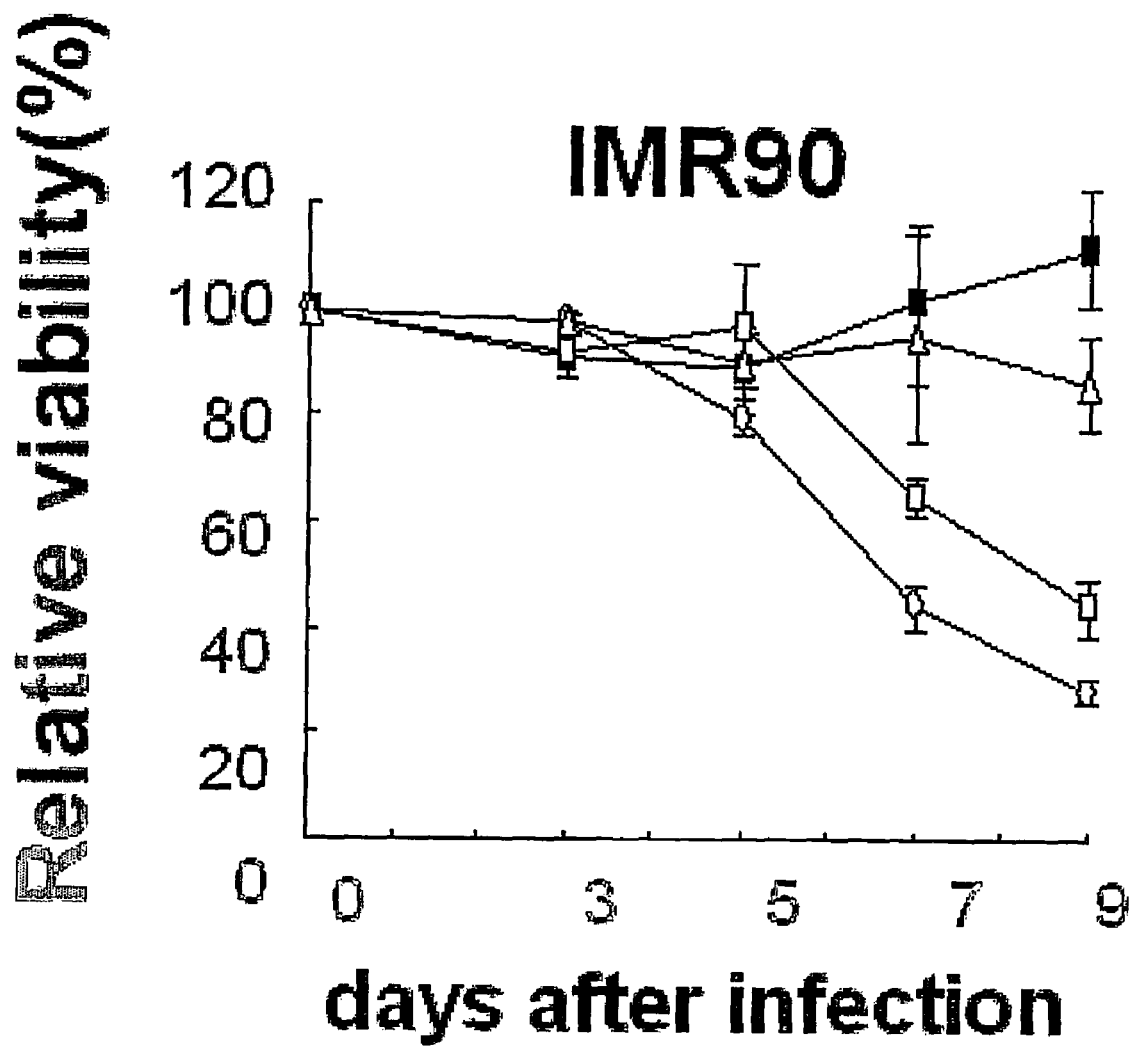
FIG. 8I is a graph showing results of quantitative analysis of the oncolytic effect on tumor cell line (IMR90) which is infected with the replication-competent recombinant adenoviral vectors according to the present invention (■: dl-CMV-Z, □: Ad-ΔE1B19, o: Ad-TERT-Δ19 and Δ: Ad-mTERT-Δ19)

As shown in FIGS. 8A to 8F, in all of the tested tumor cell lines, the Ad-TERT-Δ19, the Ad-mTERT-Δ19 and the Ad-ΔE1B19 were found to kill the tumor cells as time had been passed at similar levels to each other. In contrast, as shown in FIGS. 8G to 8I, in the normal cell lines, the cells showed cell viability (5-20%) sharply reduced as time had been passed in case of being infected with the Ad-ΔE1B19 and the Ad-TERT-Δ19. However, in case of being infected with the Ad-mTERT-Δ19, the normal cells of about higher than 90% were found to have survived even after 9 days of infection. These results demonstrate that the Ad-mTERT-Δ19 has excellent tumor cell-specific cytolytic effect and greatly improved stability in normal cells in comparison with the positive control of Ad-ΔE1B19 replication-competent adenovirus, and the Ad-TERT-Δ19 replication of which is regulated by the wild-type hTERT promoter.

EXAMPLE 8

Evaluation of the in vivo Antitumor Effect of the Replication-Competent Recombinant Adenoviruses The Ad-TERT-Δ19 adenovirus replication of which was regulated by the wild-type hTERT promoter and the Ad-mTERT-Δ19 replication of which was regulated by the m-hTERT promoter were evaluated for in vivo antitumor effect. The Ad-TERT-Δ19 and the Ad-mTERT-Δ19 adenoviruses were directly administered into tumors formed in nude mice inoculated with a human cervical carcinoma cell line, using the Ad-ΔE1B19 as a positive control, and tumor size was analyzed. In detail, $1\times10^7$ cells of the human cervical cell line C33A were intraperitoneally injected to postnatal 6-8 week-old nude mice. When tumors were grown to about 50-80 $mm^3$, the Ad-ΔE1B19, the Ad-TERT-Δ19 and the Ad-mTERT-Δ19 were directly injected to the tumors at a concentration of $5\times10^8$ plaque forming unit (pfu) three times at intervals of two days, with a negative control, PBS. Thereafter, tumor growth was monitored. The volume of the tumors was determined by measuring the long length and the short length using calipers and calculating tumor volume according to the following equation: tumor volume=(short length mm)$^2$×long axis mm×0.523.

Figure 9:
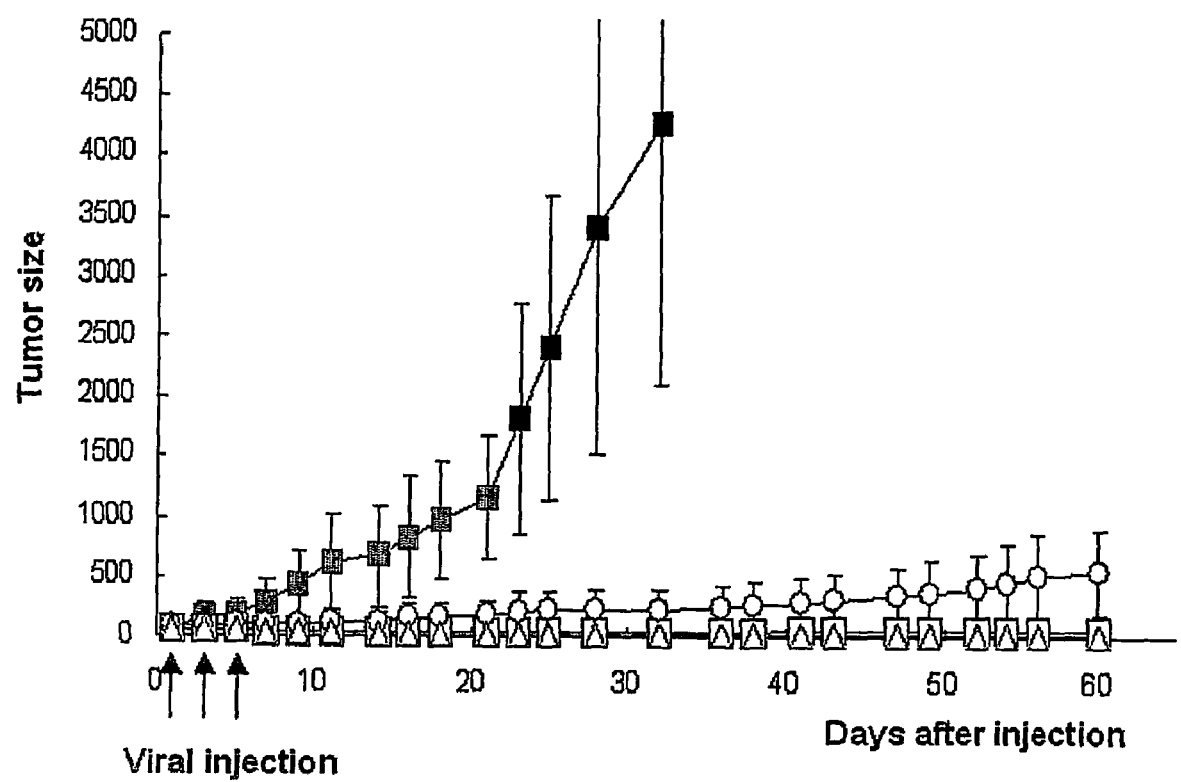
FIG. 9 is a graph showing oncolytic effect of the replication-competent recombinant adenoviral vectors according to the present invention on nude mice with established tumors (■: PBS, □: Ad-ΔE1B19, o: Ad-TERT-Δ19 and Δ: Ad-mTERT-Δ19)

As shown in FIG. 9, in the nude mice administered with PBS as a negative control, tumor size was rapidly grown to 4,232±2,185 $mm^3$ on day 32 after the intratumoral viral injection. In contrast, in the nude mice administered with the replication-competent adenoviruses, Ad-TERT-Δ19, Ad-mTERT-Δ19 and Ad-ΔE1B19, tumor growth greatly decreased. That is, on day 32 after the intratumoral viral injection, tumor size was 44±38 $mm^3$ in the nude mice administered with the Ad-ΔE1B19, while, in the nude mice administered with the Ad-TERT-Δ19 and the Ad-mTERT-Δ19, tumor size was 229±168 $mm^3$ and 18±20 $mm^3$, respectively ($p<0.05$). These results indicate that the replication-competent adenoviruses have potent antitumor effect. In addition, on day 60 after the viral administration, tumor growth could not be observed since all of the six nude mice administered with only PBS were killed. On day 60, the tumor size, in the nude mice administered with the Ad-ΔE1B19, the Ad-TERT-Δ19 and the Ad-mTERT-Δ19 and, was found to be 62±104 $mm^3$, 550±368 $mm^3$ and 15±15 $mm^3$, respectively ($p<0.05$). As apparent in these data, the Ad-mTERT-Δ19 adenovirus replication of which was regulated by the m-hTERT promoter had excellent antitumor effect that was similar to that of the Ad-ΔE1B19. In addition, in the case of being administered with the Ad-mTERT-Δ19, in two of five nude mice, the tumors completely disappeared on day 10 after the viral administration and were not re-grown even after two months.

EXAMPLE 9

Evaluation of Promoter Activity in vivo Normal Tissues of the hTERT and m-hTERT Promoters In order to evaluate the promoter activity of the hTERT and m-hTERT promoters in vivo normal tissues, the dl-TERT-Z and dl-mTERT-Z replication-deficient adenoviruses, which carried the LacZ marker gene respectively under the hTERT and m-hTERT promoter control, were intravenously administered into mice, using the dl-CMV-Z as a positive control. 100 μl of each of the adenoviruses of $5\times10^{10}$ PFU was injected to the tail vein of postnatal 6-8 week-old mice. After three days, organs (liver, heart, lung, spleen, kidney, stomach, testis and muscle) were excised from the mice. Each excised organ was fixed in 4% paraformaldehyde at 4° C. for 4-8 hrs, and dehydrated in a sucrose solution overnight. The dehydrated tissue was cryo-embedded in OCT compound (Sakura Finetec, Torrance, Calif.) and sectioned into sections 8 μm thick. Each tissue section was attached onto slide glasses coated with gelatin and stained with X-gal.

Figure 10A:
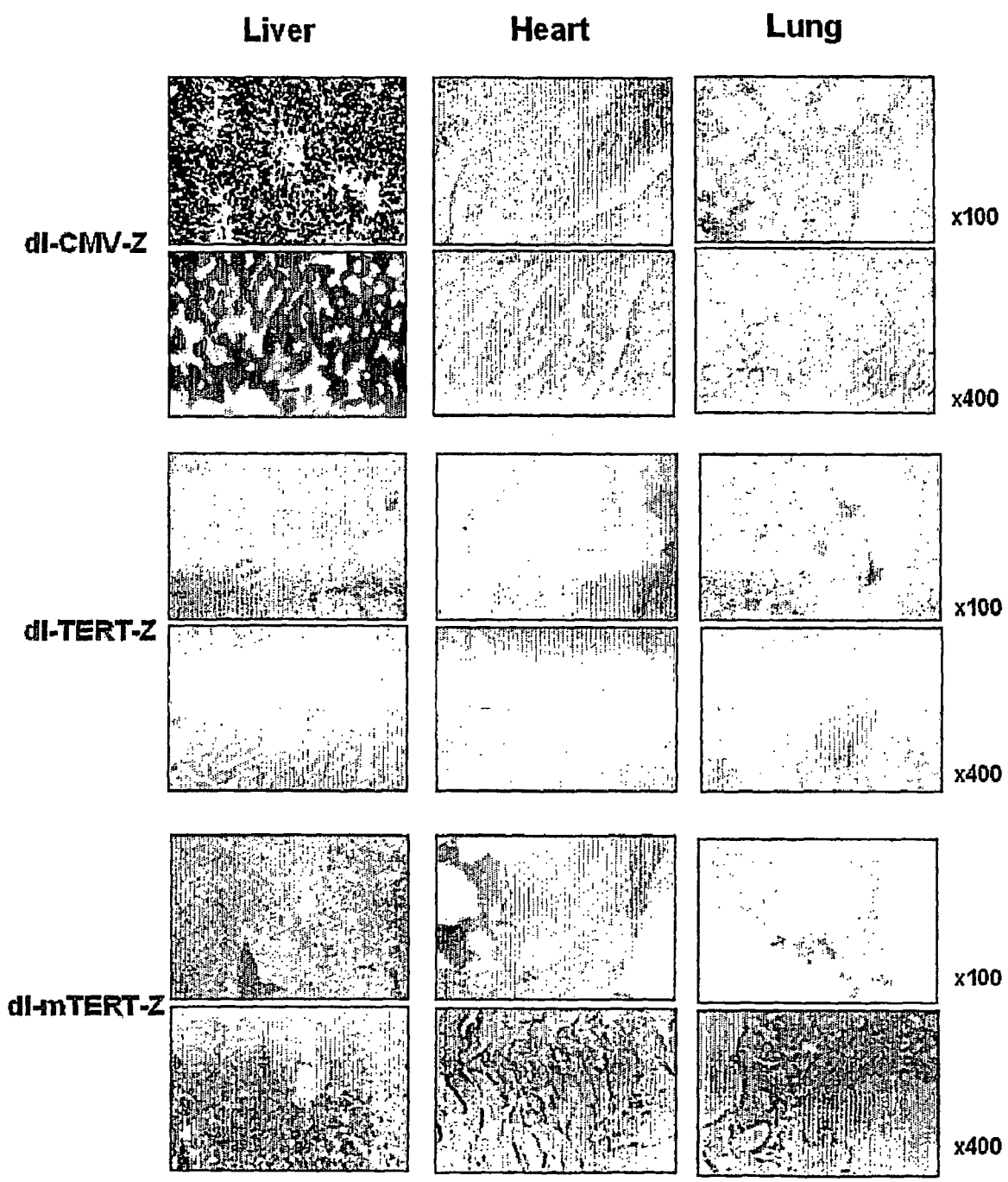
FIGS. 10A, 10B and 10C show expression patterns of the LacZ gene of the replication-deficient recombinant adenoviral vectors dl-CMV-Z, dl-TERT-Z and dl-mTERT-Z according to the present invention in various in vivo normal tissues.
Figure 10B:
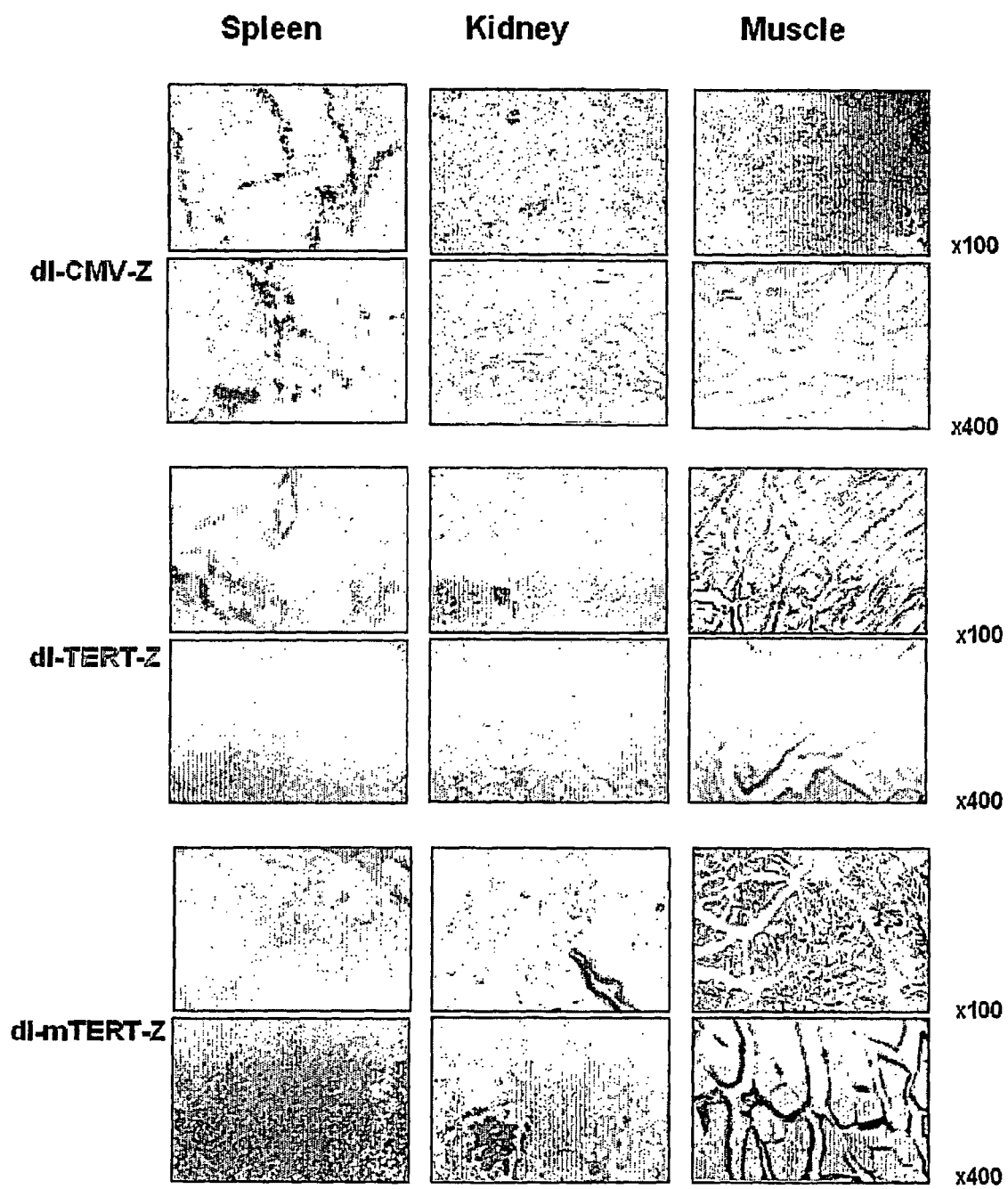
Figure 10C:
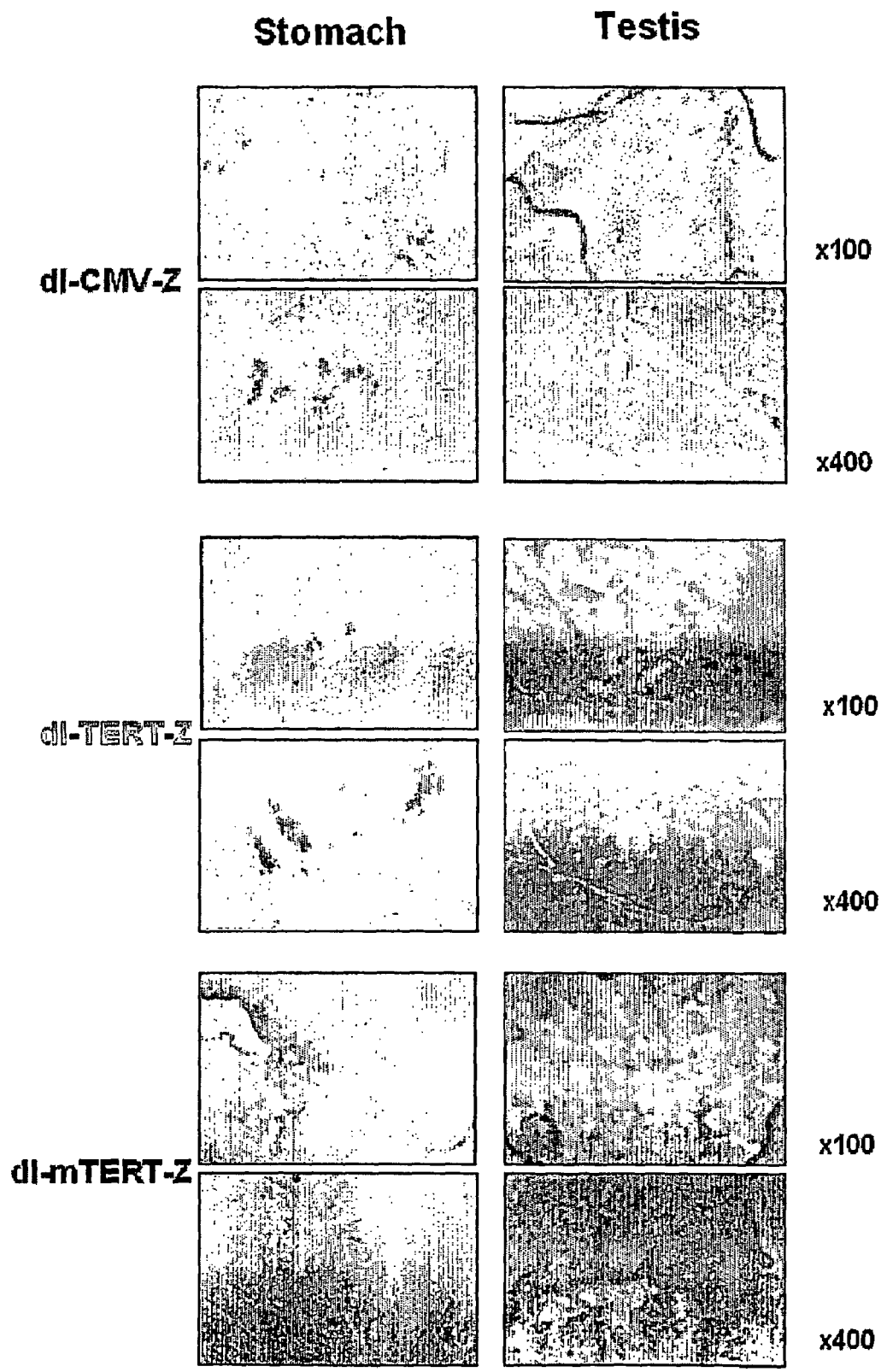

As shown in FIGS. 10A, 10B and 10C, in the case of the intravenous administration of the dl-CMV-Z adenovirus carrying the LacZ gene that was under the regulation of the constitutive promoter, the LacZ gene was expressed with extremely high levels in the liver, while being expressed with low levels in the spleen, the stomach and the kidney. However, in the case of the administration of the dl-TERT-Z and dl-mTERT-Z, the LacZ gene was absolutely not expressed in the liver, which was an organ in which adenoviruses were known to be most abundantly detected when intravenously administered into organs. These results indicated that the hTERT and m-hTERT promoters had no promoter activity in normal hepatic cells. In the spleen, the LacZ gene expression was very weak in the case of the administration of the dl-TERT-Z or the dl-mTERT-Z in comparison with the case of the administration of dl-CMV-Z, indicating that the promoter activity of the hTERT and m-hTERT promoters was suppressed also in the splenocytes. In the stomach, low expression of the LacZ gene was detected in the case of the administration of the dl-CMV-Z or the dl-TERT-Z, whereas no expression of the LacZ gene was observed in the case of the administration of the di-mTERT-Z. In the kidney, weak LacZ gene expression was found in the case of the administration of the dl-CMV-Z, whereas no expression of the LacZ gene was observed in the case of the administration of the dl-TERT-Z or the dl-mTERT-Z. These results demonstrate that the m-hTERT promoter has excellent tumor-specificity in vivo condition, too.

EXAMPLE 10

Evaluation of Promoter Activity of in vivo Tumor Tissues and Normal Tissues of the hTERT and m-hTERT Promoters The hTERT and m-hTERT promoters were evaluated for the promoter activity of in vivo tumor tissues and liver tissues, respectively. $1\times10^7$ cells of the human cervical cell line C33A were subcutaneously injected to postnatal 6-8 week-old nude mice. When tumors were grown to about 100 $mm^3$, the dl-TERT-Z and dl-mTERT-Z adenoviruses were intratumorally injected to the mice once at a concentration of $5\times10^8$ PFU, using the dl-CMV-Z as a negative control. After three days, the tumor tissues and the liver tissues were excised and stained with X-gal according to the same method as described above.

Figure 11A:
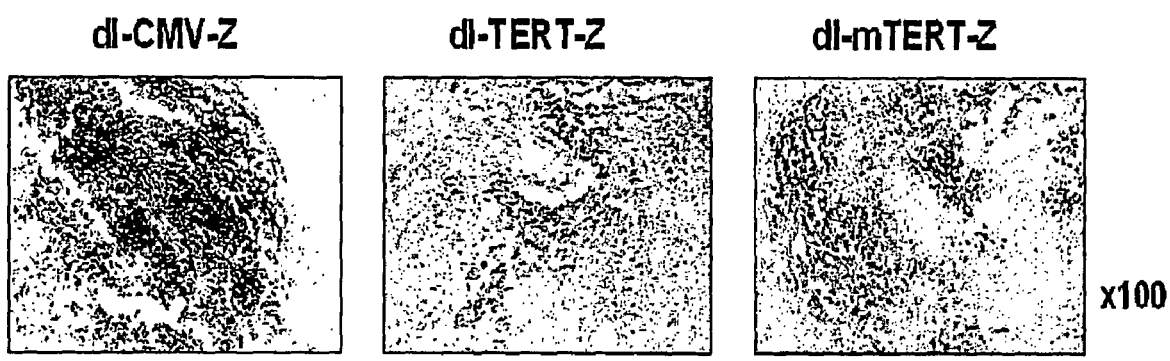
FIG. 11A shows expression patterns of the LacZ gene of the replication-deficient recombinant adenoviral vectors dl-CMV-Z, dl-TERT-Z and dl-mTERT-Z according to the present invention in in vivo tumor tissues.
Figure 11B:
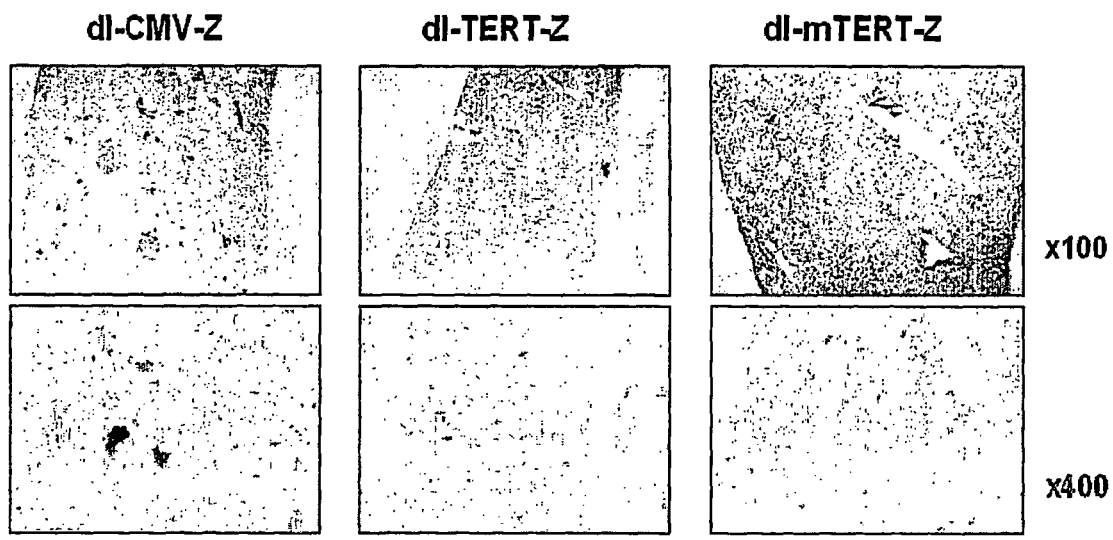
FIG. 11B shows LacZ gene expression patterns in the liver from mice intratumorally administered with the replication-deficient recombinant adenoviral vectors dl-CMV-Z, dl-TERT-Z and dl-mTERT-Z according to the present invention.

As shown in FIGS. 11A and 11B, in the mice intratumorally injected with the dl-CMV-Z, the LacZ gene was expressed with high levels in tumor tissues and also expressed in the normal liver tissue. In contrast, in the mice administered with the dl-TERT-Z and the dl-mTERT-Z, high expression of the LacZ gene was detected in tumor tissues, whereas no LacZ gene expression was observed in the normal liver tissue. In addition, the dl-TERT-Z adenovirus induced the LacZ gene expression only in a very small portion of tumor cells, whereas the dl-mTERT-Z adenovirus induced the LacZ gene expression in a large portion of tumor cells in tumor tissues. These results indicate that the m-hTERT promoter has stronger promoter activity in tumor cells than the wild-type hTERT promoter.

EXAMPLE 11

Comparison of Viral Production Yield in Tumor Cells and Normal Cells

In order to compare viral production yield by tumor cell-specific replication by the hTERT or m-hTERT promoter in tumor cells and normal cells, tumor cells (HeLa cells) and normal cells (BJ cells) were aliquotted onto 6-well plates at a density of $3\times10^5$ cells per well, and, next day, infected with the Ad-ΔEiB19, the Ad-TERT-Δ19, the Ad-mTERT-Δ19 and the replication-deficient dl-CMV-Z as a negative control at an MOI of 10 for 4 hrs. Then, the culture medium containing the viruses was removed and replaced by a new medium, and cells and culture supernatants were collected at regular time intervals. After freezing and thawing of three times, viral titers were determined in 293 cells by the limiting titration method.

Figure 12A:
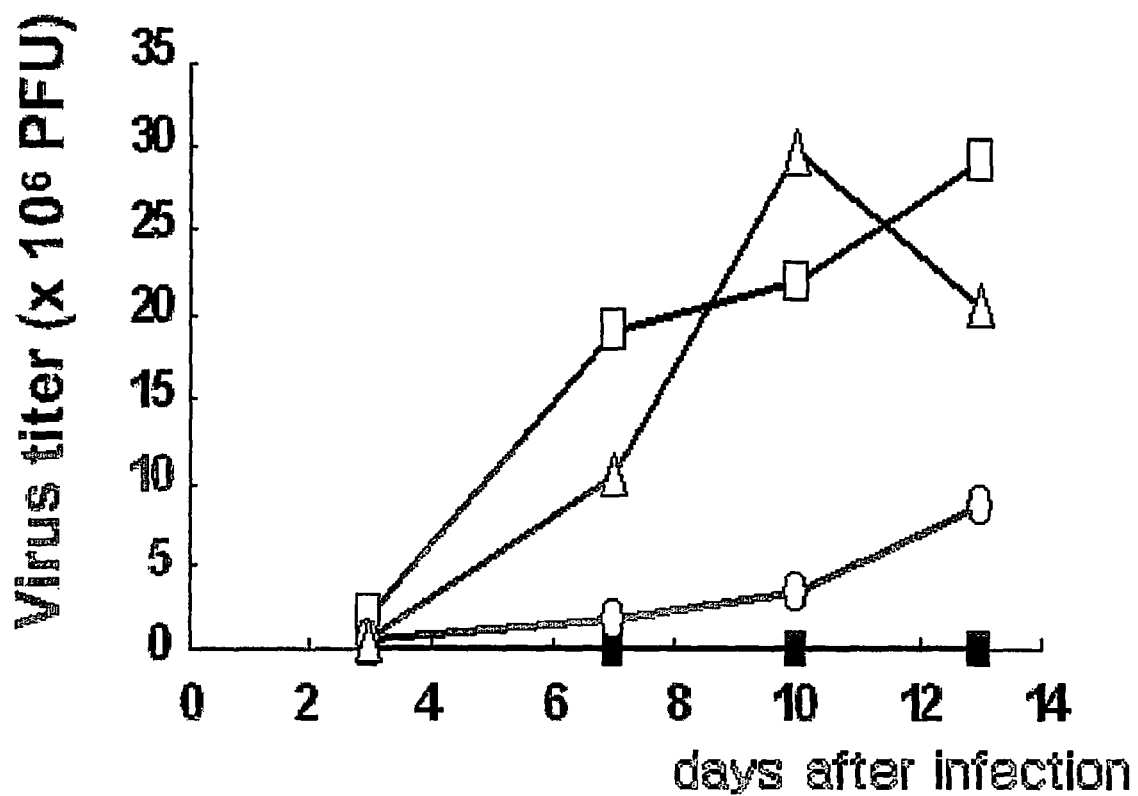
FIG. 12A is a graph showing viral production yields of the replication-competent recombinant adenoviral vectors according to the present invention in the tumor cell line HeLa (□: Ad-ΔE1B19, o: Ad-TERT-Δ19, Δ: Ad-mTERT-Δ19 and ■: dl-CMV-Z)
Figure 12B:
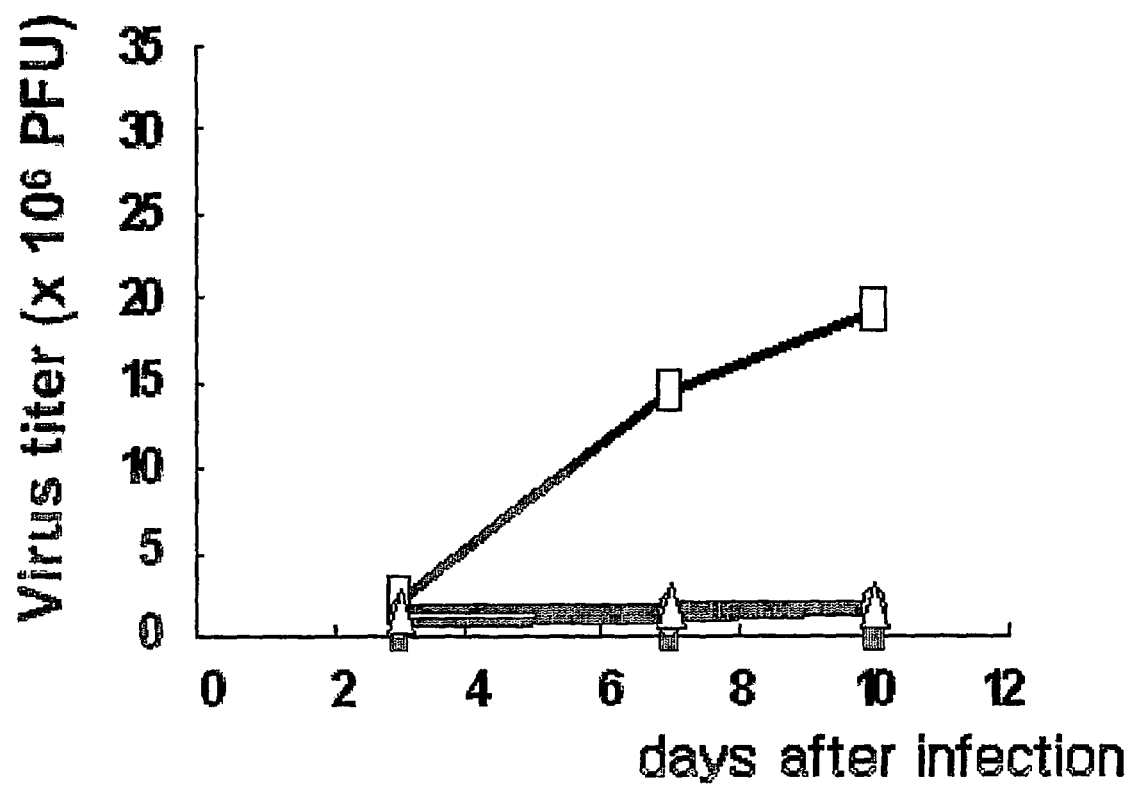
FIG. 12B is a graph showing viral production yields of the replication-competent recombinant adenoviral vectors according to the present invention in the normal cell line BJ(□: Ad-ΔE1B19, o: Ad-TERT-Δ19, Δ: Ad-mTERT-Δ19 and n: dl-CMV-Z)

As shown in FIGS. 12A and 12B, in the HeLa cells infected with the Ad-mTERT-Δ19, viruses were actively produced with the similar yield to the case of being infected with the Ad-ΔE1B19. In contrast, when the HeLa cells were infected with the Ad-TERT-Δ19, the viral production yield was remarkably reduced. However, when the human normal BJ cells were infected with the Ad-mTERT-Δ19, viral production was rarely detected, indicating that this adenovirus has also tumor cell-specific replication ability.

EXAMPLE 12

Evaluation of Replication Ability of the Replication-Competent Adenoviruses in Tumor Tissues $1\times10^7$ cells of the human cervical cell line C33A were subcutaneously injected to postnatal 6-8 week-old nude mice. When tumors were grown to about 50-80 mm$^3$, the Ad-ΔE1B19, the Ad-TERT-Δ19 and the Ad-mTERT-Δ19 adenoviruses were intratumorally injected to the mice at a concentration of $5\times10^8$ PFU. After seven days, the tumors were excised and embedded in paraffin. The paraffin blocks were subjected to immunohistochemistry with an antibody selectively binding to the adenovirus hexon region. The paraffin blocks were hybridized with the antibody selectively binding to the adenovirus hexon protein (AB1056F: Chemicon, Temecula, Calif., USA) as a primary antibody, and then with an HRP (horse radish peroxidase)-conjugated secondary antibody to analyze expression patterns of the hexon.

Figure 13:
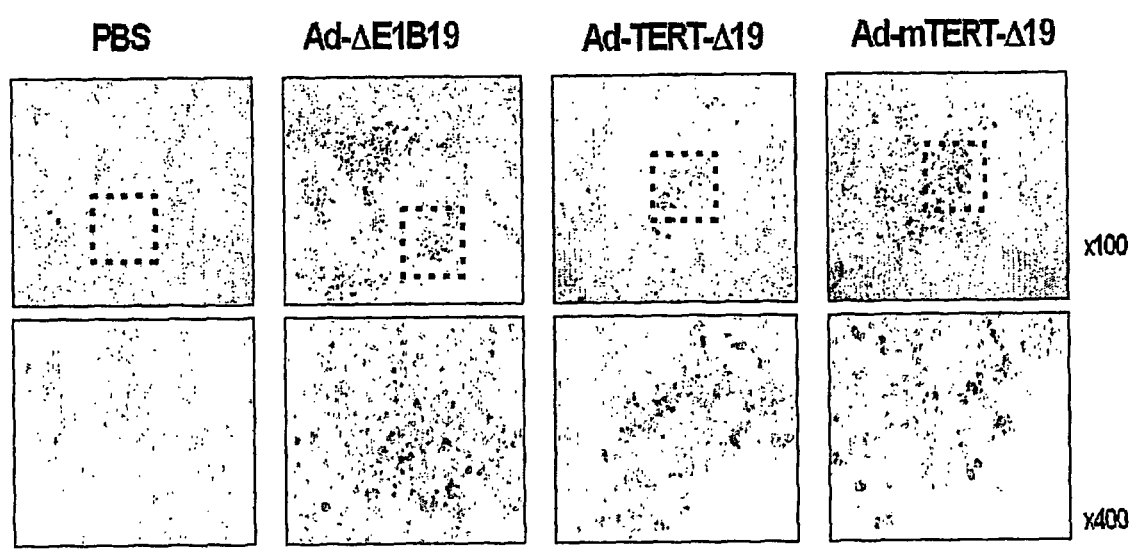
FIG. 13 shows results of immunohistochemistry for comparison of replication ability in tumor tissues of the replication-competent recombinant adenoviral vectors Ad-ΔE1B19, Ad-TERT-Δ19 and Ad-mTERT-Δ19 according to the present invention.

As shown in FIG. 13, adenovirus was detected in wider region of the tumor tissues injected with the Ad-ΔE1B19 and the Ad-mTERT-Δ19, than the case of being injected with the Ad-TERT-Δ19. These results indicate that the Ad-mTERT-Δ19 has higher replication ability in tumor tissues than the Ad-TERT-Δ19.

EXAMPLE 13

Evaluation of Cytotoxicity of the Replication-Competent Adenoviruses Against the Liver First, the human cervical cell line C33A was inoculated to nude mice. Into developed tumors in the mice, each of the Ad-mTERT-Δ19 and the Ad-ΔE1B19 adenoviruses was injected. After seven days, the liver tissues were excised from the mice, and stained with hematoxylin-eosin for histologic analysis.

Figure 14:
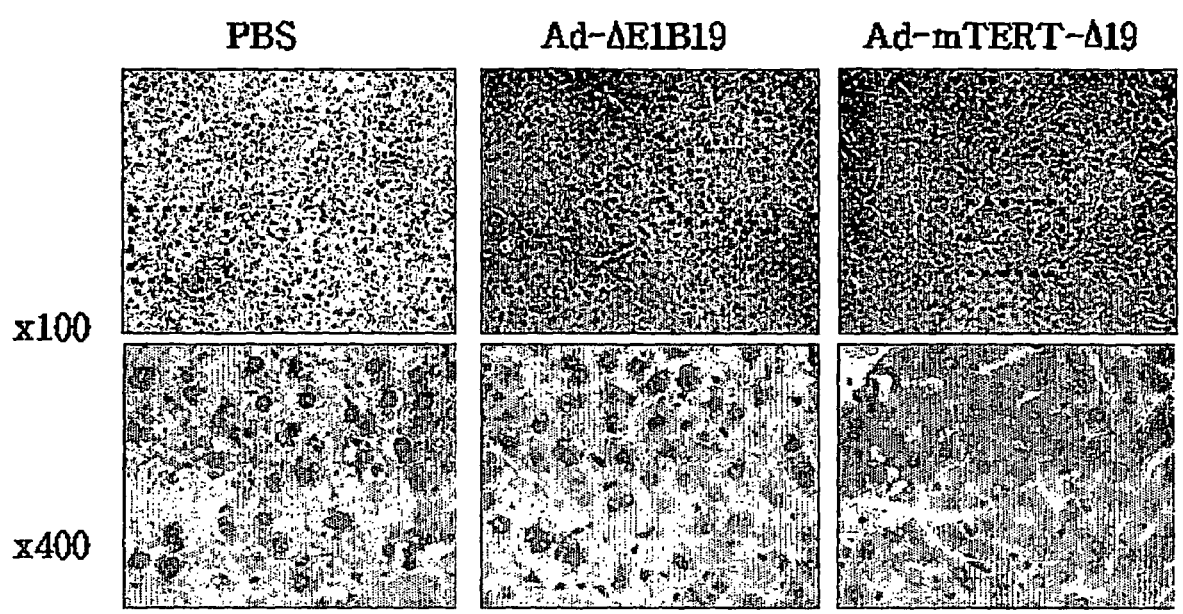
FIG. 14 shows results of Hematoxylin-eosin staining for comparison of toxicity to normal liver of the replication-competent recombinant adenoviral vectors Ad-ΔE1B19 and: Ad-mTERT-Δ19 according to the present invention.

As shown in FIG. 14, in the liver of the mice administered with the Ad-ΔE1B19, many cells underwent mitosis while the nuclei were enlarged and darkly stained, indicating that the nuclei were damaged by the virus. In addition, Kupffer cell proliferation, a large number of inflammatory cells and cells undergoing apoptosis were observed. In contrast, in the liver of the mice administered with the Ad-mTERT-Δ19, although the nuclei were slightly enlarged, no cells undergoing mitosis were observed, and Kupffer cells had the normal morphology. Also, this liver did not show reactive hepatitis and inflammation. These results indicate that the Ad-mTERT-Δ19 adenovirus has a very low cytotoxicity in comparison with the Ad-ΔE1B19 in liver tissue.

EXAMPLE 14

Evaluation of Mortality of Mice According to the Amount and Route of the Administration of Adenovirus The tumor-specifically replication-competent adenovirus Ad-mTERT-Δ19 and the control virus Ad-ΔE1B19 were evaluated for in vivo toxicity according to the amount of its administration through various administration routes.

A. Toxicity of Intravenous Administration of the Viruses

Figure 15A:
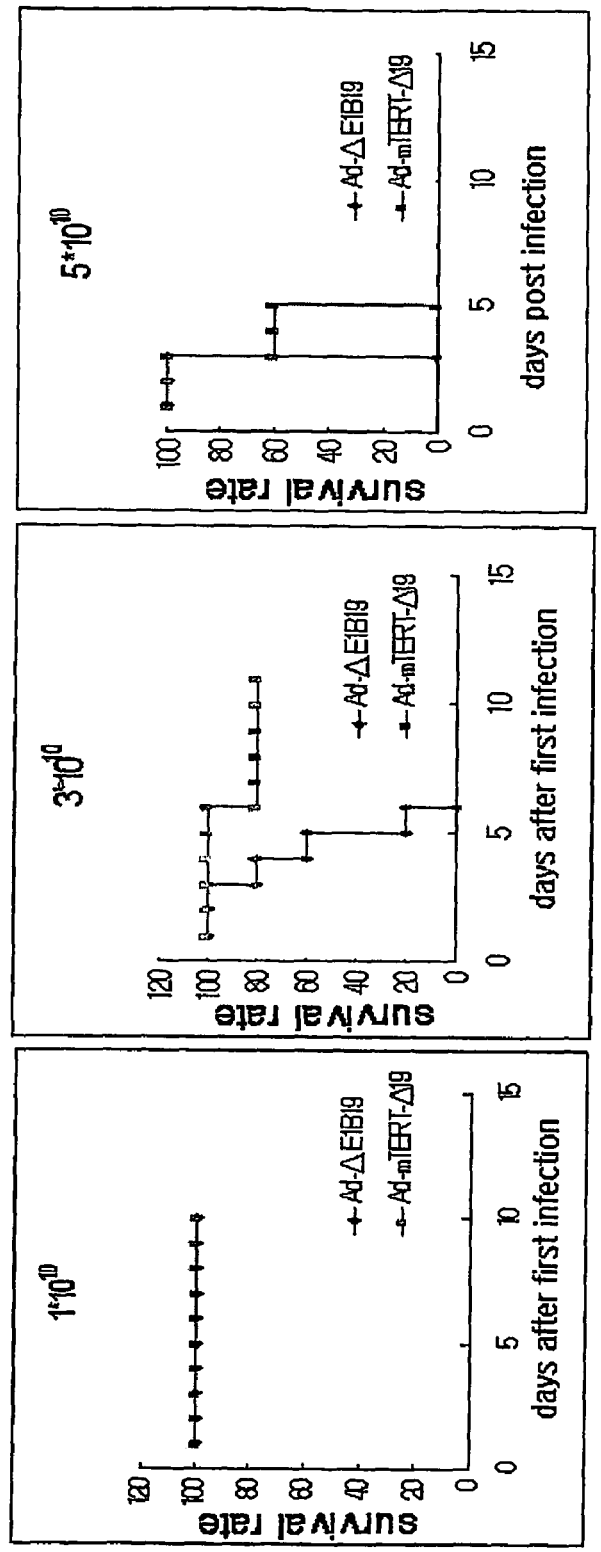
FIG. 15A is a graph showing mouse viability according to the amount of administration of the replication-competent recombinant adenoviral vectors Ad-ΔE1B19 and Ad-mTERT-Δ19 according to the present invention, when the adenoviral vectors were administered intravenously.

In order to investigate toxicity of administration into the mouse tail vein of adenovirus according to the amount of the administration, postnatal 6-8 week-old mice were injected through the tail vein with the Ad-ΔE1B19 or Ad-mTERT-Δ19 at various concentrations of $1\times10^{10}$, $3\times10^{10}$ and $5\times10^{10}$ PFU, respectively, or 100 µl of PBS, and mouse viability was then investigated (FIG. 15A).

When intravenously administered with $1\times10^{10}$ PFU of the Ad-ΔE1B19 or the Ad-mTERT-Δ19, all of the tested ten mice were survived until day 15 after the viral administration. That is, the systemic administration via the intravenous route of $1\times10^{10}$ PFU of the viruses caused zero mortality in mice. When systemically administered with the $3\times10^{10}$ PFU, in case of the Ad-mTERT-Δ19, four of five mice were survived until day 15 after the viral administration, whereas, in case of the Ad-ΔE1B19, all of five mice were killed within day 8 after the viral administration. That is, in the $3\times10^{10}$ PFU, the Ad-ΔE1B19 lacking tumor-specificity was toxic to mice because of showing 100% mortality, whereas the Ad-mTERT-Δ19 with tumor-specificity showed 20% mortality and thus identified to have attenuated toxicity. In the $5\times10^{10}$ PFU, all mice administered with the Ad-ΔE1B19 or the Ad-mTERT-Δ19 were killed within day 5 after the viral administration, indicating that such a high titer of the viruses is highly toxic upon systemic administration via the intravenous route.

B. Toxicity of Intraperitoneal Administration of the Viruses

Figure 15B:
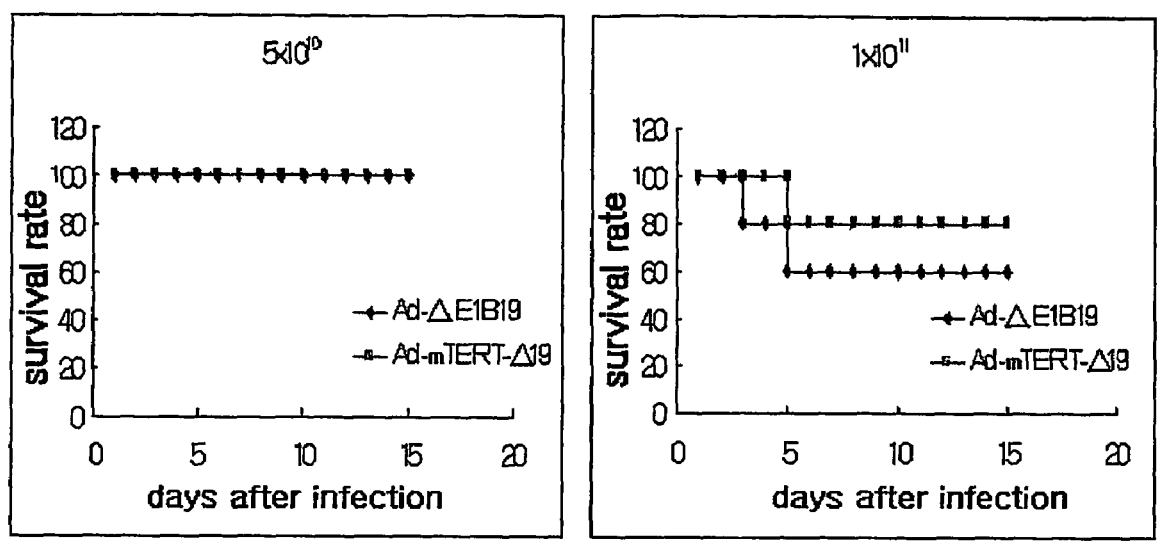
FIG. 15B is a graph showing mouse viability according to the amount of administration of the replication-competent recombinant adenoviral vectors Ad-ΔE1B19 and Ad-mTERT-Δ19 according to the present invention, when the adenoviral vectors were administered intraperitoneally.

In order to investigate toxicity of intraperitoneal administration of adenovirus according to the amount of the administration, postnatal 6-8 week-old mice were injected intraperitoneally with 1 ml of the Ad-Δ19 or the Ad-mTERT-Δ19 at concentrations of $5\times10^{10}$ and $1\times10^{11}$ PFU, and mouse viability was then investigated (FIG. 15B).

When intraperitoneally administered with $5\times10^{10}$ PFU of the Ad-Δ19 or the Ad-mTERT-Δ19, all of the tested ten mice were survived until day 15 after the viral administration. That is, the intraperitoneal administration of the $5\times10^{10}$ PFU of the viruses caused zero mortality in mice. When intraperitoneally administered with $1\times10^{11}$ PFU, in case of the Ad-mTERT-Δ19, four of five mice were survived until day 15 after the viral administration, whereas, in case of the Ad-ΔE1B19, three of five mice were survived within day 15 after the viral administration. That is, the Ad-ΔE1B19 lacking tumor-specificity showed 40% mortality, whereas the Ad-mTERT-Δ19 with tumor-specificity showed 20% mortality and thus identified to have attenuated toxicity. In the case of the $5\times10^{10}$ PFU, as described above, when systemically administered via the intravenous route with the viruses, all mice were found to be killed within day 5 after the viral administration. In contrast, in the same PFU, the intraperitoneal administration displayed zero mortality in mice. These results indicate that adenovirus is safer when it is administered by the intraperitoneal route than by the intravenous route.

C. Toxicity of Intratumoral Administration of the Viruses

Figure 15C:
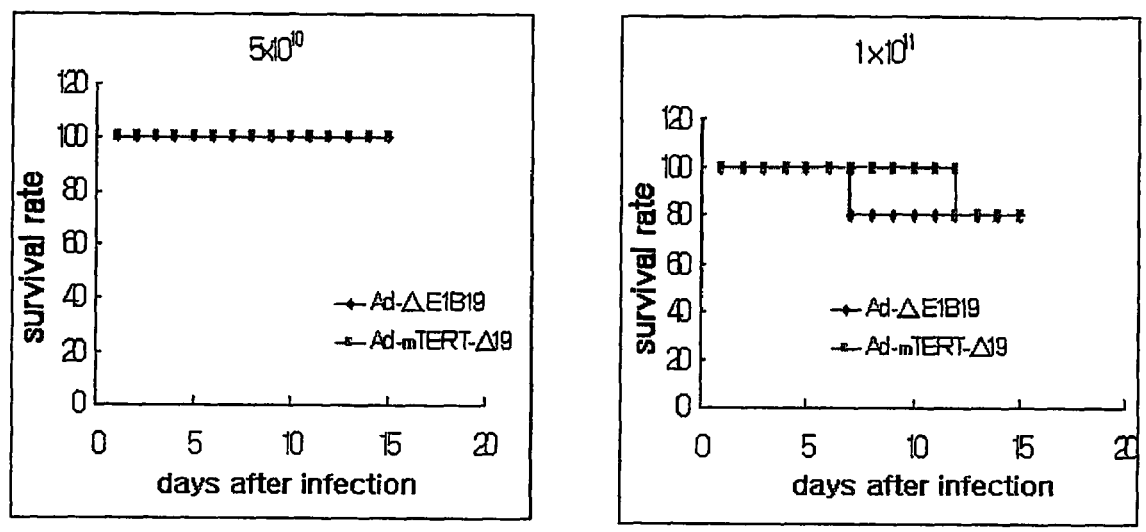
FIG. 15C is a graph showing mouse viability according to the amount of administration of the replication-competent recombinant adenoviral vectors Ad-ΔE1B19 and Ad-mTERT-Δ19 according to the present invention, when the adenoviral vectors were administered intratumorally.

In order to investigate toxicity of intratumoral administration of adenovirus according to the amount of the administration, B16F10 cells were intraperitoneally injected to postnatal 6-8 week-old mice. When tumors were grown to about 100 mm³, the Ad-ΔE1B19 and the Ad-TERT-Δ19 adenoviruses were intratumorally injected to the mice at a concentration of $5\times10^{10}$ PFU and $1\times10^{11}$ PFU (FIG. 15C).

All of the tested twenty mice were survived until day 15 after the viral administration. That is, the intratumoral administration of the $5\times10^{10}$ PFU of the viruses caused zero mortality in mice. When intratumorally administered with the $1\times10^{11}$ PFU, in case of the Ad-ΔE1B19, two of the tested ten mice were killed on day 8 after the viral administration, while, in case of the Ad-mTERT-Δ19, two of the tested tem mice were killed within day 12 after the viral administration. That is, for the test period of 15 days, the two cases showed the same mortality of 20% to each other. However, the mice administered with the Ad-mTERT-Δ19 survived for a longer time than the mice administered with the Ad-ΔE1B19.

Taken together, upon the intravenous or intraperitoneal administration, the tumor-specifically replicating Ad-mTERT-Δ19 showed a reduction in mouse mortality in comparison with the Ad-Δ19 adenovirus lacking tumor-specificity, indicating that the in vivo toxicity by the Ad-mTERT-Δ19 is attenuated by such administration routes. In addition, in the same PFU of the adenoviruses, the systemic administration via the intravenous route can cause stronger toxicity of the adenoviruses and eventually higher mortality, than the intraperitoneal and intratumoral administration.

EXAMPLE 15

Figure 16A:
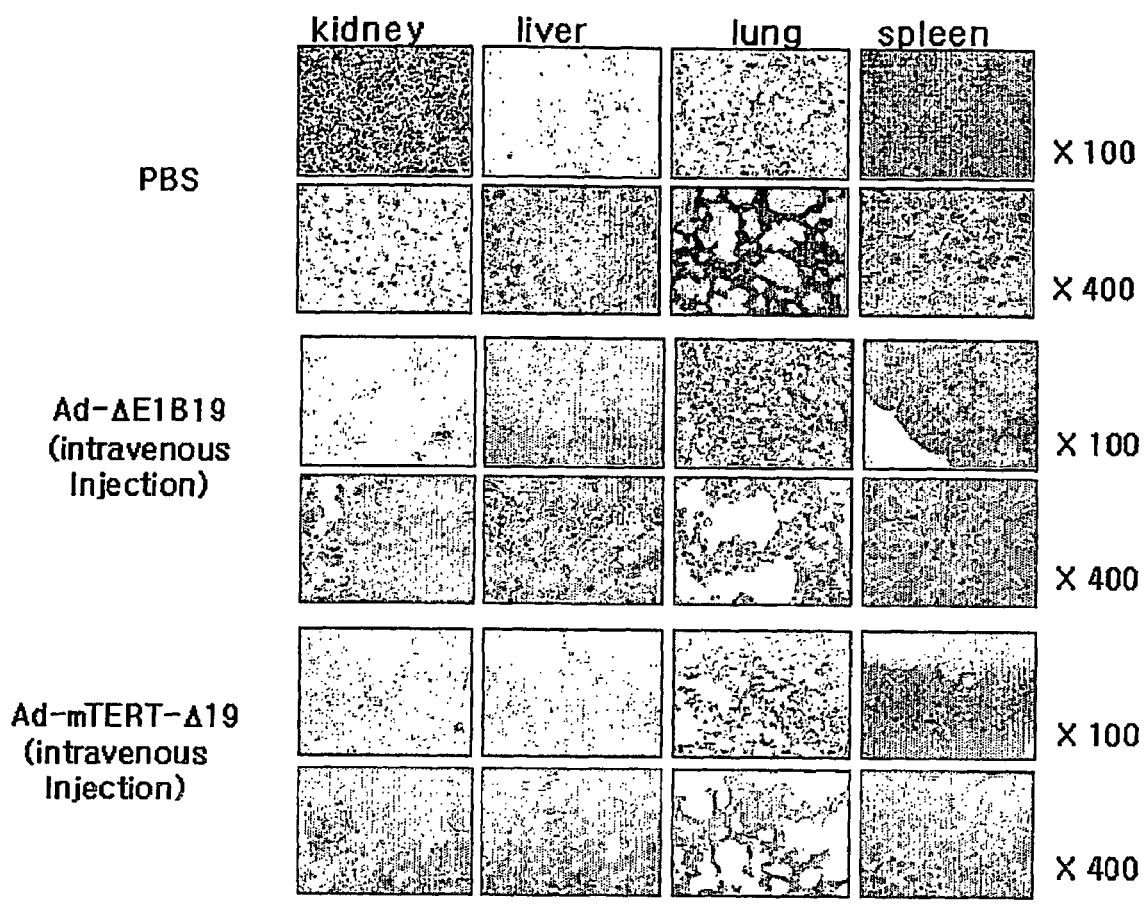
FIG. 16A is a photograph showing toxicity to normal tissues according to the amount of administration of the replication-competent recombinant adenoviral vectors Ad-ΔE1B19 and Ad-mTERT-Δ19 according to the present invention, when the adenoviral vectors were administered intravenously.
Figure 16B:
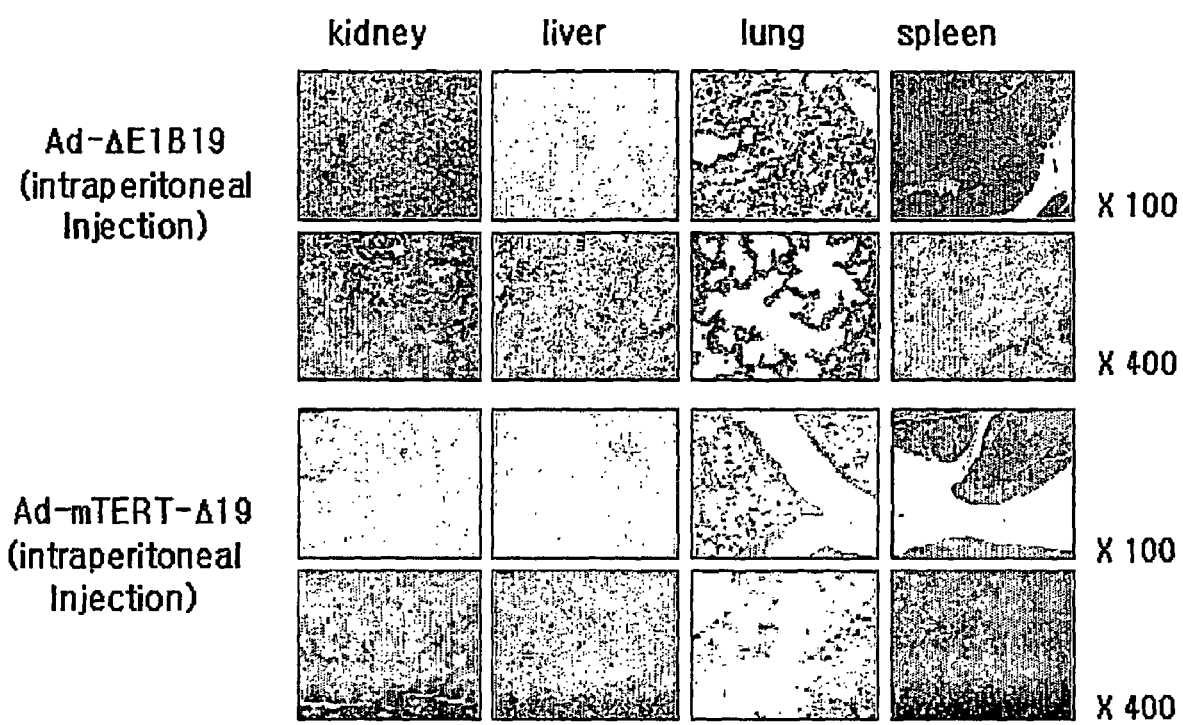
FIG. 16B is a photograph showing toxicity to normal tissues according to the amount of administration of the replication-competent recombinant adenoviral vectors Ad-ΔE1B19 and Ad-mTERT-Δ19 according to the present invention, when the adenoviral vectors were administered intraperitoneally.
Figure 16C:
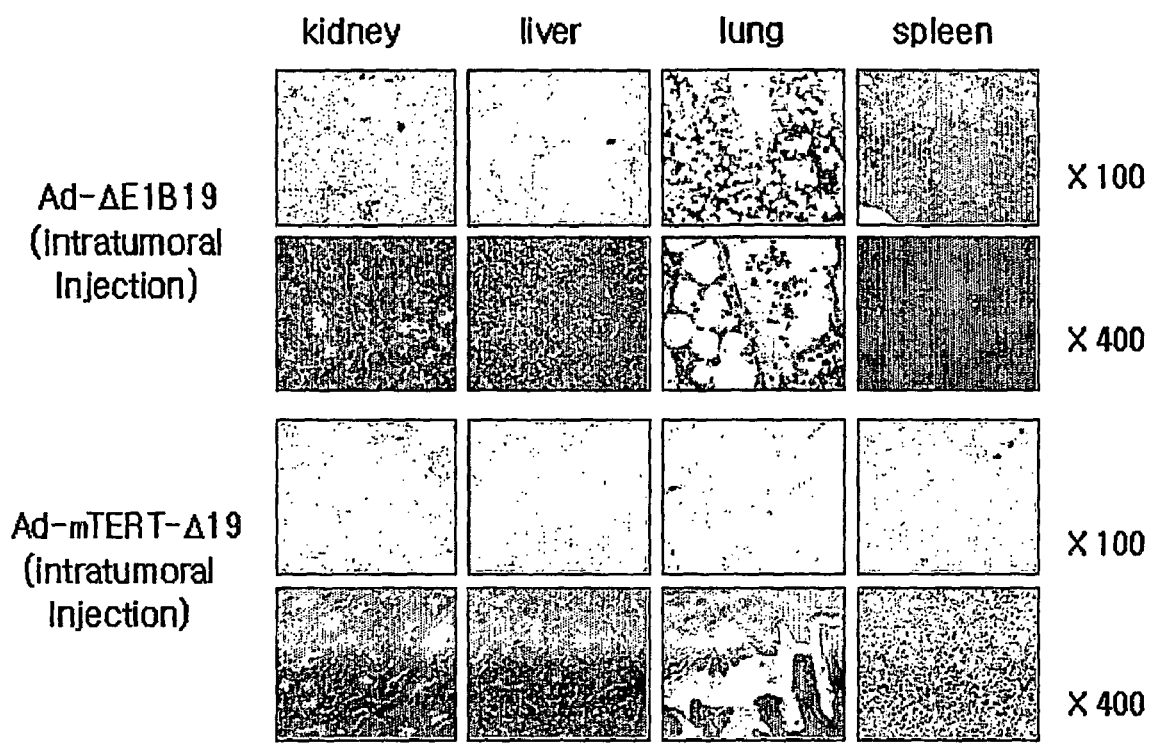
FIG. 16C is a photograph showing toxicity to normal tissues according to the amount of administration of the replication-competent recombinant adenoviral vectors Ad-ΔE1B19 and Ad-mTERT-Δ19 according to the present invention, when the adenoviral vectors were administered intratumorally.

Evaluation of Toxicity According to the Route of the Administration of Adenovirus in Normal Tissues The tumor-specific, replication-competent Ad-mTERT-Δ19 and a control virus Ad-ΔE1B19 were evaluated for in vivo toxicity according to the route of administration with respect to pathology. Postnatal 6-8 week mice were administered via the tail vein, intraperitoneally or intratumorally with $1\times10^{10}$ PFU of the Ad-mTERT-Δ19 or the Ad-ΔE1B19 or PBS. After seven days, organs (kidney, liver, lung and spleen) were excised from the mice, cryo-embedded and stained with hematoxylin-eosin (H&E) for histologic analysis (FIGS. 16A to 16C).

In the liver of the mice intravenously administered with the Ad-ΔE1B19, severe inflammation was observed in the surroundings of the hepatic portal vein, Kupffer cell proliferation and cells undergoing apoptosis were also observed. Also, a high percentage of mitosis and the enlarged and darkly stained nuclei indicated that the nucleus was damage by the administered virus. Moreover, lymphocytes were not observed in the reticulum cells of lymphoid follicles. However, in the liver of the mice systemically administered with the Ad-mTERT-Δ19 via the intravenous route, weak inflammation and slightly enlarged nuclei were observed, but cells undergoing mitosis were not found. Also, in other tissues, such abnormalities were not observed. When the Ad-mTERT-Δ19 or the Ad-ΔE1B19 adenovirus was not systemically administered via the intravenous route but intraperitoneally or intratumorally administered at the same titer, all of the excised tissues were found to be at normal states. Taken together, the systemic administration of the adenoviruses was found to cause severe toxicity in comparison with the intraperitoneal or intratumoral administration. In addition, the Ad-mTERT-Δ19 adenovirus replication of which was regulated in a tumor-specific manner was found to have much lower in vivo toxicity to biological tissues than the Ad-ΔE1B19.

EXAMPLE 16

Evaluation of Toxicity According to the Amount and Route of the Administration of Adenovirus by Blood Assay In vivo toxicity of the adenoviruses was further investigated by analyzing blood samples collected from the mice administered with the adenoviruses. In this test, hepatic function-related enzymes (GOT, GPT and T-bililubin), renal function parameters (blood urea nitrogen (BUN), Creatine and uric acid), total cholesterol and electrolytes ($Na^+$, $K^+$ and $Cl^-$) were quantitatively measured (Tables 2 to 4).

A. Administration of the Adenoviruses of $1\times10^{10}$ or $5\times10^{10}$ PFU Via Various Routes When mice were systemically administered via the tail vein with the Ad-mTERT-Δ19 or the Ad-ΔE1B19 adenovirus of $5\times10^{10}$ PFU, the mice were killed within seven days after the viral administration, and thus, could not be subjected to blood analysis. In contrast, when the adenovirus of the same titer was intraperitoneally or intratumorally administered, on day 7 after the viral administration, severe hepatic toxicity occurred. However, in this case, no renal toxicity was observed, and the electrolytes were present within normal levels. These results indicate that the intraperitoneal or intratumoral administration of the adenoviruses was safer than the intravenous administration.

When systemically administered to mice at a concentration of $1\times10^{10}$ PFU, the adenoviruses were evaluated whether causing hepatic toxicity in the mice. In mice administered with the Ad-ΔE1B19, GOT and GPT levels were remarkably increased while exceeding the analyzable maximum levels. In contrast, when administered with the Ad-mTERT-Δ19, mice showed about 5-16-fold higher GOT and GPT levels than normal levels. However, the level of another hepatic function marker enzyme T-bililubin was found to be greatly increased in the mice administered with the Ad-ΔE1B19 while being within the normal range in the mice administered with the Ad-mTERT-Δ19.

In addition, when mice were intraperitoneally administered with the Ad-ΔE1B19 adenovirus of $5\times10^{10}$ PFU, the mice displayed increased GPT levels. In contrast, in mice intraperitoneally administered with the Ad-mTERT-Δ19 of the same titer, GPT levels were in the normal range. When these adenoviruses were intratumorally administered, GOT and T-bililubin levels were increased in mice administered with the Ad-ΔE1B19. These results indicate that the tumor-specific replication-competent adenovirus has decreased hepatic toxicity in vivo in comparison with the adenovirus with no tumor-specificity.

TABLE 2

Analysis of blood samples from mice intravenously administered with adenoviruses of $1 \times 10^{10}$ PFU

| Description | Test | Unit | PBS | Ad-ΔE1B19 | Ad-mTERT-Δ19 |
|---|---|---|---|---|---|
| Hepatic function test | GOT | U/L | 176 | >1000 | 914 |
|  | GPT | U/L | 48 | >1000 | 792 |
|  | T-bililubin | U/L | 0.9 | 22.0 | 1.3 |
| Renal function test | BUN | mg/dl | 18.2 | 20.8 | 16.2 |
|  | Creatine | mg/dl | 0.3 | 0.8 | 0.4 |
| Lipid test | Total chloesterol | mg/dl | 110 | 257 | 124 |
| Electrolyte test | Na⁺ | mEq/dl | 114 | 145 | 143 |
|  | K⁺ | mEq/dl | 4.3 | 4.2 | 4.3 |
|  | Cl⁻ | mEq/dl | 96 | 97 | 98 |

TABLE 3

Analysis of blood samples from mice intraperitoneally administered with adenoviruses of $5 \times 10^{10}$ PFU

| Description | Test | Unit | PBS | Ad-ΔE1B19 | Ad-mTERT-Δ19 |
|---|---|---|---|---|---|
| Hepatic function test | GOT | U/L | 176 | 166 | 101 |
|  | GPT | U/L | 48 | 109 | 24 |
|  | T-bililubin | U/L | 0.9 | 0.6 | 0.5 |
| Renal function test | BUN | mg/dl | 18.2 | 24.8 | 18 |
|  | Creatine | mg/dl | 0.3 | 0.3 | 0.2 |
| Lipid test | Total chloesterol | mg/dl | 110 | 128 | 132 |
| Electrolyte test | Na⁺ | mEq/dl | 144 | 143 | 144 |
|  | K⁺ | mEq/dl | 4.3 | 4.3 | 4.3 |
|  | Cl⁻ | mEq/dl | 96 | 96 | 98 |

TABLE 4

Analysis of blood samples from mice intratumorally administered with adenoviruses of $5 \times 10^{10}$ PFU

| Description | Test | Unit | PBS | Ad-ΔE1B19 | Ad-mTERT-Δ19 |
|---|---|---|---|---|---|
| Hepatic function test | GOT | U/L | 176 | 372 | 132 |
|  | GPT | U/L | 48 | 45 | 19 |
|  | T-bililubin | U/L | 0.9 | 3.5 | 0.7 |
| Renal function test | BUN | mg/dl | 18.2 | 19.6 | 23.1 |
|  | Creatine | mg/dl | 0.3 | 0.4 | 0.4 |
| Lipid test | Total chloesterol | mg/dl | 110 | 117 | 130 |
| Electrolyte test | Na⁺ | mEq/dl | 144 | 142 | 142 |
|  | K⁺ | mEq/dl | 4.3 | 4.3 | 4.2 |
|  | Cl⁻ | mEq/dl | 96 | 98 | 98 |

INDUSTRIAL APPLICABILITY

As described above, the transcriptional regulatory sequence according to the present invention is capable of killing selectively tumor cells by inducing tumor-specific, high-efficiency expression of a gene operably linked thereto. Therefore, the transcriptional regulatory sequence is useful as an anticancer agent with minimum side effects.

What is claimed is:

1. A transcriptional regulatory sequence with a wild-type human telomere reverse transcriptase (hTERT) promoter having two c-Myc binding sites and five Sp1 binding sites, functionally linked to at least one additional c-Myc binding site and at least one additional Sp1 binding site wherein the Sp1 binding site is functionally linked to a 3'-end of the hTERT promoter.

2. The transcriptional regulatory sequence as set forth in claim 1, wherein the c-Myc binding site is selected from the group consisting of SEQ ID NOS: 2, 3 and 4.

3. The transcriptional regulatory sequence as set forth in claim 1, wherein the Sp1 binding site is selected from the group consisting of SEQ ID NOS: 5, 6, 7, 8, 9 and 10.

4. The transcriptional regulatory sequence as set forth in claim 1, wherein a 5'-end or a 3'-end of the wild-type hTERT promoter is linked to at least one additional c-Myc binding site and at least one additional Sp1 binding site wherein the Sp1 binding site is functionally linked to a 3'-end of the hTERT promoter.

5. The transcriptional regulatory sequence as set forth in claim 1, wherein the transcriptional regulatory sequence has the nucleotide sequence of SEQ ID NO: 13.

6. A recombinant viral vector comprising the transcriptional regulatory sequence of claim 1, which is operably linked to a gene required for viral replication.

7. The recombinant viral vector as set forth in claim 6, wherein the viral vector is a virus belonging to the genus Adenoviridiae.

8. The recombinant viral vector as set forth in claim 6, wherein the gene required for viral replication is an adenovirus early gene.

9. The recombinant viral vector as set forth in claim 8, wherein the adenovirus early gene is an E1A gene.

10. The recombinant viral vector as set forth in claim 7, wherein the adenovirus comprises a deletion of an E1B-19 kDa gene.

11. The recombinant viral vector as set forth in claim 10, wherein the recombinant viral vector is KCCM-10470.

12. A recombinant viral vector comprising the transcriptional regulatory sequence of claim 1, which is operably linked to a therapeutic transgene.

13. The recombinant viral vector as set forth in claim 12, wherein the therapeutic transgene is selected from the group consisting of tumor suppressor genes, antigenic genes, cytotoxic genes, cytostatic genes, apoptotic genes and anti-angiogenic genes.

14. The recombinant viral vector as set forth in claim 12, wherein the viral vector is a virus belonging to the genus Adenoviridiae.

15. The recombinant viral vector as set forth in claim 13, wherein the therapeutic transgene is introduced in place of an adenovirus E1 gene, and the recombinant viral vector is replication-deficient.

16. The recombinant viral vector as set forth in claim 13, wherein the therapeutic transgene is introduced in place of an adenovirus E3 gene, and the recombinant viral vector is replication-competent.

17. The recombinant viral vector as set forth in claim 13, wherein the therapeutic transgene is introduced in place of an adenovirus E1A gene, and the recombinant viral vector comprises a deletion of adenovirus E1 and E3 genes.

18. A recombinant non-viral vector comprising the transcriptional regulatory sequence of claim 1, which is operably linked to a therapeutic transgene.

19. The recombinant non-viral vector as set forth in claim 18, wherein the therapeutic transgene is selected from the group consisting of tumor suppressor genes, antigenic genes, cytotoxic genes, cytostatic genes, apoptotic genes and anti-angiogenic genes.

20. A host cell transformed or transfected with the recombinant viral vector of claim 6.

21. A host cell transformed or transfected with the recombinant viral vector of claim 12.

22. A host cell transformed or transfected with the recombinant non-viral vector according to claim 18.

23. A pharmaceutical composition comprising: (a) a therapeutically effective amount of a recombinant viral vector comprising a transcriptional regulatory sequence comprising a wild-type human telomere reverse transcriptase (hTERT) promoter having two c-myc binding sites and five Sp1 binding sites, functionally linked to a at least one additional c-Myc binding site and at least one additional Sp1 binding site wherein the Sp1 binding site is functionally linked to a 3'-end of the hTERT promoter, wherein the transcriptional regulatory sequence is operably linked to a gene required for viral replication; and (b) a pharmaceutically acceptable carrier.

24. The pharmaceutical composition as set forth in claim 23, wherein the viral vector is a virus belonging to the genus Adenoviridiae.

25. A pharmaceutical composition comprising: (a) a therapeutically effective amount of a recombinant viral vector with a transcriptional regulatory sequence comprising a wild-type human telomere reverse transcriptase (hTERT) promoter having two c-Myc binding sites and five Sp1 binding sites, functionally linked to at least one additional c-Myc binding site and at least one additional Sp1 binding site wherein the Sp1 binding site is functionally linked to a 3'-end of the hTERT promoter, wherein the transcriptional regulatory sequence is operably linked to a therapeutic transgene; and (b) a pharmaceutically acceptable carrier.

26. The pharmaceutical composition as set forth in claim 25, wherein the viral vector is a virus belonging to the genus Adenoviridiae.

27. A pharmaceutical composition comprising: (a) a therapeutically effective amount of a recombinant non-viral vector with a transcriptional regulatory sequence comprising a wild-type human telomere reverse transcriptase (hTERT) promoter having two c-Myc binding sites and five Sp1 binding sites, functionally linked to at least one additional c-Myc binding site and at least one additional Sp1 binding site wherein the Sp1 binding site is functionally linked to a 3'-end of the hTERT promoter, wherein the transcriptional regulatory sequence is operably linked to a therapeutic transgene; and (b) a pharmaceutically acceptable carrier.

* * * * *